(12) United States Patent
Tzvieli et al.

(10) Patent No.: US 10,165,949 B2
(45) Date of Patent: Jan. 1, 2019

(54) ESTIMATING POSTURE USING HEAD-MOUNTED CAMERAS

(71) Applicant: Facense Ltd., Kiryat Tivon (IL)

(72) Inventors: Arie Tzvieli, Berkeley, CA (US); Ari M Frank, Haifa (IL); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 260 days.

(21) Appl. No.: 15/182,592

(22) Filed: Jun. 14, 2016

(65) Prior Publication Data

US 2016/0360970 A1 Dec. 15, 2016

Related U.S. Application Data

(60) Provisional application No. 62/175,319, filed on Jun. 14, 2015, provisional application No. 62/202,808, filed on Aug. 8, 2015.

(51) Int. Cl.
| | |
|---|---|
| *G02B 27/00* | (2006.01) |
| *G06F 3/01* | (2006.01) |
| *G02B 27/01* | (2006.01) |
| *H04N 13/00* | (2018.01) |
| *A61B 5/01* | (2006.01) |
| *A61B 5/16* | (2006.01) |
| *A61B 5/00* | (2006.01) |
| *G01J 5/12* | (2006.01) |
| *G01J 5/02* | (2006.01) |
| *G01J 5/00* | (2006.01) |

(52) U.S. Cl.
CPC ............ *A61B 5/015* (2013.01); *A61B 5/0075* (2013.01); *A61B 5/165* (2013.01); *A61B 5/6803* (2013.01); *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 2562/0271* (2013.01); *A61B 2562/0276* (2013.01); *A61B 2576/00* (2013.01); *G01J 2005/0077* (2013.01); *G01J 2005/0085* (2013.01)

(58) Field of Classification Search
None
See application file for complete search history.

(56) References Cited

U.S. PATENT DOCUMENTS

| | | | |
|---|---|---|---|
| 5,143,086 A | 9/1992 | Duret et al. | |
| 5,664,578 A | 9/1997 | Boczan | |

(Continued)

FOREIGN PATENT DOCUMENTS

| | | |
|---|---|---|
| EP | 2233071 A1 | 9/2013 |
| WO | WO2016025323 | 2/2016 |

OTHER PUBLICATIONS

Lv et al., "Touch-less interactive augmented reality game on vision-based wearable device," Pers Ubiquit Comput (2015) 19:551-567.*

(Continued)

*Primary Examiner* — Soo Shin
(74) *Attorney, Agent, or Firm* — Active Knowledge Ltd.

(57) ABSTRACT

System and method for estimating posture of a user based on a model and images captured by at least two head-mounted cameras that are worn by the user and are oriented downward such that portions of the user's torso are in the respective fields of view of the cameras when the user stands up straight.

19 Claims, 14 Drawing Sheets

(56) References Cited

U.S. PATENT DOCUMENTS

| | | | |
|---|---|---|---|
| 6,121,953 | A | 9/2000 | Walker |
| 6,286,958 | B1 | 9/2001 | Koest et al. |
| 6,771,423 | B2 | 8/2004 | Geist |
| 6,837,615 | B2 | 1/2005 | Newman |
| 6,996,256 | B2 | 2/2006 | Pavlidis |
| 7,027,621 | B1 | 4/2006 | Prokoski |
| 7,135,980 | B2 | 11/2006 | Moore et al. |
| 7,138,905 | B2 | 11/2006 | Pavlidis et al. |
| 8,149,273 | B2 | 4/2012 | Liu et al. |
| 8,289,443 | B2 | 10/2012 | MacKenzie |
| 8,334,872 | B2 | 12/2012 | Epps et al. |
| 8,360,986 | B2 | 1/2013 | Farag et al. |
| 8,573,866 | B2 | 11/2013 | Bond et al. |
| 8,585,588 | B2 | 11/2013 | Kovarik et al. |
| 8,694,899 | B2 * | 4/2014 | Goossens ............... G06Q 10/10 715/706 |
| 8,723,790 | B1 | 5/2014 | Schaefer |
| 8,768,438 | B2 | 7/2014 | Mestha et al. |
| 8,786,698 | B2 | 7/2014 | Chen et al. |
| 8,855,384 | B2 | 10/2014 | Kyal et al. |
| 8,964,298 | B2 | 2/2015 | Haddick et al. |
| 9,019,174 | B2 | 4/2015 | Jerauld |
| 9,020,185 | B2 | 4/2015 | Mestha et al. |
| 9,194,749 | B2 | 11/2015 | Pompei |
| 9,211,069 | B2 | 12/2015 | Larsen et al. |
| 9,370,302 | B2 * | 6/2016 | Krueger ............... A61B 3/113 |
| 9,410,854 | B2 | 8/2016 | Padiy |
| 9,569,734 | B2 | 2/2017 | Thieberger et al. |
| 9,788,714 | B2 * | 10/2017 | Krueger ............... A61B 3/0041 |
| 2002/0080094 | A1 | 6/2002 | Biocca et al. |
| 2005/0083248 | A1 * | 4/2005 | Biocca ............... A41D 31/0088 345/8 |
| 2005/0271117 | A1 | 12/2005 | Grassl et al. |
| 2007/0047768 | A1 | 3/2007 | Gordon et al. |
| 2007/0248238 | A1 | 10/2007 | Abreu |
| 2007/0265507 | A1 | 11/2007 | de Lemos |
| 2008/0260212 | A1 | 10/2008 | Moskal et al. |
| 2009/0221888 | A1 | 9/2009 | Wijesiriwardana |
| 2009/0237564 | A1 | 9/2009 | Kikinis et al. |
| 2010/0191124 | A1 | 7/2010 | Prokoski |
| 2010/0280334 | A1 | 11/2010 | Carlson et al. |
| 2012/0062719 | A1 | 3/2012 | Debevec et al. |
| 2012/0105473 | A1 | 5/2012 | Bar-Zeev et al. |
| 2012/0197093 | A1 | 8/2012 | LeBoeuf et al. |
| 2012/0327194 | A1 | 12/2012 | Shiratori et al. |
| 2013/0072820 | A1 * | 3/2013 | Lee ............... G06F 19/3431 600/594 |
| 2013/0124039 | A1 | 5/2013 | Abreu |
| 2013/0215244 | A1 | 8/2013 | Mestha et al. |
| 2013/0241805 | A1 | 9/2013 | Gomez |
| 2013/0257709 | A1 | 10/2013 | Raffle et al. |
| 2013/0278631 | A1 * | 10/2013 | Border ............... G02B 27/017 345/633 |
| 2014/0180449 | A1 | 6/2014 | Sung |
| 2014/0282911 | A1 | 9/2014 | Bare et al. |
| 2014/0347265 | A1 * | 11/2014 | Aimone ............... G09G 3/003 345/156 |
| 2014/0366049 | A1 | 12/2014 | Lehtiniemi et al. |
| 2015/0087924 | A1 | 3/2015 | Li et al. |
| 2015/0148618 | A1 | 5/2015 | Sitko et al. |
| 2015/0157255 | A1 | 6/2015 | Nduka |
| 2015/0297126 | A1 | 10/2015 | Atsumori et al. |
| 2015/0310263 | A1 * | 10/2015 | Zhang ............... G06K 9/00315 382/103 |
| 2015/0326570 | A1 * | 11/2015 | Publicover ............... G06F 21/64 726/4 |
| 2015/0359443 | A1 | 12/2015 | Poh |
| 2016/0015289 | A1 | 1/2016 | Simon et al. |
| 2016/0037025 | A1 * | 2/2016 | Blum ............... H04N 5/2251 348/207.99 |
| 2016/0081622 | A1 | 3/2016 | Abreu |
| 2016/0091877 | A1 | 3/2016 | Fullam et al. |
| 2016/0098592 | A1 | 4/2016 | Lee et al. |
| 2016/0100790 | A1 | 4/2016 | Cantu et al. |
| 2016/0116979 | A1 * | 4/2016 | Border ............... G06F 3/013 345/156 |
| 2016/0170996 | A1 * | 6/2016 | Frank ............... G06F 17/30702 707/748 |
| 2016/0216760 | A1 * | 7/2016 | Trutna ............... G06F 3/015 |
| 2016/0224803 | A1 | 8/2016 | Frank et al. |
| 2016/0235324 | A1 | 8/2016 | Mershin et al. |
| 2016/0270656 | A1 | 9/2016 | Samec et al. |
| 2016/0342835 | A1 | 11/2016 | Kaehler |
| 2017/0007167 | A1 | 1/2017 | Kostic et al. |
| 2017/0053447 | A1 * | 2/2017 | Chen ............... G06T 19/006 |
| 2017/0231490 | A1 | 8/2017 | Toth et al. |
| 2017/0235931 | A1 | 8/2017 | Publicover et al. |

OTHER PUBLICATIONS

Balachandreswaran et al., WO 2016/095057 A1.*

Cardone, D., Pinti, P., & Merla, A. (2015). Thermal infrared imaging-based computational psychophysiology for psychometrics. Computational and mathematical methods in medicine, 2015.

Hawkes, P. W. (2012). Advances in Imaging and Electron Physics (vol. 171). Academic Press. Chapter 2.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Ioannou, S., Gallese, V., & Merla, A. (2014). Thermal infrared imaging in psychophysiology: potentialities and limits. Psychophysiology, 51(10), 951-963.

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Jenkins, S. D., & Brown, R. D. H. (2014). A correlational analysis of human cognitive activity using Infrared Thermography of the supraorbital region, frontal EEG and self-report of core affective state. QIRT.

Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.

Lewis, G. F., Gatto, R. G., & Porges, S. W. (2011). A novel method for extracting respiration rate and relative tidal volume from infrared thermography. Psychophysiology, 48(7), 877-887.

Carine Collé, Re-Experience Big-Data, 3 months group project with Sanya Rai Gupta and Florian Puech, UK, London, RCA, IDE, 2014, Amoeba.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Nhan, B. R., & Chau, T. (2010). Classifying affective states using thermal infrared imaging of the human face. IEEE Transactions on Biomedical Engineering, 57(4), 979-987.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Cross, C. B., Skipper, J. A., & Petkie, D. (May 2013). Thermal imaging to detect physiological indicators of stress in humans. In SPIE Defense, Security, and Sensing (pp. 87050I-87050I). International Society for Optics and Photonics.

Treacy Solovey, E., Afergan, D., Peck, E. M., Hincks, S. W., & Jacob, R. J. (2015). Designing implicit interfaces for physiological computing: Guidelines and lessons learned using fNIRS. ACM Transactions on Computer-Human Interaction (TOCHI), 21(6), 35.

(56) References Cited

OTHER PUBLICATIONS

Bernardi, L., Wdowczyk-Szulc, J., Valenti, C., Castoldi, S., Passino, C., Spadacini, G., & Sleight, P. (2000). Effects of controlled breathing, mental activity and mental stress with or without verbalization on heart rate variability. Journal of the American College of Cardiology, 35(6), 1462-1469.

Choi, J. S., Bang, J. W., Heo, H., & Park, K. R. (2015). Evaluation of Fear Using Nonintrusive Measurement of Multimodal Sensors. Sensors, 15(7), 17507-17533.

Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.

Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.

Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In The International Conference on Electronics and Software Science (ICESS2015) Proceedings (pp. 212-215).

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE vol. (vol. 7486, pp. 74860I-1).

Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.

Clay-Warner, J., & Robinson, D. T. (2015). Infrared thermography as a measure of emotion response. Emotion Review, 7(2), 157-162.

Pavlidis, I., Dowdall, J., Sun, N., Puri, C., Fei, J., & Garbey, M. (2007). Interacting with human physiology. Computer Vision and Image Understanding, 108(1), 150-170.

Sharma, N., Dhall, A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.

Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.

Murthy, R., & Pavlidis, I. (2006). Noncontact measurement of breathing function. IEEE Engineering in Medicine and Biology Magazine, 25(3), 57-67.

Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.

Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.

Daniel Afergan, Samuel W. Hincks, Tomoki Shibata, and Robert J.K. Jacob, Phylter: A System for Modulating Notications in Wearables Using Physiological Sensing.

Joyal, C. C., & Henry, M. (2013). Long-wave infrared functional brain imaging in human: a pilot study. The open neuroimaging journal, 7(1).

Horikoshi, T. (2014). Prototype Glasses-type Device with Videophone Capabilities—Hands-free Videophone.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Al-Khalidi, F. Q., Saatchi, R., Burke, D., Elphick, H., & Tan, S. (2011). Respiration rate monitoring methods: A review. Pediatric pulmonology, 46(6), 523-529.

Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.

Merla, A. (2014). Thermal expression of intersubjectivity offers new possibilities to human—machine and technologically mediated interactions.

Rajoub, B. A., & Zwiggelaar, R. (2014). Thermal facial analysis for deception detection. IEEE transactions on information forensics and security, 9(6), 1015-1023.

Pavlidis, I., & Levine, J. (2002). Thermal image analysis for polygraph testing. IEEE Engineering in Medicine and Biology Magazine, 21(6), 56-64.

Sharma, N., Dhall, A., Gedeon, T., & Goecke, R. (2014). Thermal spatio-temporal data for stress recognition. EURASIP Journal on Image and Video Processing, 2014(1), 28.

Fei, J., & Pavlidis, I. (2010). Thermistor at a distance: unobtrusive measurement of breathing. IEEE Transactions on Biomedical Engineering, 57(4), 988-998.

Jovanov, E., Raskovic, D., & Hormigo, R. (2001). Thermistor-based breathing sensor for circadian rhythm evaluation. Biomedical sciences instrumentation, 37, 493-498.

Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.

Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

Written opinion of the international searching authority, PCT/IB2017/056066, dated Jan. 29, 2018.

Written opinion of the international searching authority, PCT/IB2017/056067, dated Jan. 29, 2018.

Written opinion of the international searching authority, PCT/IB2017/056069, dated Jan. 29, 2018.

Alghoul, K., Alharthi, S., Al Osman, H., & El Saddik, A. (2017). Heart Rate Variability extraction from videos signals: ICA vs. EVM comparison. IEEE Access, 5, 4711-4719.

Ghahramani, A., Castro, G., Becerik-Gerber, B., & Yu, X. (2016). Infrared thermography of human face for monitoring thermoregulation performance and estimating personal thermal comfort. Building and Environment, 109, 1-11.

Aryal, A., Ghahramani, A., & Becerik-Gerber, B. (2017). Monitoring fatigue in construction workers using physiological measurements. Automation in Construction.

* cited by examiner

ESTIMATING POSTURE USING HEAD-MOUNTED CAMERAS

BACKGROUND

Many physiological responses are manifested in the temperatures (and changes to the temperatures) that are measured on various regions of the human face. For example, facial temperatures may help determine the amount of stress a person might be under or the level of concentration the person has at a given time. In another example, facial temperatures can help determine how a user feels, e.g., whether a user is nervous, calm, or happy.

Thus, monitoring and analyzing facial temperatures can be useful for many health-related and life-logging related applications. However, typically collecting such data over time, when people are going through their daily activities can be very difficult. Typically, collection of such data involves utilizing thermal cameras that are bulky, expensive and need to be continually pointed at a person's face. Additionally, due to the people's movements in their day-to-day activities, various complex image analysis procedures need to be performed (e.g., face tracking and registration) in order to collect the required measurements.

Therefore, there is a need for way to be able to collect measurements of facial temperatures, and/or changes to the facial temperatures, at various regions of a person's face. Preferably, the measurements need to be able to be collected over a long period of time, while the person may be performing various day-to-day activities.

SUMMARY

According to one embodiment, a system includes: a frame configured to be worn on the user's head; first and second cameras, coupled to the frame at locations that are to the right and to the left of the symmetry axis that divides the face to the right and left sides, respectively, and less than 15 cm away from the user's head; wherein the first and second cameras are oriented downward such that portions of the user's torso are in the respective fields of view of the first and second cameras when the user stands up straight; and a computer configured to estimate posture of the user based on a model and data received from the first and second cameras.

According to another embodiment, a method includes the following steps: receiving images from first and second head mounted cameras that are located to the right and to the left of the symmetry axis that divides the face of a user to the right and left sides, respectively; wherein the first and second cameras are located less than 15 cm away from the user's head, and are oriented downward such that portions of the user's torso are in the respective fields of view of the first and second cameras when the user stands up straight; and estimating posture of the user based on a model and the images.

BRIEF DESCRIPTION OF THE DRAWINGS

The embodiments are herein described by way of example only, with reference to the accompanying drawings. No attempt is made to show structural details of the embodiments in more detail than is necessary for a fundamental understanding of the embodiments. In the drawings.

DETAILED DESCRIPTION

Figure 1:
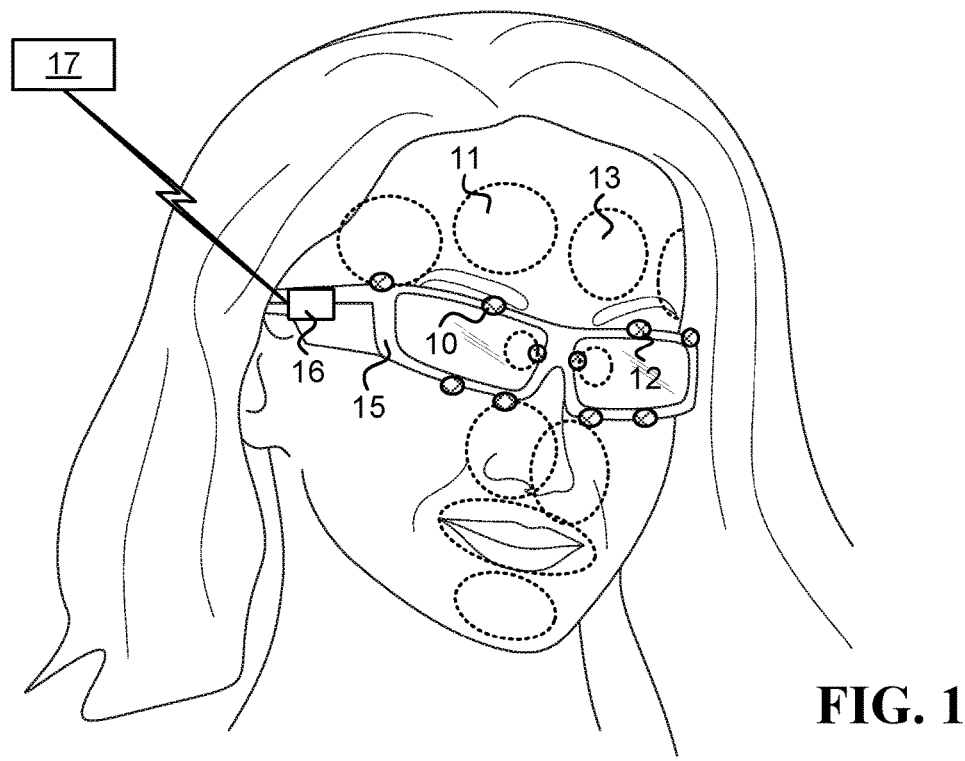
FIG. 1, FIG. 2, FIG. 3, and FIG. 4 illustrate various types of head mounted systems with cameras thereon, wherein the dotted circles and ellipses illustrate the region of interests of the cameras.

The term "thermal camera", as used herein, refers to a non-contact device comprising a thermal sensor useful for measuring wavelengths longer than 2500 nm. The thermal sensor may be used to measure spectral radiation characteristics of a black body at the user's body temperatures (around 310 K) according to Planck's radiation law. Although the thermal camera may also measure wavelengths shorter than 2500 nm, a camera that measures near-IR (such as 700-1200 nm), and is not useful for measuring wavelengths longer than 2500 nm, is referred to herein as near-IR camera and is not considered herein a thermal camera because it typically may not be used to effectively measure black body temperatures around 310 K. A thermal camera may include one or more sensors, where each sensor may include one or more sensing elements (that also referred to as pixels). For example, a thermal camera may include just one sensing element (i.e., one pixel, such as one thermopile sensor or one pyroelectric sensor), or a matrix containing thousands or even millions of pixels (such as a vector or a matrix of uncooled bolometer sensing elements). When a thermal capturing device utilizes optics for its operation, then the term "thermal camera" may refer to the optics (e.g., one or more lenses). When a thermal capturing device includes an optical limiter that limits the angle of view (such as in a pinhole camera, or a thermopile sensor inside a standard TO-5, TO-18, or TO-39 package with a window, or a thermopile sensor with a polished metal field limiter), then the term "thermal camera" may refer to the optical limiter. "Optical limiter" may also be referred to herein as a "field limiter" or "field of view limiter". Optionally, the field limiter may be made of a material with low emissivity and small thermal mass, such as Nickel-Silver and/or Aluminum foil.

The term "thermal camera" may also refer to a readout circuit adjacent to the thermal sensor, and may also include housing that holds the thermal sensor.

The term "thermal measurements of ROI" (usually denoted $TH_{ROI}$) may refer to at least one of the following: (i) "temperature measurements of ROI" (usually denoted $T_{ROI}$) taken for example with a thermopile sensor or a bolometer sensor which measure the temperature at the ROI, and (ii) "temperature change measurements of ROI" (usually denoted $\Delta T_{ROI}$) taken for example with a pyroelectric sensor that measures the temperature change at the ROI, or by watching the change in the measurements taken at different times by a thermopile sensor or a bolometer sensor.

Sentences such as "the thermal camera does not touch the ROI" specifically indicate that the thermal camera is not in contact with the user's skin, meaning that in a nominal operating condition there should be a space of at least 1 mm between the thermal camera (including its optics and housing) and the user's skin.

The term "circuit" is defined herein as an electronic device, which may be analog and/or digital, such as one or more of the following: an amplifier, a differential amplifier, a filter, analog and/or digital logic, a processor, a controller, a computer, an ASIC, and an FPGA.

Known systems for analyzing facial cues based on temperature measurements receive series of thermal images composed of pixels that represent temperature (T) measurements. Measuring the temperature is required in order to run a tracker and perform image registration, which compensate for the movements of the user in relation to the thermal camera and brings the images into precise alignment for analysis and comparison.

In one embodiment, a thermal camera (also referred to as a thermal sensor) is coupled to a frame worn on a user's head. In this configuration, the thermal camera moves with the user's head when the head changes its location and orientation in space, and thus there may be no need for a tracker and/or there may be no need for image registration. As a result, it is possible to run the image processing and/or signal processing algorithms on the series of thermal differences ($\Delta T$) measured by each thermal sensing element. Running the image/signal processing algorithms on the measured $\Delta T$ increases the accuracy of the system significantly compared to the case where $\Delta T$ is derived from images/signals representing temperature measurements (T).

Optionally, the temperature change at the ROI over time ($\Delta T_{ROI}$) is analyzed in relation to another parameter, such as the stimulus the user is exposed to, and/or other physiological measurements (such as EEG, skin conductance, pulse, breathing rate, and/or blood pressure).

Examples of thermopile sensors that may be useful for at least some of the embodiments herein include Texas Instruments "TMP006B Infrared Thermopile Sensor in Chip-Scale Package", Melexis "MLX90614 family Single and Dual Zone Infra-Red Thermometer in TO-39", HL-Planartechnik GmbH "TS118-3 thermopile sensor", Dexter Research Center, Inc. "DX-0875 detector", Dexter Research Center, Inc. "Temperature Sensor Module (TSM) with ST60 thermopile and onboard ASIC for amplification, digitizing, temperature compensation and calibration". When it is assumed that the sensor keeps measuring the same area on the object, these examples of thermopile sensors can provide readings of $\Delta T$, where often the measurement error of $\Delta T$ is much smaller than the measurement error of T. Therefore, maintaining the thermal camera pointed at the ROI, also when the user's head makes angular movements, enables at least some of the embodiments to utilize the more accurate $\Delta T$ measurement to identify fine cues that may not be identified based on image processing of temperature measurements (T) received from a camera that is not continuously pointed at the ROI (assuming sensors with same characteristics are used in both scenarios). In some embodiment, the performances of a thermopile and/or bolometer sensors may be improved using techniques such as described in U.S. Pat. No. 6,129,673.

In some embodiments, a thermal camera comprises a thermopile sensor configured to provide temperature readings in frequency below a frequency selected from the group of: 15 Hz, 10 Hz, 5 Hz, and 1 Hz.

In some embodiments, the field of view of the thermal camera is limited by a field limiter. For example, the thermal camera may be based on a Texas Instruments TMP006B IR thermopile utilizing a thin polished metal field limiter, or based on Melexis MLX90614 IR thermometers in TO-39 package. It is to be noted that the weight of the TMP006B or MLX90614 based thermal cameras is below 2 g, each.

For a better understanding of some of the disclosed embodiments, and not because the following theoretical discussion is necessary to make and/or use the disclosed embodiments, the following non-limiting theoretical discussion explains why the accuracy of the object temperature change ($\Delta T$) readings is expected to often be better than the accuracy of the object temperature (T) readings when dealing with sensors that measure temperature, such as thermopiles. If the following theoretical discussion is inaccurate then it should be disregarded and it is not to limit the scope of the disclosed embodiments in any way.

One problem with thermometers is that object temperature is hard to measure. Exact sensor output for a given object's temperature depends on properties of each particular sensing pixel, where each sensing pixel of the same sensor model may have its unique zero point, unique non-linear coefficients, and unique electrical properties. However, when it comes to a very small change in object temperature, such as from 35.7 C to 35.9 C, then the zero point has a small impact when measuring difference between two readings, and the nonlinear effects is small since the difference itself is small. For example, although the uniformity of different Texas Instruments TMP006B infrared thermopile sensors is usually not good, the response of each particular sensor is quite linear and stable, meaning that with proper calibration and filtering, it is possible to achieve 0.1 C temperature difference precision, or even better.

Accuracy of a matrix of sensing pixels is given in terms of temperature accuracy. For example, accuracy of 0.2 C means that any pixel in the matrix will provide the same ±0.2 C temperature for a given object. However, when the current reading of a certain pixel is compared to its previous readings (as opposed to the case where the current reading of the certain pixel is compared to previous readings of other pixels), then the variability between the pixels essentially does not affect the accuracy of $\Delta T$ obtained from the certain pixel. For example, Micro80P Thermal Imaging Sensor, manufactured by Sofradir-EC, has an Array Uniformity<1.5% deviation; this large array uniformity may not affect the accuracy of $\Delta T$ obtain from a certain pixel in the unique case where the certain pixel remains pointed at the ROI also when the user's head makes angular movements.

The specific detectivity, noted as D*, of bolometers and thermopiles depends on the frequency of providing the temperature readings. In some embodiments, there is essentially no need for tracking and/or image registration, thus it is possible to configure the thermopile to provide temperature readings in frequencies such as 15 Hz, 10 Hz, 5 Hz, and even 1 Hz or lower. A thermopile with reaction time around 5-10 Hz may provide the same level of detectivity as a bolometer, as illustrated for example in the publication Dillner, U., Kessler, E., & Meyer, H. G. (2013), "Figures of merit of thermoelectric and bolometric thermal radiation sensors", J. Sens. Sens. Syst, 2, 85-94. In some cases, operating at low frequencies provides benefits that cannot be achieved when there is a need to apply image registration and run a tracker, which may enable a reduction in price of the low frequency sensors that may be utilized.

In some embodiments of thermopiles, there are many thermocouples where one side of each couple is thermally connected to a measuring membrane, while another is connected to the main body of the thermometer. In each thermocouple, a voltage dependent on temperature difference is generated according to Seebeck's effect. When these thermocouples are connected in series, the effect is multiplied by the number of thermocouples involved. For each thermocouple, the voltage generated is defined by Seebeck's formula: $dV=S*dT$, where dV is the generated voltage difference, dT is the temperature difference, and S is a Seebeck coefficient that is a material-dependent coefficient (for example 0.5 mV/K). Since accurate voltage measurement of several microvolts is achievable, this method may allow detection of $\Delta T$ at a resolution of 0.01K or less. Although, since a thermocouple senses the difference between two ends and not the object temperature, it is required to know the temperature of the main thermometer body with high precision, otherwise the precision drops. More information on Seebeck's effect and micromachined thermopiles can be found in the publication Graf, A., Arndt, M., & Gerlach, G. (2007), "Seebeck's effect in micromachined thermopiles for infrared detection. A review", Proc. Estonian Acad. Sci. Eng, 13(4), 338-353.

In some embodiments of bolometers, the measuring membrane is connected to a material that changes its resistance significantly when the temperature is changed as follows: $R=R0 (1+a*dT)$, where R is resistance at a given temperature, and R0 and 'a' are material-dependent parameters. In one example of vanadium pentoxide, the sensitivity highly depends on the layer creation technology, and the resistance change may be as high as 4% per Kelvin, where 2% may be a typical value. Since resistance value depends on the temperature, the measurements are theoretically independent of the temperature of the main thermometer body. However, in practice, there may be a heat flow between the measuring membrane and the main body, which imposes a practical limit on the maximum temperature difference. In addition, the maximum temperature difference may not be the same in both negative and positive directions, and with higher differences causing an increase in the measurement error.

Both bolometers and thermopiles work better when the object temperature is close to the detector temperature. Maintaining the temperature of the detector constant is helpful to detect small differences in object temperature precisely, thus, in one embodiment, the detectors are placed on a plate of metal having high thermal conductance, such as aluminum or copper, which optionally has Peltier elements and several high precision contact thermometers for temperature control.

Using several detectors instead of a single detector may decrease signal noise and increase stability. If the measurement electronics of a particular sensor has a long-term measurement drift (which may be added at on-chip circuit level), then using multiple sensors may be a practical way to remove the drift, such as in a small temperature-stabilized platform with several sensors.

When it comes to detection of differences in an object's temperature, often, one limitation is the ability to keep the sensors' temperature constant. At least with several relatively inexpensive commercially available sensors, temperature is measured with 0.01-0.02 C steps, meaning that even a single sensor may be able to detect $\Delta T$ of 0.04 C or less. However, for thermopile sensors, the detected signal is the difference between the object temperature and the thermometer case temperature, thus the case temperature needs to be measured with the appropriate precision. In one example, such high precision measurements may be obtained utilizing high quality temperature stabilization of the thermometer's base plate, which may require several high-precision contact thermometers and Peltier elements to control the temperature. In another example, the thermal camera uses bolometers, which are not so sensitive to case temperature, and enable operation in room temperature as long as the environment is maintained with no more than ±3 C changes.

Examples of pyroelectric sensors that may be useful for at least some of the embodiments herein include: (i) Excelitas Technologies analog pyroelectric non-contact sensor series, having one, two, four, or more elements; (ii) Excelitas Technologies DigiPyro® digital pyroelectric non-contact sensor series, having two, four, or more elements; and (ii) Murata Manufacturing Co., Ltd. dual type pyroelectric infrared sensor series, or Parallel Quad Type Pyroelectric Infrared Sensor Series.

In some embodiments, as a result of being physically coupled to the frame, a thermal camera remains pointed at the ROI when the user's head makes angular movements. It is to be noted that sentences such as "the thermal camera is physically coupled to the frame" refers to both direct physical coupling to the frame, which means that the thermal camera is fixed to/integrated into the frame, and indirect physical coupling to the frame, which means that the thermal camera is fixed to/integrated into an element that is physically coupled to the frame. In both the direct and indirect physical coupling embodiments, the thermal camera remains pointed at the ROI when the user's head makes angular movements. In some examples, the rate of angular movement referred to in sentences such as "when the user's head makes angular movements" is above 0.02 rad/sec, 0.1 rad/sec, or 0.4 rad/sec. Moreover, sentences such as "the thermal camera . . . is not in physical contact with the ROI" mean that the thermal camera utilizes a non-contact sensor that does not touch the ROI directly in a manner similar to a thermistor that needs to be in physical contact with the ROI in order to measure the ROI.

In some embodiments, a thermal camera may comprise an uncooled thermal sensor. Herein, an uncooled thermal sensor refers to a sensor useful for measuring wavelengths longer than 2500 nm, which: (i) operates at ambient temperature, or (ii) is stabilized at a temperature that is no more than ±20 Celsius from the ambient temperature. Optionally, the thermal camera utilizes for its operation a thermopile sensor. The reference Pezzotti, G., Coppa, P., & Liberati, F. (2006), "Pyrometer at low radiation for measuring the forehead skin temperature", Revista Facultad de Ingeniería Universidad de Antioquia, (38), 128-135 describes one example of measuring the forehead temperature with a thermopile that provides accuracy better than 0.2 C, without necessitating physical contact with the forehead, and with a working distance between 350 and 400 mm. The optics in this example involves a single aspherical mirror, which may, or may not, be necessary when the thermal camera is located just a few centimeters from the ROI.

In some embodiments, a thermal camera utilizes for its operation at least one of the following uncooled thermal sensors: a bolometer sensor, a pyroelectric sensor, and a ferroelectric sensor. In other embodiments, a thermal camera comprises a cool thermal sensor.

For various purposes, thermal cameras may be positioned in certain locations, e.g., in order to be able to take measurements of a certain region of interest (ROI). Optionally, in order to provide useful measurements a thermal camera may be located away from a specific region, such as being located outside of the exhale streams of the mouth and nostrils. Herein, sentences such as "located outside the exhale streams of the mouth and nostrils" means located outside most of the normally expected exhale stream of the mouth and located outside most of the normally expected exhale streams from the nostrils. The normally expected exhale streams are determined according to a normal human who breathes normally, when having a relaxed (neutral) face, and when the neck, jaw, and facial muscles are not stretched nor contracted. For example, a thermal camera is considered to be located outside the exhale streams from the nostrils when it is located to the right of the right nostril, and/or to the left of the left nostril, and/or outside a 3D rectangle that extends from below the tip of the nose to the lower part of the chin with a base size of at least 4×4 cm. In another example, a thermal camera is considered to be located outside the exhale stream of the mouth when it is located outside a horizontal cylinder having height of 10-20 cm and diameter of 4-10 cm, where the top of the cylinder touches the base of the nose.

In the case of a thermal camera based on a thermal sensor such as a thermopile, the thermopile's reference junctions may compensate for changes in the temperature of the ROI. If the reference junction temperature is fixed, for example by placing the junctions over a heat sink and/or insulating them, then exhale streams from the nostrils and/or mouth may not affect the temperature difference between the ROI and the sensing junctions. However, when the reference junction temperature is not fixed, then the breath passing over the sensor may change the reading of the thermopile merely because the exhale stream is close to body temperature. For example, if the thermopile was at room temperature and the temperature of the reference junctions is essentially fixed, then the thermopile would register a voltage that is proportional to a change to the temperature between ROI and room temperature. However, if the sensing junctions are exposed to the exhale stream, then the thermopile may measure a wrong temperature of the ROI. In order to avoid such an error, in one embodiment a non-well isolated thermal camera is located outside the exhale streams, which means that the thermal camera is not placed in front of the nostrils and/or in front of the mouth, but to the side, above, below, and/or in any other possible location that is away from the nostrils and the mouth. In some embodiments, an additional thermal camera may be located inside the exhale streams from at least one of the mouth and the nostrils.

In one example, "a frame configured to be worn on the user's head" is interpreted as a frame that loads more than 50% of its weight on the user's head. For example, the frame in Oculus Rift and HTC Vive includes the foam placed on the user's face and the straps; the frame in Microsoft HoloLens includes the adjustment wheel in the headband placed on the user's head. In another example, "a frame configured to be worn on the user's head" may be an eyeglasses frame, which holds prescription and/or UV-protective lenses.

In one example, wide angular movements are interpreted as angular movements of more than 45 degrees. In one example, the locations of the first and second cameras relative to the user's head do not change even when the user's head performs wide angular and lateral movements, wherein wide angular and lateral movements are interpreted as angular movements of more than 60 degrees and lateral movements of more than 1 meter.

In one example, the frame is similar to extending side arms of eyeglasses. The frame may be positioned behind a user's ears to secure the HMS to the user. The frame may further secure the HMS to the user by extending around a rear portion of the user's head. Additionally or alternatively, the frame may connect to or be affixed within a head-mountable helmet structure.

The positions of the cameras on the figures are just for illustration. The cameras may be placed at other positions on the HMS. One of more of the visible light cameras may be configured to capture images at various resolutions or at different frame rates. Many video cameras with a small form-factor, such as those used in cell phones or webcams, for example, may be incorporated into some of the embodiments.

Further, illustrations and discussions of a camera represent one or more cameras, where each camera may be configured to capture the same view, and/or to capture different views (i.e., they may have essentially the same or different fields of view). In one embodiment, one or more of the cameras may include one or more elements, such as a gyroscope, an accelerometer, and/or a proximity sensor. Other sensing devices may be included within the camera, and/or in addition to the camera, and other sensing functions may be performed by one or more of the cameras.

In one embodiment, because facial structures may differ from user to user, the HMS may calibrate the direction, position, algorithms, and/or characteristics of one or more of the cameras and/or light sources based on the facial structure of the user. In one example, the HMS calibrates the positioning of a camera in relation to a certain feature on the user's face. In another example, the HMS changes, mechanically and/or optically, the positioning of a camera in relation to the frame in order to adapt itself to a certain facial structure.

Various systems described in this disclosure may include a display that is coupled to a frame worn on a user's head, e.g., a frame of a head-mounted system (HMS). In some embodiments, the display coupled to the frame is configured to present digital content to the user. Phrases in the form of "a display coupled to the frame" are to be interpreted as one or more of the following: (i) the frame can be worn and/or taken off together with the display such that when the user wears/takes off the HMS he/she also wears/takes off the display, (ii) the display is integrated with the frame, and optionally the display is sold together with the HMS, and/or (iii) the HMS and the display share at least one electronic element, such as a circuit, a processor, a memory, a battery, an optical element, and/or a communication unit for communicating with a non-head mounted computer.

Herein, a display may be any device that provides a user with visual images (e.g., text, pictures, and/or video). The images provided by the display may be two-dimensional or three-dimensional images. Some non-limiting examples of displays that may be used in embodiments described in this disclosure include: (i) screens and/or video displays of various devices (e.g., televisions, computer monitors, tablets, smartphones, or smartwatches), (ii) headset- or helmet-mounted displays such as augmented-reality systems (e.g., HoloLens), virtual-reality systems (e.g., Oculus rift, Vive, or Samsung GearVR), and mixed-reality systems (e.g., Magic Leap), and (iii) image projection systems that project images on a user's retina, such as Virtual Retinal Displays (VRD), which creates images by scanning low power laser light directly onto the retina.

In one embodiment, a helmet is coupled to the frame and configured to protect the user's scalp; wherein the helmet is selected from the group of: a sport helmet, a motorcycle helmet, a bicycle helmet, and a combat helmet. Phrases in the form of "a helmet coupled to the frame" are to be interpreted as one or more of the following: (i) the frame can be worn and/or take off together with the helmet such that when the user wears/takes off the helmet he/she also wears/takes off the HMS, (ii) the frame is integrated with the helmet and/or the helmet itself forms the frame, and optionally the HMS is sold together with the helmet, and/or (iii) the HMS and the helmet share at least one electronic element, such as an inertial measurement sensor, a circuit, a processor, a memory, a battery, an image sensor, and/or a communication unit for communicating with a non-head mounted computer.

In one embodiment, a brainwave headset is coupled to the frame and configured to collect brainwave signals of the user. Phrases in the form of "a brainwave headset coupled to the frame" are to be interpreted as one or more of the following: (i) the frame can be worn and/or take off together with the brainwave headset such that when the user wears/takes off the brainwave headset he/she also wears/takes off the HMS, (ii) the frame is integrated with the brainwave headset and/or the brainwave headset itself forms the frame, and optionally the HMS is sold together with the brainwave headset, and/or (iii) the HMS and the brainwave headset share at least one electronic element, such as an inertial measurement sensor, a circuit, a processor, a memory, a battery, and/or a communication unit.

FIG. 1, FIG. 2, FIG. 3, and FIG. 4 illustrate various types of head mounted systems with cameras thereon, wherein the dotted circles and ellipses illustrate the region of interests of the cameras. The cameras may be thermal cameras and/or visible light cameras.

Figure 5:
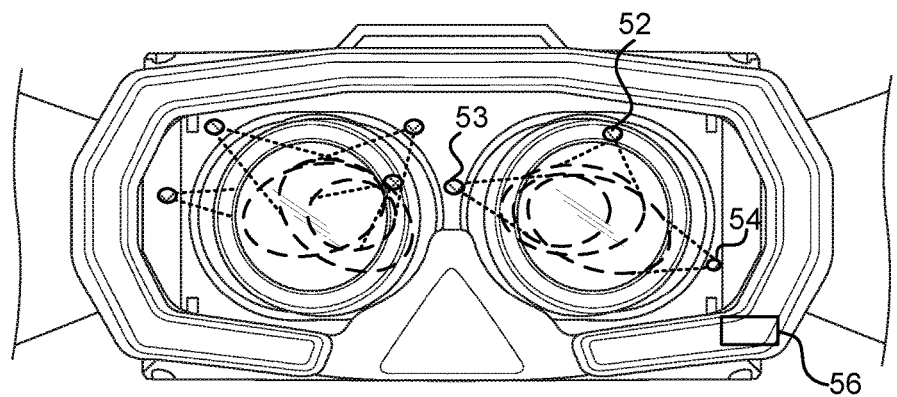
FIG. 5, FIG. 6, and FIG. 7 illustrate various potential locations to connect thermal cameras to various head mounted display frames in order to have at least some of the periorbital ROI within the field of view of one or more of the thermal cameras.
Figure 6:
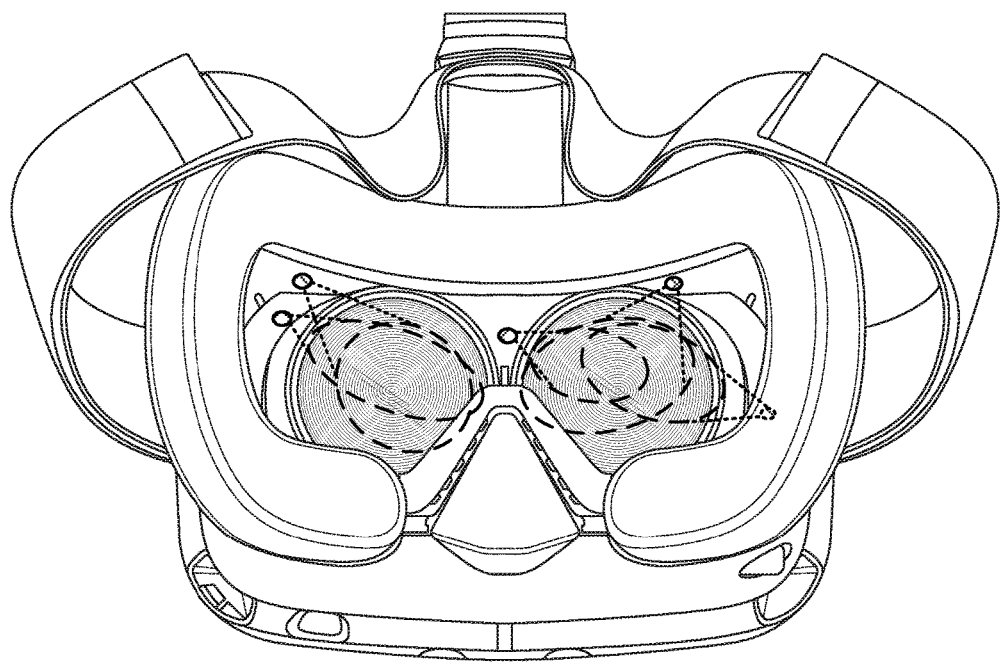
Figure 7:
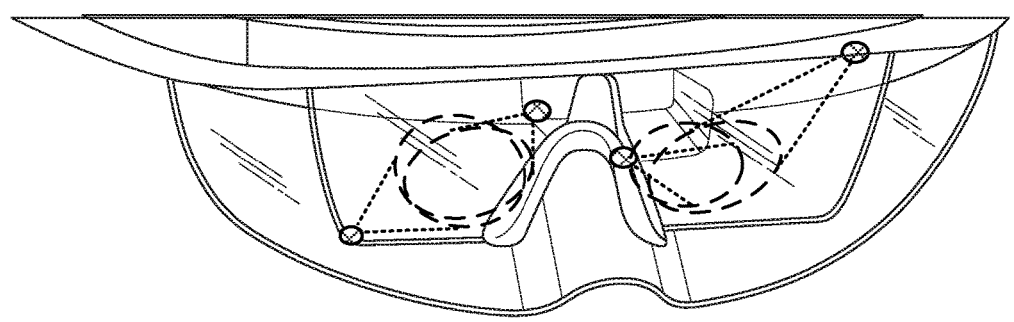

FIG. 5, FIG. 6, and FIG. 7 illustrate various potential locations to connect thermal cameras to various head mounted display frames in order to have at least some of the periorbital ROI within the field of view of one or more of the thermal cameras. Because the thermal cameras are located close to the ROI, they can be small, lightweight, and may be placed in many potential locations having line of sight to the respective ROIs.

Figure 9:
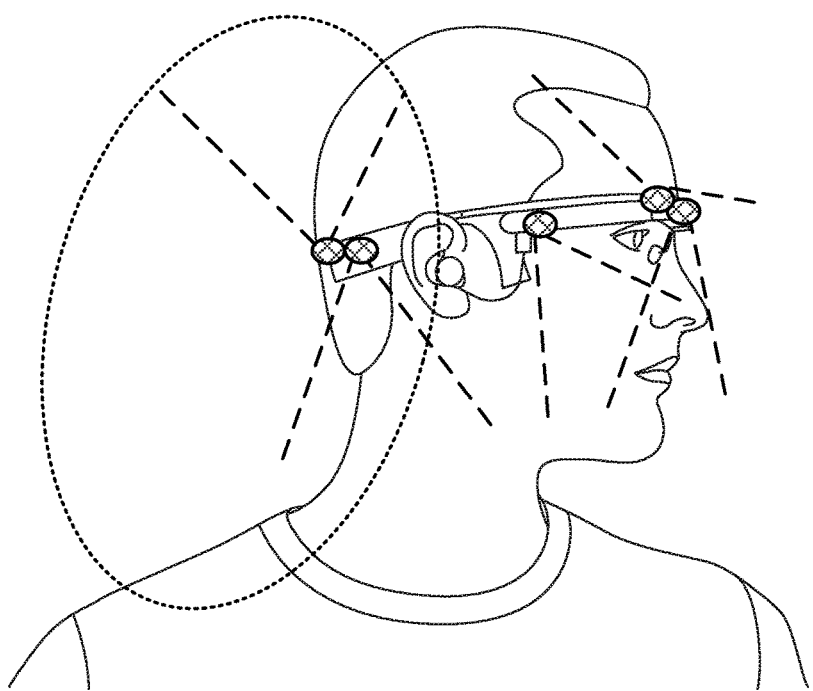
FIG. 9, FIG. 10, and FIG. 11 illustrate various types of head mounted systems with cameras thereon, wherein the dotted lines illustrate the fields of view of the cameras.
Figure 10:
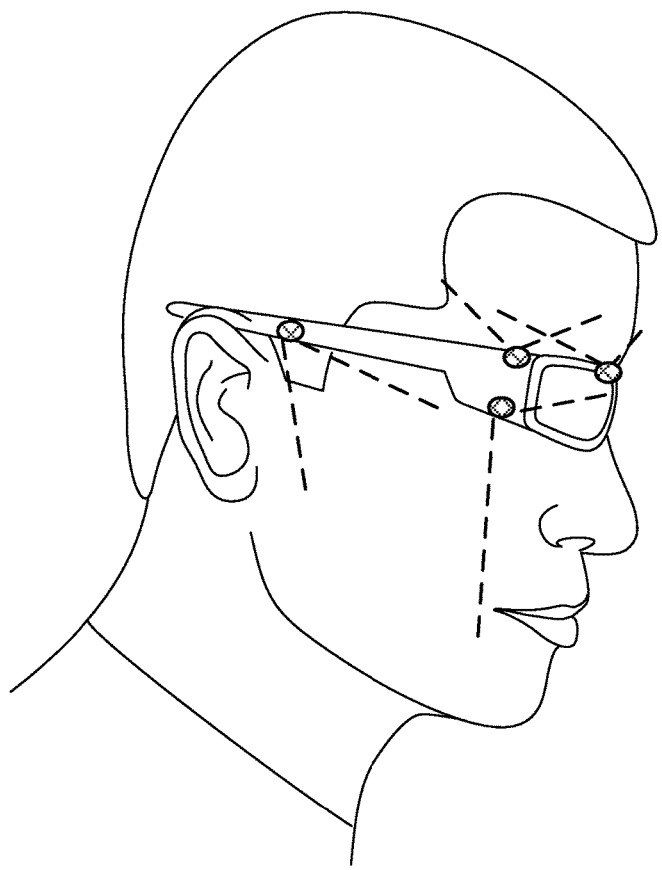
Figure 11:

FIG. 9, FIG. 10, and FIG. 11 illustrate various types of head mounted systems with cameras thereon, wherein the dotted lines illustrate the fields of view of the cameras. The cameras may be thermal cameras and/or visible light cameras.

As discussed above, collecting thermal measurements of various regions of a user's face can have many health-related (and other) applications. However, movements of the user and/or of the user's head can make acquiring this data difficult for many known approaches. To this end, some embodiments described herein utilize various combinations of thermal cameras that are coupled to a frame of a head-mounted system (also referred to as a "wearable system" or simply a "system"), as the descriptions of the following embodiments show.

FIG. 1 illustrates one embodiment of a system that includes a first thermal camera 10 and a second thermal camera 12 that are physically coupled to a frame 15 configured to be worn on a user's head. The first thermal camera is configured to take thermal measurements of a first region of interest 11 (the "first region of interest" denoted $ROI_1$, and the "thermal measurements of $ROI_1$" denoted $TH_{ROI1}$), where $ROI_1$ 11 covers at least a portion of the right side of the user's forehead, and the second thermal camera is configured to take thermal measurements of a second ROI ($TH_{ROI2}$), wherein $ROI_2$ 13 covers at least a portion of the left side of the user's forehead. Additionally, the first and second thermal cameras are not in physical contact with their corresponding ROIs, the overlap between $ROI_1$ and $ROI_2$ is below 80% of the smallest area from among the areas of $ROI_1$ and $ROI_2$, and as a result of being coupled to the frame, the thermal cameras remain pointed at their corresponding ROIs when the user's head makes angular movements.

In one embodiment, the system described above is configured to forward $TH_{ROI1}$ and $TH_{ROI2}$ to a processor 16 configured to identify a physiological response based on $TH_{ROI1}$ and $TH_{ROI2}$. The processor 16 may be located on the user's face, may be worn by the user, and/or may be located in a distance from the user, such as on a smartphone, a personal computer, a server, and/or on a cloud computer. The wearable processor 16 may communicate with the non-wearable processor 17 using any appropriate communication techniques.

Optionally, the physiological response identified by the processor (16 and/or 17) is indicative of at least one of the following: stress, mental workload, fear, sexual arousal, anxiety, pain, pulse, headache, and stroke.

In different embodiments, the ROIs mentioned above may cover slightly different regions on the user's face. In one example, the right side of the user's forehead covers at least 30% of $ROI_1$, and the left side of the user's forehead covers at least 30% of $ROI_2$. In another example, the right side of the user's forehead covers at least 80% of $ROI_1$, and the left side of the user's forehead covers at least 80% of $ROI_2$.

Measurements of the thermal cameras may be utilized for various calculations in different embodiments. For example, in one embodiment, the first and second thermal cameras measure temperatures at $ROI_1$ and $ROI_2$, respectively. In this embodiment, the system may further include a circuit configured to: receive a series of temperature measurements at $ROI_1$ and calculate temperature changes at $ROI_1$ ($\Delta T_{ROI1}$), receive a series of temperature measurements at $ROI_2$ and calculate temperature changes at $ROI_2$ ($\Delta T_{ROI2}$), and utilize $\Delta T_{ROI1}$ and $\Delta T_{ROI2}$ to identify a physiological response. Optionally, the system's nominal measurement error of the temperatures at $ROI_1$ is at least twice the system's nominal measurement error of the temperature changes at $ROI_1$ when the user's head makes angular movements above 0.02 rad/sec.

Optionally, the system's nominal measurement error of the temperatures at $ROI_1$ is at least five time the system's nominal measurement error of the temperature changes at $ROI_1$ when the user's head makes angular movements above 0.2 rad/sec.

Following is a description of another embodiment of a system that includes thermal cameras that take measurements of other regions of a user's face.

In one embodiment, a system includes first and second thermal cameras physically coupled to a frame configured to be worn on a user's head. The first thermal camera is configured to take thermal measurements of a first region of interest ($TH_{ROI1}$), where $ROI_1$ covers at least a portion of the right side frontal superficial temporal artery of the user, and the second thermal camera is configured to take thermal measurements of a second region of interest ($TH_{ROI2}$), where $ROI_2$ covers at least a portion of the left side frontal superficial temporal artery of the user. Additionally, the first and second thermal cameras are not in physical contact with their corresponding ROIs, and as a result of being coupled to the frame, the thermal cameras remain pointed at their corresponding ROIs when the user's head makes angular movements.

In one embodiment, the system described above is configured to forward $TH_{ROI1}$ and $TH_{ROI2}$ to a processor configured to identify a physiological response based on $TH_{ROI1}$ and $TH_{ROI2}$. Optionally, the physiological response is indicative of the user's arterial pulse. Additionally or alternatively, the physiological response may be indicative of at least one of the following: stress, mental workload, fear, anxiety, pain, headache, and stroke.

In one example, the physiological signal (such as pulse or respiration) has periodic features, the thermal camera includes multiple sensing elements, and the computer may extract temporal signals for individual pixels inside $ROI_2$, and/or extract temporal signals for pixel clusters inside $ROI_2$, depending on the movement and the noise level. The calculation of the physiological signal may include harmonic analysis, such as a fast Fourier transform, to the temperature signal and/or temperature change signal of each pixel, or pixel clusters, over time in a sliding window, which may be followed by a non-linear filter to reduce low-frequency signal leakage in the measurement frequency range. In cases where some pixels may be less informative than others, a clustering procedure may be implemented to remove the outliers. Then the frequency peaks in the set of pixels of interest may be used to vote for the dominant frequency component, the bin with the most votes is selected as the dominant frequency, and the estimate of the physiological signal may be obtained from the median filtered results of the dominant frequency components in a small sliding window.

One example of a contact-free heart rate and respiratory rate detection through measuring infrared light modulation emitted near superficial blood vessels or a nasal area, respectively, is described in the reference Yang, M., Liu, Q., Turner, T., & Wu, Y. (2008), "Vital sign estimation from passive thermal video", In Computer Vision and Pattern Recognition, 2008. CVPR 2008. IEEE Conference on (pp. 1-8). IEEE. Pulsating blood flow induces subtle periodic temperature changes to the skin above the superficial vessels by heat diffusion, which may be detected by thermal video to reveal the associated heart rate. The temperature modulations may be detected through pixel intensity changes in the ROI using a thermal camera, and the corresponding heart rate may be measured quantitatively by harmonic analysis of these changes on the skin area above the superficial temporal artery (in this context, "the skin area above the artery" refers to "the skin area on top of the artery").

In one embodiment, because the thermal camera is coupled to the frame, challenges such as dealing with complications caused by movements of the user, ROI alignment, tracking based on hot spots or markers, and motion compensation in the IR video—are simplified, and maybe even eliminated.

The temperature modulation level due to blood pulsating is far less than normal skin temperature, therefore, in one embodiment, the subtle periodic changes in temperature are quantify based on frame differences. For example, after an optional alignment, the frame differences against a certain reference frame are calculated for every frame, based on corresponding pixels or corresponding pixel clusters. The temperature differences may look like random noise in the first several frames, but a definite pattern appears close to half of the pulse period; then the temperature differences become noisy again as approaching the pulse period. The heart rate is estimated by harmonic analysis of the skin temperature modulation above the superficial temporal artery. In one embodiment, a similar method is applied to respiration rate estimation by measuring the periodic temperature changes around the nasal area.

FIG. 7 in U.S. Pat. No. 8,360,986 to Farag et al illustrates the right and left frontal superficial temporal artery ROIs of one person. The locations and dimensions of the right and left frontal superficial temporal artery ROIs may change to some extent between different people. Due to the inherent benefits obtained from the disclosed head mounted thermal cameras, it may be enough that $ROI_1$ and $ROI_2$ cover just a portion of the right and left frontal superficial temporal artery ROIs. Additionally or alternatively, $ROI_1$ and $ROI_2$ may cover greater areas than the ROIs illustrated in FIG. 7 in U.S. Pat. No. 8,360,986.

The following is yet another description of an embodiment of a system that includes thermal cameras that take measurements of certain regions of a user's face. In one embodiment, a system includes first and second thermal cameras physically coupled to a frame configured to be worn on a user's head. The first thermal camera is configured to take thermal measurements of a first region of interest ($TH_{ROI1}$), where $ROI_1$ covers at least a portion of the right side superficial temporal artery of the user. The second thermal camera is configured to take thermal measurements of a second region of interest ($TH_{ROI2}$), where $ROI_2$ covers at least a portion of the left side superficial temporal artery of the user. Additionally, the first and second thermal cameras are not in physical contact with their corresponding ROIs, and as a result of being coupled to the frame, the thermal cameras remain pointed at their corresponding ROIs when the user's head makes angular movements.

In one embodiment, the system described above is configured to forward $TH_{ROI1}$ and $TH_{ROI2}$ to a processor configured to identify a physiological response based on $TH_{ROI1}$ and $TH_{ROI2}$. Optionally, the physiological response is indicative of the user's arterial pulse. Additionally or alternatively, the physiological response is indicative of at least one of the following: stress, mental workload, fear, anxiety, pain, headache, and stroke.

FIG. 7 in U.S. Pat. No. 8,360,986 to Farag et al illustrates the right and left superficial temporal artery ROIs of one person. The locations and dimensions of the right and left superficial temporal artery ROIs may change to some extent between different people. Due to the inherent benefits obtained from the disclosed head mounted thermal cameras, it may be enough that $ROI_1$ and $ROI_2$ cover just a portion of the right and left superficial temporal artery ROIs. Additionally or alternatively, $ROI_1$ and $ROI_2$ may cover greater areas than the ROIs illustrated in FIG. 7 in U.S. Pat. No. 8,360,986.

Yet another example of a system that includes thermal cameras that take measurements of certain regions of a user's face is given is the following description. In one embodiment, a wearable system configured to take thermal measurements that enable identification of a physiological response includes at least a frame and first, second, third, and fourth thermal cameras. The frame configured to be worn on a user's head, and the first, second, third and fourth thermal cameras remain pointed at their respective ROIs when the user's head makes angular movements.

The first and second thermal cameras, physically coupled to the frame, at locations to the right and to the left of the symmetry axis that divides the user's face to the right and left sides, respectively, which are less than 15 cm away from the user's right and left pupils, respectively. The first thermal camera is configured to take thermal measurements of a first region of interest ($TH_{ROI1}$), where $ROI_1$ covers at least a portion of the right side of the user's forehead. The second thermal camera is configured to take thermal measurements of a second region of interest ($TH_{ROI2}$), where $ROI_2$ covers at least a portion of the user's left side of the forehead.

Figure 2:
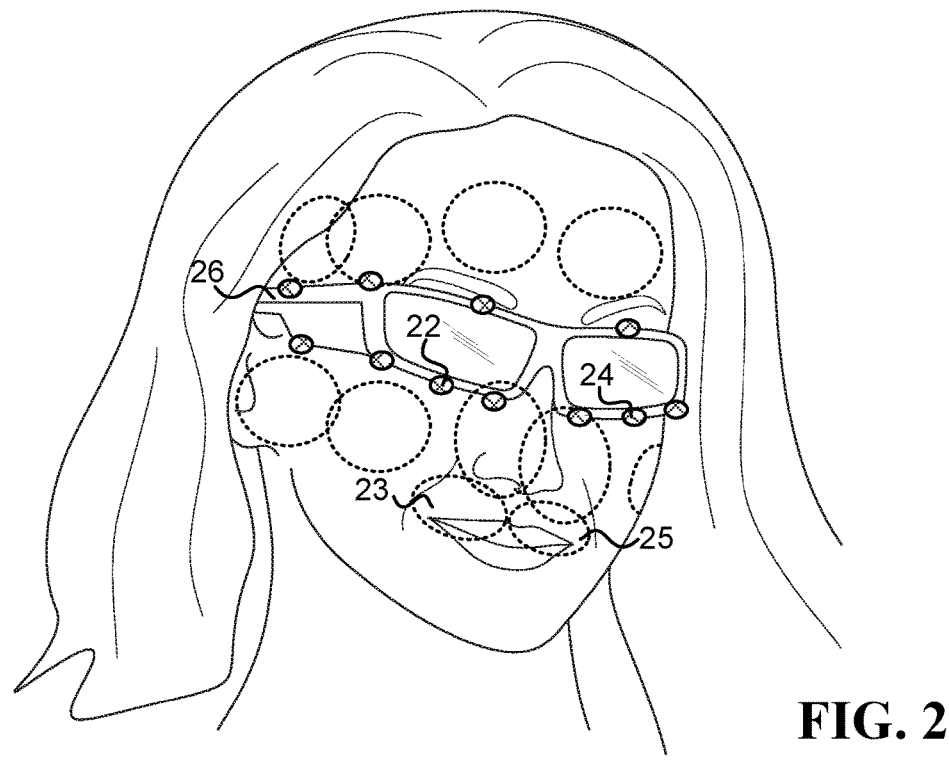
Figure 3:
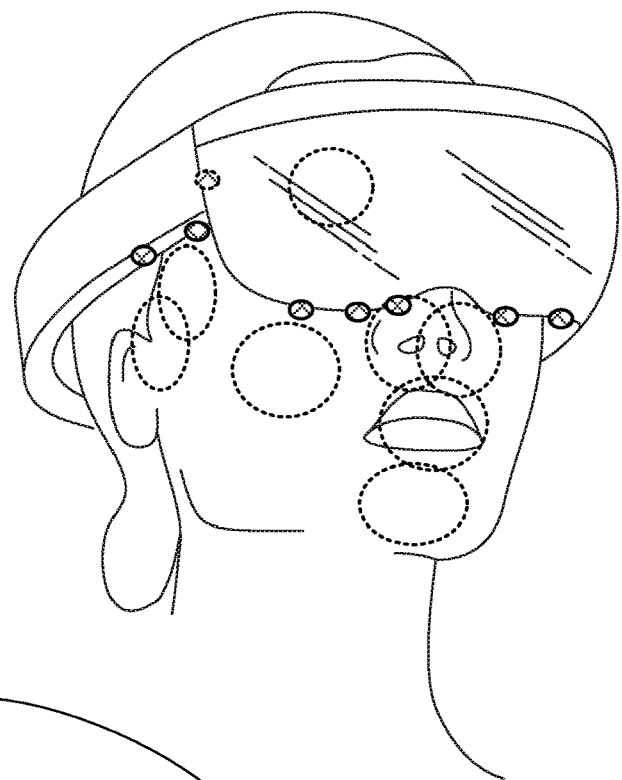
Figure 4:
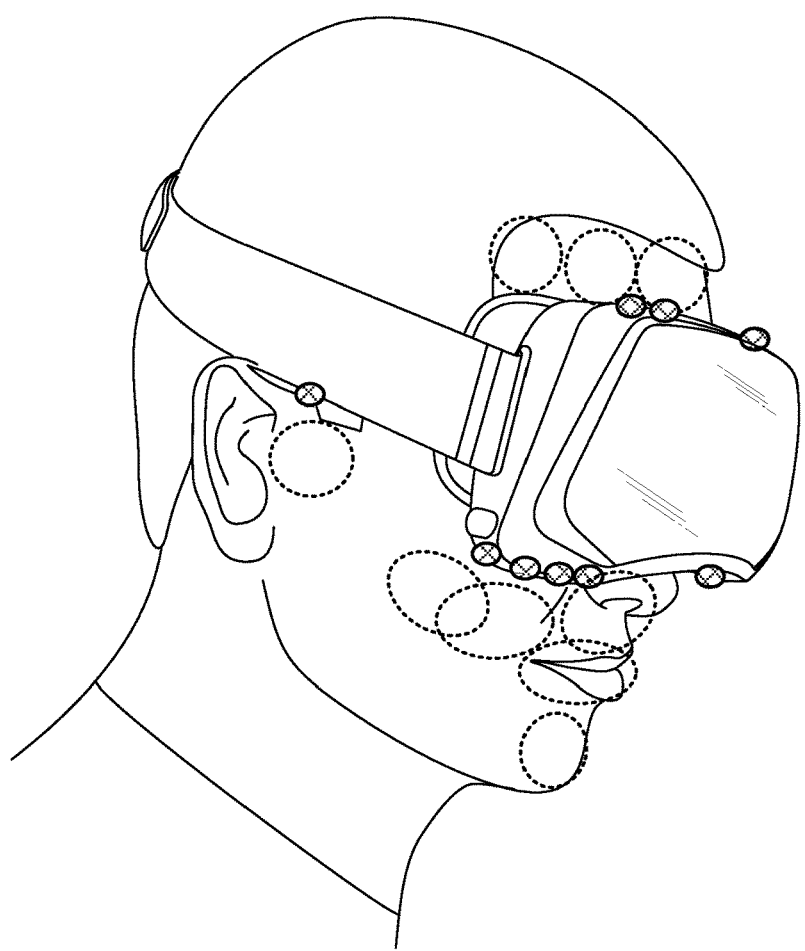

Referring to FIG. 2, the third thermal camera 22 and the fourth thermal camera 24 are physically coupled to the frame 26, at locations to the right and to the left of the symmetry axis, respectively, which are less than 15 cm away from the user's upper lip and below the first and second thermal cameras. The third thermal camera is configured to take thermal measurements of a third ROI ($TH_{ROI3}$), where $ROI_3$ 23 covers at least a portion of the user's right upper lip. The fourth thermal camera is configured to take thermal measurements of a fourth ROI ($TH_{ROI4}$), where $ROI_4$ 25 covers at least a portion of the user's left upper lip. Additionally, the third and fourth thermal cameras are located outside the exhale streams of the mouth and nostrils, and the thermal cameras are not in physical contact with their respective ROIs.

The system is configured to forward $TH_{ROI1}$, $TH_{ROI2}$, $TH_{ROI3}$, and $TH_{ROI4}$ to a processor configured to identify the physiological response. Optionally, the physiological response is indicative of an emotional state of the user. Optionally, the emotional state is indicative of an extent the user felt at least one of the following emotions: anger, disgust, fear, joy, sadness, and surprise. Additionally or alternatively, the physiological response may be indicative of a level of stress felt by the user. Additionally or alternatively, the physiological response may be indicative of an allergic reaction of the user. Additionally or alternatively, the physiological response may be indicative of a level of pain felt by the user.

In different embodiments, the ROIs mentioned above may cover slightly different regions on the user's face. In one embodiment, the overlap between $ROI_1$ and $ROI_2$ is below 50% of the smallest area from among the areas of $ROI_1$ and $ROI_2$, and the overlap between $ROI_3$ and $ROI_4$ is below 50% of the smallest area from among the areas of $ROI_3$ and $ROI_4$. In another embodiment, there is no overlap between $ROI_1$ and $ROI_2$, and there is no overlap between $ROI_3$ and $ROI_4$.

In one embodiment, the system described above may include a fifth thermal camera coupled to the frame, pointed at a fifth ROI ($ROI_5$), where $ROI_5$ covers at least a portion of the user's nose, and the fifth thermal camera is not in physical contact with $ROI_5$. In another embodiment, the system described above may include a fifth thermal camera coupled to the frame, pointed at a fifth ROI ($ROI_5$), where $ROI_5$ covers at least a portion of periorbital region of the user's face, and the fifth thermal camera is not in physical contact with $ROI_5$.

Some systems may include visible light cameras in addition to thermal cameras, as described in the following example. In one embodiment, a system configured to collect thermal and visible samples of a user's face from fixed relative positions includes at least a frame, a first thermal camera, a second thermal camera, and a visible light camera. The frame is configured to be worn on the user's head. The first thermal camera, the second thermal camera, and a visible light camera, are physically coupled to the frame. Furthermore, the thermal cameras and the visible light camera maintain fixed positioning relative to each other and relative to their corresponding ROIs when the user's head makes angular movements.

The first thermal camera is configured to take thermal measurements of a first region of interest ($TH_{ROI1}$), where $ROI_1$ covers at least part of the area around the user's eyes. The second thermal camera is configured to take thermal measurements of a second ROI ($TH_{ROI2}$), where $ROI_2$ covers at least part of the user's upper lip. The visible light camera is configured to take images of a third ROI ($IM_{ROI3}$), wherein $ROI_3$ covers at least part of the user's face.

In one embodiment, the system includes a processor configured to train a machine learning-based model for the user based on $TH_{ROI1}$ and $TH_{ROI2}$. Optionally, the model identifies an affective response of the user.

Herein, the term "visible light camera" refers to a camera designed to detect at least some of the visible spectrum. Examples of visible light sensors include active pixel sensors in complementary metal-oxide-semiconductor (CMOS), and semiconductor charge-coupled devices (CCD).

Following are some examples of systems that utilize thermal cameras for various applications.

FIG. 5 illustrates one embodiment of a wearable system, such as a head mounted system (HMS), configured to estimate a stress level. The system includes a frame, a thermal camera and circuit. The frame is configured to be worn on a user's head. The thermal camera is physically coupled to the frame at a position that is less than 15 cm away from one of the user's eyes, not in physical contact with the eye, and is configured to take thermal measurements of a region of interest ($TH_{ROI}$), where the ROI covers at least part of a periorbital region of the user's eye. Locations 52, 53, and 54 in FIG. 5 illustrate possible positions for locating tiny thermal cameras for measuring the periorbital region around the right eye. The circuit 56, which may by wearable by the user or non-wearable, is configured to estimate the stress level of the user based on changes to temperature of the periorbital region received from the thermal camera. Optionally, the stress level relates to a stressful event, the delay between a stressful event and its representation on the at least part of the periorbital region is less than one minute, and most of the representation diminished within less than five minutes after the stressful event is over.

In one embodiment, the system described above includes an eye-tracking module coupled to the frame, which is configured to track gaze of the user. The wearable system is an optical see through head mounted display configured to operate in cooperation with a second camera configured to capture images of objects the user is looking at, and with a processor configured to match the objects the user is looking at with the stress levels inferred from the thermal measurements.

In one embodiment, the system described above includes a display that is coupled to the frame and is configured to present video comprising objects, and an eye-tracking module coupled to the frame and configured to track gaze of the user. The wearable system is configured to operate in cooperation with a processor configured to match the objects the user is looking at with the stress levels inferred from the thermal measurements.

Figure 8:
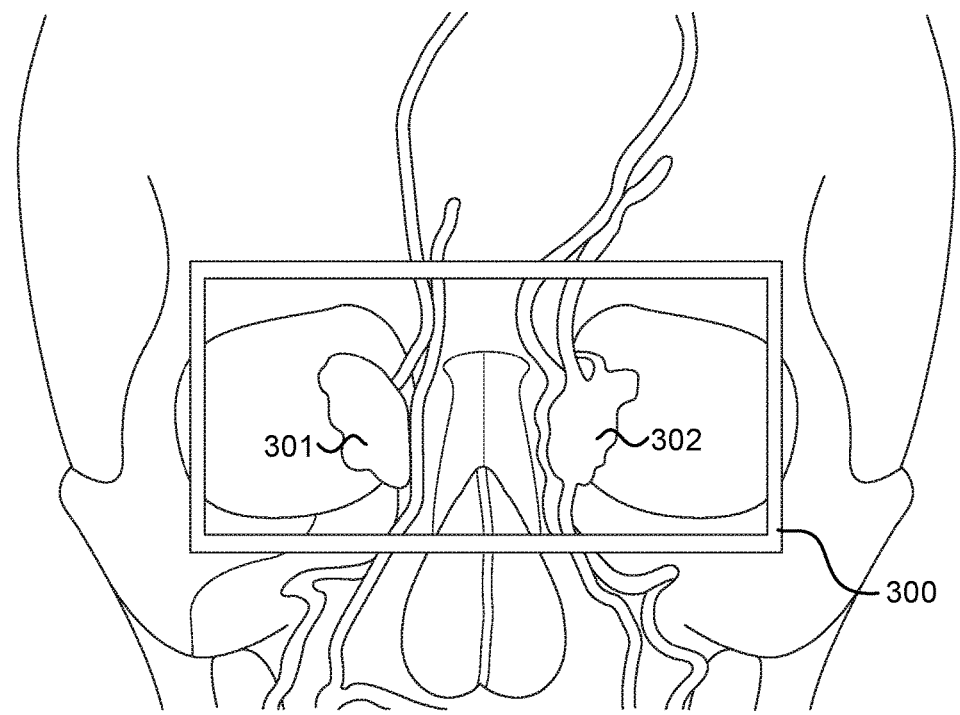
FIG. 8 illustrates the periorbital ROI.

The periorbital region of the user's face is discussed, for example, in the reference Tsiamyrtzis, P., Dowdall, J., Shastri, D., Pavlidis, I. T., Frank, M. G., & Ekman, P. (2007), "Imaging facial physiology for the detection of deceit", International Journal of Computer Vision, 71(2), 197-214. FIG. 8 illustrates the periorbital ROI, schematically represented by rectangle 300. Regions 301 and 302, referred to as the conduits in the eye corners, schematically represent about 10% of the hottest area within the periorbital ROI that may be sufficient to detect the "fight or flight" response during stress (also known as fight or flight syndrome).

The reference Pavlidis, I., Levine, J., & Baukol, P. (2000), "Thermal imaging for anxiety detection", In Computer Vision Beyond the Visible Spectrum: Methods and Applications, 2000. Proceedings. IEEE Workshop on (pp. 104-109). IEEE, also shows the periorbital region, together with the nasal area, right and left cheeks, chin area, and the neck area.

In another embodiment, a system configured to estimate a level of the fight or flight response of a user wearing a head mounted system (HMS) includes at least a frame, a thermal camera, and a circuit. The frame is configured to be worn on the head of the user. The thermal camera is physically coupled to the frame at a position that is less than 15 cm away from one of the user's eyes, is not in physical contact with the eye, and is configured to take thermal measurements of a region of interest ($TH_{ROI}$), wherein the ROI covers at least part of a periorbital region of the user's eye. The circuit is configured to estimate the level of fight or flight response of the user based on $TH_{ROI}$.

In one embodiment, the system described above includes a user interface configured to notify the user when the level of fight or flight response reaches a predetermined threshold. Optionally, the user interface utilizes at least one of an audio indication and visual indication to notify the user.

In one embodiment, the system described above includes: a display configured to show the user a video comprising objects, and a documenting module configured to save the estimated level of fight or flight response associated with the viewed objects.

In yet another embodiment, a system configured to estimate stress level of a user wearing a head mounted system (HMS) includes a frame, a thermal camera, and a circuit. The frame is configured to be worn on the head of the user. The thermal camera, which is physically coupled to the frame at a position that is less than 15 cm away from the tip of the user's nose, is configured to take thermal measurements of a region of interest ($TH_{ROI}$), wherein the ROI covers at least part of the area around the user's nose. Optionally, the thermal camera is based on at least one of: a thermopile sensor, and a pyroelectric sensor. One example of the region of interest around the nostrils is described in the reference Shastri, D., Papadakis, M., Tsiamyrtzis, P., Bass, B., & Pavlidis, I. (2012), "Perinasal imaging of physiological stress and its affective potential", Affective Computing, IEEE Transactions on, 3(3), 366-378. The circuit is configured to estimate the stress level based on $TH_{ROI}$.

In one embodiment, the system described above also includes a biofeedback mechanism configured to alert the user when the stress level reaches a predetermined threshold.

In still another embodiment, a wearable system configured to estimate a physiological response of a user includes a frame, first and second thermal cameras, and a circuit. The frame is configured to be worn on the head of the user. The first and second thermal cameras, physically coupled to the frame at positions that are less than 20 cm away from the user's forehead. The first thermal camera is configured to take thermal measurements of a first region of interest ($TH_{ROI1}$), where $ROI_1$ covers at least part of the right side of the user's forehead. The second thermal camera is configured to take thermal measurements of a second ROI ($TH_{ROI2}$), where $ROI_2$ covers at least part of the left side of the user's forehead. The circuit is configured to estimate the physiological response of the user based on $TH_{ROI1}$ and $TH_{ROI2}$. Optionally, THROI1 and THROI2 are correlated with blood flow in the frontal vessel of the user's forehead. Optionally, the physiological response is mental stress and the circuit is further configured to estimate frontal blood flow based on $TH_{ROI}$, which is indicative of mental stress. Optionally, the circuit is further configured to estimate periorbital perfusion based on $TH_{ROI}$, which is indicative of fight or flight response.

In one embodiment, the system described above includes a biofeedback mechanism configured to alert the user when the stress level reaches a predetermined threshold.

A head-mounted system (HMS) may utilize a thermal camera to estimate how a user feels towards digital content presented to the user, as the following example shows. Herein, "digital content" refers to any type of content that can be stored in a computer and presented by the computer to a use.

In one embodiment, a system configured to take thermal measurements of a user wearing a head mounted display (HMD) includes a display, a thermal camera, and a circuit. The display, which is worn by the user (e.g., it is attached to a frame of the HMS), is configured to present digital content to the user. The thermal camera, which is physically coupled to the HMD, is configured to take thermal measurements of a region of interest ($TH_{ROI}$) on the user's face; the thermal camera is not in physical contact with the ROI, and remains pointed at the ROI when the user's head makes angular movements. The circuit is configured to estimate affective response of the user to the digital content based on $TH_{ROI}$.

In one embodiment, the affective response is stress, the ROI covers at least part of the periorbital region of the user's face, and the greater the change in the ROI temperature the higher the stress level of the user. In another embodiment, the affective response is stress, the ROI covers at least part of the user's nose, and the magnitude of the stress is proportional to the change in the ROI temperature. In yet another embodiment, a value, from among $TH_{ROI}$, reaching a threshold is indicative of the affective response. In still another embodiment, at least one feature value utilized by a predictor that predicts occurrences of the affective response is based on $TH_{ROI}$.

In one embodiment, the system described above includes a computer configured to change the digital content presented to the user based on the estimated affective response.

In one embodiment, the thermal camera measures temperature at the ROI, and the system's nominal measurement error of the temperature at the ROI ($ERR_{TROI}$) is at least twice the system's nominal measurement error of the temperature change at the ROI ($ERR_{ATROI}$) when the user's head makes angular movements above 0.02 rad/sec. Additionally, wherein the circuit is able to identify affective response causing a temperature change at the ROI which is below $ERR_{TROI}$ and above $ERR_{ATROI}$.

In another embodiment, the thermal camera measures temperature at the ROI, and the system's nominal measurement error of the temperature at the ROI ($ERR_{TROI}$) is at least five times the system's nominal measurement error of the temperature change at the ROI ($ERR_{ATROI}$) when the user's head makes angular movements above 0.1 rad/sec. Additionally, the circuit is able to identify affective response causing a temperature change at the ROI which is below $ERR_{TROI}$ and above $ERR_{ATROI}$.

Alertness, anxiety, and even fear appear to accompany people that are involved in illegal activities at the time of their action. Since those symptoms are produced by the sympathetic system, they cannot be totally controlled, and thus constitute a powerful biometric that is difficult to conceal. This biometric can provide valuable clues to security systems of critical/sensitive facilities/data about potential suspects immune to identification biometrics, such as first time offenders.

When a user experiences elevated feelings of alertness, anxiety, or fear, increased levels of adrenaline regulate blood flow. Redistribution of blood flow in superficial blood vessels causes abrupt changes in local skin temperature that is readily apparent in the user's face where the layer of flesh is very thin. The human face and body emit both in the mid-infrared (3-5 µm) and far-infrared (8-12 µm) bands, thus mid-infrared and far-infrared thermal sensors can sense this temperature variations in the face and trigger a process for detecting the illegal activity.

Following is a description of a security system designed to utilize thermal measurements of a user's face in order to detect irregular activity. In one embodiment, the user is permitted to access sensitive data only through an HMD equipped with a thermal camera that measures temperature variations on the user's face while he/she is accessing the sensitive data. This way the user is under surveillance each time he/she is accessing the sensitive data, and optionally there is no way for the user to access the sensitive data without being monitored by the security system.

In one embodiment, the security system configured to detect an irregular activity includes a head mounted display (HMD) that includes: a frame, a display module, and a thermal camera. The thermal camera is configured to take thermal measurements of a region of interest ($TH_{ROI}$) on the user's face; the thermal camera is not in physical contact with the ROI and remains pointed at the ROI when the user's head makes angular movements. Optionally, the ROI covers at least part of periorbital region of the user's face. Optionally, the thermal camera comprises an uncooled thermal sensor.

A circuit (e.g., a processor) is configured to calculate a baseline thermal profile for the user based on readings of $TH_{ROI}$ taken while the user watches baseline sensitive data presented on the display module. The circuit is further configured to calculate a certain thermal profile for the user based on readings of $TH_{ROI}$ taken while the user watches a certain sensitive data presented on the display module, and issue an alert when the difference between the certain thermal profile and the baseline thermal profile reaches a predetermined threshold.

In one embodiment, $TH_{ROI}$ is expressed as temperature at the ROI, and the baseline thermal profile expresses ordinary temperature at the ROI while the user is exposed to sensitive data. In another embodiment, $TH_{ROI}$ is expressed as temperature change at the ROI, and the baseline thermal profile expresses ordinary temperature changes at the ROI around the time of switching from being exposed to non-sensitive data to being exposed to sensitive data. In still another embodiment, $TH_{ROI}$ is expressed as temperature change at the ROI, and the baseline thermal profile expresses ordinary temperature change at the ROI around the time of switching from being exposed to sensitive data to being exposed to non-sensitive data.

In one embodiment, the alert relates to detection of an illegal activity. Optionally, the delay between the time of performing the illegal activity and the time of reaching the predetermined threshold is less than two minutes.

In another embodiment, the security system utilizes the alert to estimate job burnout; the greater the difference between the certain thermal profile and the baseline thermal profile the worse is the job burnout.

In one embodiment, the user watches the certain sensitive data within less than 15 minutes before or after watching the baseline sensitive data. In some cases, it may be useful to compare close events because the shorter the time between watching the baseline sensitive data and watching the certain sensitive data, the smaller the negative effect of environmental changes and normal physiological changes may be. In one example, the user watches the certain sensitive data immediately before and/or after watching the baseline sensitive data. In another example, the user watches the certain sensitive data within less than 5 minutes before and/or after watching the baseline sensitive data.

When the user observes data over period of time, in some embodiments, each segment of data (e.g., data observed during a certain span of a few minutes) may serve both as a baseline sensitive data (for a certain evaluation) and as the certain sensitive data (for another evaluation).

In one embodiment, the circuit is further configured to receive characteristics of the environment the user is in while watching the certain sensitive data, and further configured to select for the baseline an event where the user watched the baseline sensitive data while being in a similar environment. In one example, the difference in ambient temperatures of similar environments is less than 2 degrees. In another example, the difference in humidity of similar environments is less than 5 percent. In still another example, the difference in oxygen percent in the air of similar environments is less than 2 percent.

In one embodiment, the security system further detects that the user moved the HMD while being exposed to the certain sensitive data, and therefore does not allow the user to perform a certain transaction related to the certain sensitive data. In one example, the certain transaction comprises at least one of the following: copying, reading, and modifying the certain sensitive data. In another example, the certain sensitive data relates to money, and the certain transaction comprises electronic funds transfer from one person or entity to another person or entity.

In another embodiment, the security system further detects that the user moved the HMD while being exposed to the certain sensitive data, and marks the relationship between the user and the certain sensitive data as being suspicious. Optionally, the security system issues a security alert after detecting that the user moved again the HMS while being exposed to another sensitive data that is of the same type as the certain sensitive data.

Figure 12:
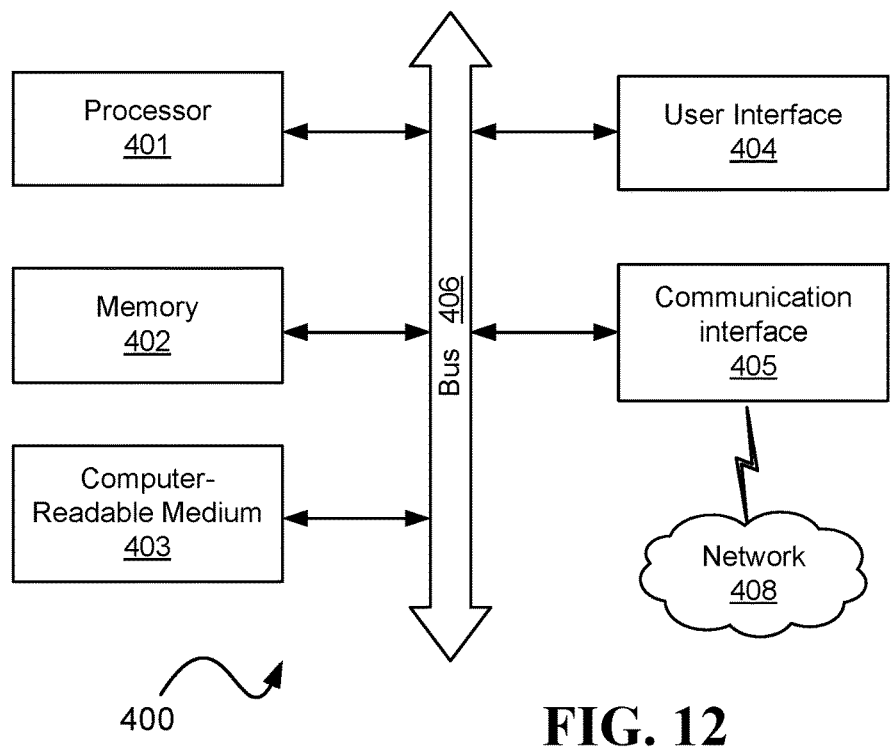
FIG. 12 is a schematic illustration of a computer able to realize one or more of the embodiments discussed herein.

FIG. 12 is a schematic illustration of a computer 400 that is able to realize one or more of the embodiments discussed herein. The computer 400 may be implemented in various ways, such as, but not limited to, a server, a client, a personal computer, a set-top box (STB), a network device, a handheld device (e.g., a smartphone), computing devices embedded in wearable devices (e.g., a smartwatch or a computer embedded in clothing), computing devices implanted in the human body, and/or any other computer form capable of executing a set of computer instructions. Further, references to a computer include any collection of one or more computers that individually or jointly execute one or more sets of computer instructions to perform any one or more of the disclosed embodiments.

The computer 400 includes one or more of the following components: processor 401, memory 402, computer readable medium 403, user interface 404, communication interface 405, and bus 406. In one example, the processor 401 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 402 may include one or more of the following memory components: CPU cache, main memory, read-only memory (ROM), dynamic random access memory (DRAM) such as synchronous DRAM (SDRAM), flash memory, static random access memory (SRAM), and/or a data storage device. The processor 401 and the one or more memory components may communicate with each other via a bus, such as bus 406.

Still continuing the example, the communication interface 405 may include one or more components for connecting to one or more of the following: LAN, Ethernet, intranet, the Internet, a fiber communication network, a wired communication network, and/or a wireless communication network. Optionally, the communication interface 405 is used to connect with the network 408. Additionally or alternatively, the communication interface 405 may be used to connect to other networks and/or other communication interfaces. Still continuing the example, the user interface 404 may include one or more of the following components: (i) an image generation device, such as a video display, an augmented reality system, a virtual reality system, and/or a mixed reality system, (ii) an audio generation device, such as one or more speakers, (iii) an input device, such as a keyboard, a mouse, a gesture based input device that may be active or passive, and/or a brain-computer interface.

At least some of the methods described in this disclosure, which may also be referred to as "computer-implemented methods", are implemented on a computer, such as the computer 400. When implementing a method from among the at least some of the methods, at least some of the steps belonging to the method are performed by the processor 401 by executing instructions. Additionally, at least some of the instructions for running methods described in this disclosure and/or for implementing systems described in this disclosure may be stored on a non-transitory computer-readable medium.

In one embodiment, a head mounted system (HMS) configured to collect facial expressions of a user wearing the HMS, comprising: a frame configured to be worn on the user's head; first and second cameras coupled to the frame, at locations to the right and to the left of the symmetry axis that divides the face to the right and left sides, respectively, which are less than 15 cm away from the user's right and left pupils, respectively; the first and second cameras are oriented such that the user's right and left eyebrows are in the fields of view (FOVs) of the first and second cameras, respectively, and the user's left and right oral commissures are not in the FOVs of the first and second cameras, respectively; third and fourth cameras coupled to the frame, at locations to the right and to the left of the symmetry axis, respectively, and less than 15 cm away from the user's upper lip; the third and fourth cameras are oriented such that the user's right and left upper lips are in the FOVs of the third and fourth cameras, respectively, and the user's left and right eyebrows are not in the FOVs of the third and fourth cameras, respectively; and wherein the location and orientation of the first, second, third and fourth cameras relative to the user's head do not change even when the user's head performs wide angular movements.

Optionally, the facial expressions are microexpressions, and at least one of the cameras is configured to have at least a portion of the user's right cheek in its FOV, and that portion of the user's right cheek enables a microexpression analyzer to identify a right cheek raiser. Optionally, at least one of the cameras is configured to have at least a portion of the user's left cheek in its FOV, and that portion of the user's left cheek enables a microexpression analyzer to identify a left cheek raiser. Optionally, at least one of the cameras is configured to have at least a portion of the user's chin cheek in its FOV, and that portion of the user's chin enables a microexpression analyzer to identify a chin raiser.

Optionally, the facial expressions are microexpressions, and further comprising a processor configured to extract vision-related features from data derived from images captured by the first and second cameras, and to utilize a machine learning trained classifier to identify a microexpression expressed by the user; wherein the machine learning trained classifier is trained to identify microexpression relates to the upper part of the face from vision-related features identified from images captured by the first and second cameras. Optionally, the data is derived from first and second video streams received from the first and second cameras; and wherein the vision-related features comprise temporal features. Optionally, the first and second cameras capture in high resolution and high frame rate. Optionally, the HMS further includes deriving vision-related features from locations of facial landmarks identified in the first and second images. Optionally, the HMS further includes a processor configured to extract vision-related features from data derived from images captured by the third and fourth cameras, and utilize a machine learning trained classifier to identify a microexpression expressed by the user; wherein the machine learning trained classifier is trained to identify microexpression relates to the lower part of the face from vision-related features identified from images captured by the third and fourth cameras. Optionally, the third and fourth cameras capture in high resolution and high frame rate. Optionally, comprising deriving vision-related features from locations of facial landmarks identified in the third and fourth images.

In some embodiments, facial cues refer to facial expressions and/or physiological signals that can be measured over certain parts of the face. In one embodiment, the cameras are coupled to the HMS, and at least one of the cameras does not have a line of sight to capture an image of the entire wearer's face, and in some cases the angle between the optical axis of at least one of the cameras and the Frankfort horizontal plane is greater than 20 degrees.

Figure 13:
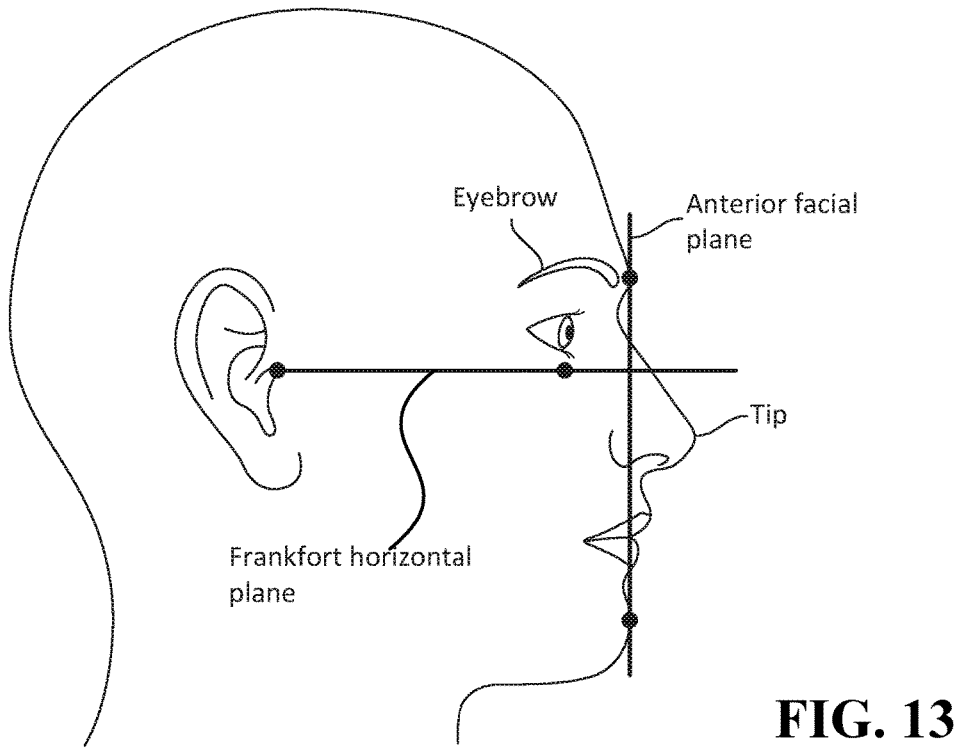
FIG. 13 illustrates the Frankfort horizontal plane and anterior facial plane.

FIG. 13 illustrates the Frankfort horizontal plane and anterior facial plane as used herein. A line from the superior aspect of the external auditory canal to the most inferior point of the orbital rim creates the Frankfort horizontal plane (known also as the Frankfurt horizontal plane or Frankfort plane). A line from the glabella to pogonion creates the anterior facial plane.

Figure 14:
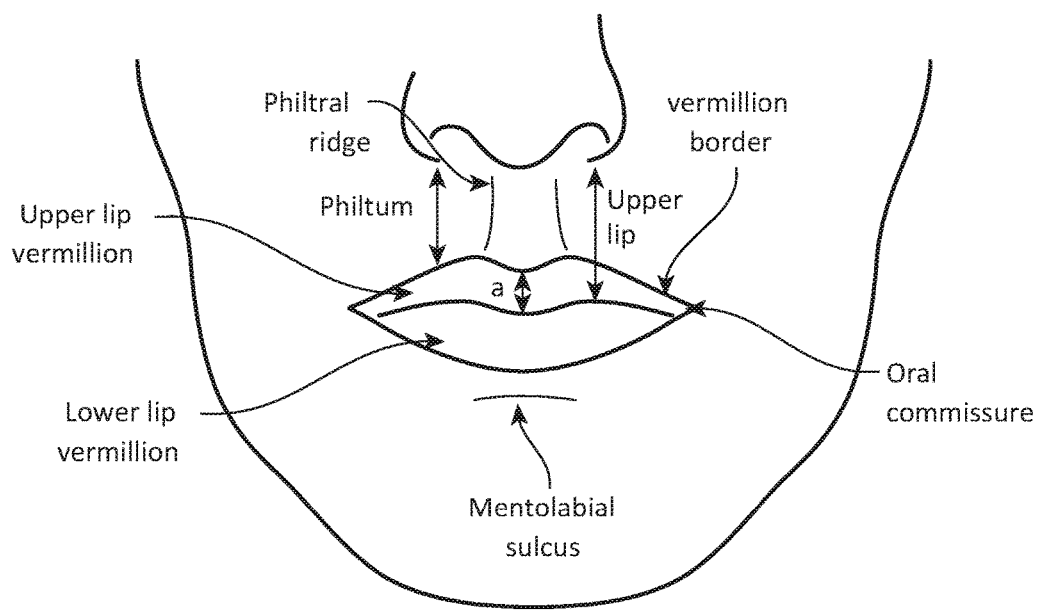
FIG. 14 illustrates the upper lip, upper lip vermillion, lower lip vermillion, and the oral commissure that is the place where the lateral aspects of the vermilion of the upper and lower lips join.

FIG. 14 illustrates the upper lip, upper lip vermillion, lower lip vermillion, and the oral commissure that is the place where the lateral aspects of the vermilion of the upper and lower lips join.

It is noted that all measurements, notations, planes, angles, distances, horizontal facial thirds, and/or elements of the user's face (such as eyes, nose, lips, eyebrows, hairline) herein refer to a normal, 20 years old, aesthetic human, such as described in Chapter 2, Facial Proportions, by Peter M. Prendergast, in the book "Advanced Surgical Facial Rejuvenation, Art and Clinical Practice", Editors: Erian, Anthony, Shiffman, Melvin A., Publisher: Springer-Verlag Berlin Heidelberg, 2012. It is further noted that the appearance of the face varies with facial movement, thus, the positions of the elements of the user's face (such as eyes, nose, lips, eyebrows, hairline) are assessed herein when the user has a relaxed (neutral) face: the eyes are open, the lips make gentle contact, and the teeth are slightly separated. The neck, jaw, and facial muscles are not stretched nor contracted, and the face is positioned using the Frankfort horizontal plane.

Figure 15:
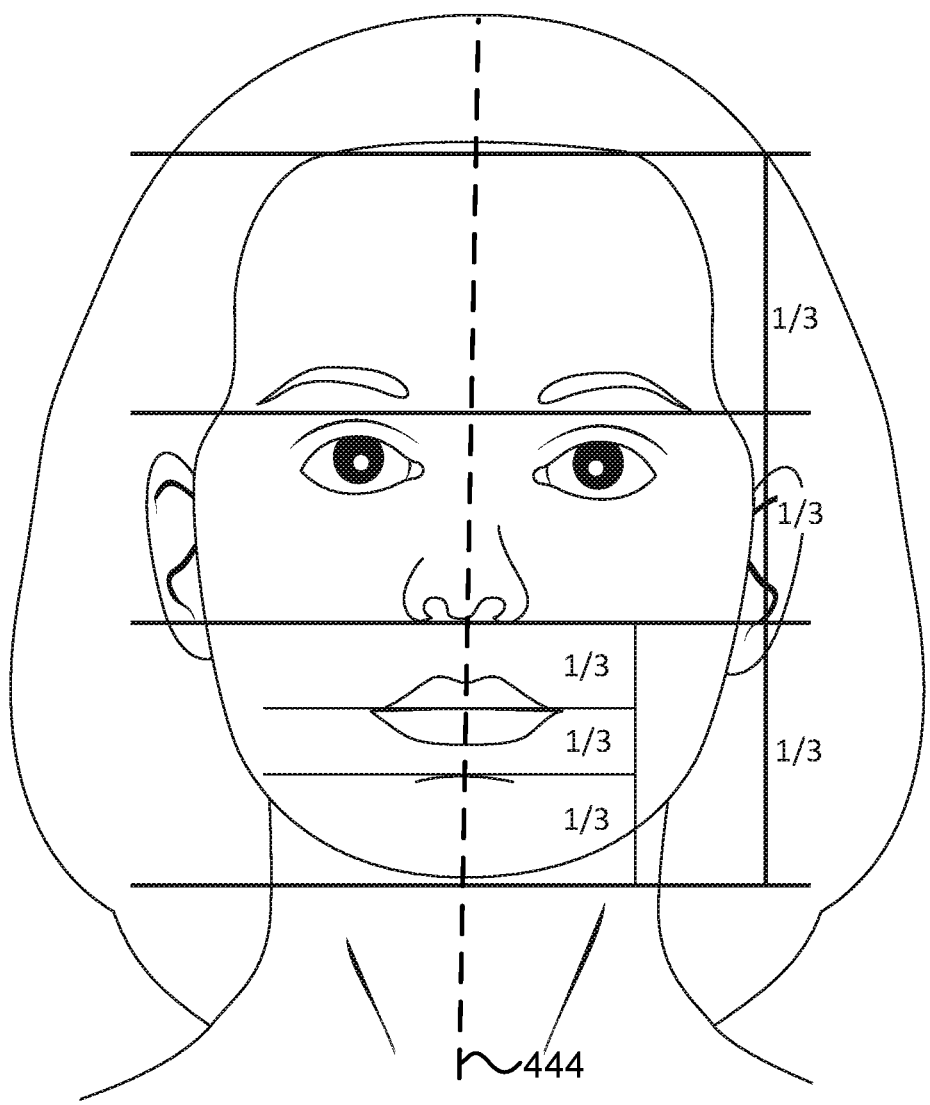
FIG. 15 illustrates the horizontal facial thirds.

FIG. 15 illustrates the horizontal facial thirds. The upper horizontal facial third extends from the hairline to glabella, the middle horizontal facial third extends from glabella to subnasale, and lower horizontal facial third extends from subnasale to menton. The lower horizontal facial third is further divided into thirds: the lower-upper horizontal facial third extends from subnasale to stomion (defines the upper lip), the lower-middle horizontal facial third extends from stomion to the labiomental crease (defines the lower lip), and the lower-lower horizontal facial third extends from the labiomental crease to menton (defines the chin). It is noted that the thirds are not equal. It is further noted that 100% of area referred to herein is determined by the parts visible to a front facing camera (in a similar manner to FIG. 15). Symmetry axis 444 divides the face to the right and left sides.

It is further noted that an object is not in the FOV of a camera when it is not located in the angle of view of the camera and/or when there is no line of sight from the camera to the object, where "line of sight" is interpreted in the context of the spectral bandwidth of the camera.

In one example, "a frame configured to be worn on the head of the user" is interpreted as a frame that loads more than 50% of its weight on the user's head. For example, the frame in Oculus Rift and HTC Vive is the foam placed on the user's face and the straps; the frame in Microsoft HoloLens is the adjustment wheel in the headband placed on the user's head.

In one example, wide angular movements are interpreted as angular movements of more than 45 degrees.

In one example, the locations of the first and second cameras relative to the user's head do not change even when the user's head performs wide angular and lateral movements, wherein wide angular and lateral movements are interpreted as angular movements of more than 60 degrees and lateral movements of more than 1 meter.

The orientation of the camera influences its FOV. For example, a camera may be coupled to the top portion of a virtual reality (VR) headset faceplate at location and orientation directed towards the wearer of the VR headset, or coupled to the top portion of the VR headset faceplate at essentially the same location but with a different orientation that is directed towards another person standing in front of the wearer.

Optionally, the FOV of the first camera include the right forehead of the user, which may be regarded as the area located over at least some of the right corrugator supercilii muscle and at least some of the occipitofrontalis muscle.

In one example, phrases in the form of "a location to the right of the symmetry axis that divides the face to the right and left sides" may be interpreted as at least 1 cm, 2 cm, 3 cm, 5 cm, 7 cm, 9 cm, 12 cm, or 15 cm right of the symmetry axis.

{Sharp Capturing Angle}

Optionally, the angle between the optical axis of the first camera and the Frankfort horizontal plane is greater than 20 degrees. In one example, the angle between the optical axis of the second camera and the Frankfort horizontal plane is also greater than 20 degrees. In another example, the angles between the optical axes of the first and second cameras and the Frankfort horizontal plane are greater than 30 degrees, respectively. In still another example, the angles between the optical axes of the first and second cameras and the Frankfort horizontal plane are greater than 45 degrees, respectively. In still another example, the angles between the optical axes of the first and second cameras and the Frankfort horizontal plane are greater than 60 degrees, respectively.

It is noted that phrases in the form of "the angle between the optical axis of the camera and the Frankfort horizontal plane is greater than 20 degrees" refer to absolute values (which may take +20 or −20 in this example) and are not limited to just positive or negative angles, unless specifically indicated such as in a phrase having the form of "the optical axis of the camera points at least 20 degrees below the Frankfort horizontal plane" where it is clearly indicated that the camera is pointed downwards.

Optionally, the angle between the optical axis of the third camera and the Frankfort horizontal plane is greater than 20 degrees. Optionally, the angle between the optical axis of the fourth camera and the Frankfort horizontal plane is greater than 20 degrees. In one example, the angles between the optical axes of the third and fourth cameras and the Frankfort horizontal plane are greater than 30 degrees, respectively. In another example, the angles between the optical axes of the third and fourth cameras and the Frankfort horizontal plane are greater than 45 degrees, respectively.

Optionally, the HMS further includes a fifth camera coupled to the frame at a location that is less than 10 cm away from the user's right pupil; the fifth camera is oriented such that the lower orbital part of the user's orbicularis oculi muscle that surrounds the user's right eye is in the FOV of the fifth camera, and the user's left oral commissure is not in the FOV of the fifth camera; wherein the location and orientation of the fifth camera relative to the user's head does not change even when the user's head performs wide angular movements. In one example, the upper orbital part of the user's right side orbicularis oculi muscle is also in the FOV of the fifth camera. In another example, the distance between the fifth camera and the right lower orbital part is below 5 cm.

In one example, the HMS further includes a sixth camera coupled to the frame at a location that is less than 10 cm away from the user's left pupil; the sixth camera is oriented such that the lower orbital part of the user's orbicularis oculi muscle that surrounds the user's left eye is in the FOV of the sixth camera, and the user's right oral commissure is not in the FOV of the sixth camera; wherein the location and orientation of the sixth camera relative to the user's head does not change even when the user's head performs wide angular movements. Optionally, the image captured by the sixth camera further includes the upper orbital part of the user's left side orbicularis oculi muscle.

Common VR headsets are quite sealed to ambient light. Something there is light from the display, and something there is no. Moreover, the light from the display changes, which make it harder to capture facial expressions within the occluded area. Therefore, in one embodiment an IR light sources (e.g., IR LEDs) are add inside the headset, and the periorbital camera does not have an IR filer. Optionally, the periorbital camera captures only near IR waves so that visible light from the display does not interfere.

In one example, the frame is similar to extending side arms of eyeglasses. The frame may be positioned behind a user's ears to secure the HMS to the user. The frame may further secure the HMS to the user by extending around a rear portion of the user's head. Additionally or alternatively, the frame may connect to or be affixed within a head-mountable helmet structure.

The positions of the cameras on the figures are just for illustration. The cameras may be placed at other positions on the HMS. One of more of the cameras may be configured to capture images at various resolutions or at different frame rates. Many video cameras with a small form-factor, such as those used in cell phones or webcams, for example, may be incorporated into some of the embodiments.

Further, illustrations and discussions of a camera represent one of more cameras, where each camera may be configured to capture the same view, and/or to capture different views. In one embodiment, one of more of the cameras may include one or more elements, such as a gyroscope, an accelerometer, and/or a proximity sensor. Other sensing devices may be included within the camera, and/or in addition to the camera, and other sensing functions may be performed by one or more of the cameras.

In one embodiment, because facial structures generally differ from user to user, the HMS may calibrate the direction, position, algorithms, and/or characteristics of one or more of the cameras and/or light sources based on the facial structure of the user. In one example, the HMS calibrates the positioning of a camera in relation to a certain feature on the user's face. In another example, the HMS changes, mechanically and/or optically, the positioning of a camera in relation to the frame in order to adapt itself to a certain facial structure.

Optionally, the HMS further includes a display coupled to the frame and configured to present digital content to the user. Herein, phrases in the form of "a display coupled to the frame" are to be interpreted as one or more of the following: (i) the frame can be worn and/or take off together with the display such that when the user wears/takes off the helmet he/she also wears/takes off the display, (ii) the display is integrated with the frame, and optionally the display is sold together with the HMS, and/or (iii) the HMS and the display share at least one electronic element, such as a processor, a memory, a battery, an optical element, and/or a communication unit for communicating with a non-head mounted computer.

Optionally, the HMS further includes a helmet coupled to the frame and configured to protect the user's scalp; wherein the helmet is selected from the group of: a sport helmet, a motorcycle helmet, a bicycle helmet, and a combat helmet. Herein, phrases in the form of "a helmet coupled to the frame" are to be interpreted as one or more of the following: (i) the frame can be worn and/or take off together with the helmet such that when the user wears/takes off the helmet he/she also wears/takes off the HMS, (ii) the frame is integrated with the helmet and/or the helmet itself forms the frame, and optionally the HMS is sold together with the helmet, and/or (iii) the HMS and the helmet share at least one electronic element, such as an inertial measurement sensor, a processor, a memory, a battery, an image sensor, and/or a communication unit for communicating with a non-head mounted computer.

Optionally, the HMS further includes a brainwave headset coupled to the frame and configured to collect brainwave signals of the user. Herein, phrases in the form of "a brainwave headset coupled to the frame" are to be interpreted as one or more of the following: (i) the frame can be worn and/or take off together with the brainwave headset such that when the user wears/takes off the brainwave headset he/she also wears/takes off the HMS, (ii) the frame is integrated with the brainwave headset and/or the brainwave headset itself forms the frame, and optionally the HMS is sold together with the brainwave headset, and/or (iii) the HMS and the brainwave headset share at least one electronic element, such as an inertial measurement sensor, a processor, a memory, a battery, and/or a communication unit.

Optionally, at least one of the inward facing cameras is a depth camera that detects distances of items relative to the camera. Optionally, the depth camera is selected from the group comprising at least one of: a light field camera, a camera with active illumination, and a camera array. Optionally, the first camera features an extended depth of field that can capture in focus objects that are 2 to 5 cm from the first camera. Optionally, the first camera operates according to Scheimpflug principle in order to achieve an extended depth of field (DOF). Optionally, the first camera further comprises an autofocus mechanism configured to tilt and/or rotate the sensor and/or optics to obtain the extended DOF. Optionally, the first camera is a light field camera. Optionally, the first camera utilizes at least one of the following techniques to achieve an extended depth of field: wavefront coding, diffusion coding, coded aperture, multiple apertures, and lens array.

Optionally, the HMS further includes a structured light pattern projector; wherein the first camera is configured to capture a distorted pattern of the reflected structured light. Optionally, the structured light pattern projector transmits in wavelength longer than 700 nm. Optionally, the HMS further includes a processor configured to calculate at least one of depth and movement from the captured distorted pattern in order to identify the facial cues.

Optionally, the HMS further includes an eye tracker configured to track gaze of the user in order to enable identification of an object the user is looking at; and further comprising a communication module configured to send an indication of the object and a facial cue derived from at least one of the first and second cameras; wherein the indication and the facial cue enable association of the object with an affective response of the user. Optionally, the HMS further includes a display coupled to the frame and configured to present digital content to the user, and the object is presented by the display. Optionally, the HMS further includes an optical-see-through display coupled to the frame and configured to present digital content to the user, and the object is a real world object.

Optionally, the HMS further includes an eye tracker and a processor; the eye tracker is configured to track gaze of the user in order to identify an object the user is looking at; the processor is configured to decode a facial expression of the user based on data received from at least one of the first and second cameras, and to associate the decoded facial expression with the object. Optionally, the HMS further includes a display coupled to the frame and configured to present digital content to the user, and the object is presented by the display. Optionally, the HMS further includes an optical-see-through display coupled to the frame and configured to present digital content to the user, and the object is a real world object.

Optionally, one or more of the cameras comprise a sensor configured to detect radiation in the visible spectrum. Optionally, the facial cues comprise facial expressions.

Optionally, one or more of the cameras comprise a sensor configured to detect radiation in the infrared spectrum. Optionally, the facial cues comprise changes to the temperature over time of a region of interest on the face.

Optionally, the HMS further includes a facial expression decoder configured to decode a facial expression of the user based on data received from at least one of the first and second cameras. Optionally, the received data is detailed and frequent enough to enable the facial expression decoder to decode a microexpression.

Optionally, the HMS further includes a wireless transceiver configured to connect the HNS with a computer that is not carried by the user; and further comprising a facial expression compressor configured to receive the pictures from the first and second cameras, extract points of interest that represent movements of the eyebrows, wherein storing the points of interest requires less than 10% of the storage required to store the pictures from the first and second cameras, and transmitting the points of interest to the computer.

Optionally, the HMS further includes a display and a controller; the display is coupled to the frame and configured to present digital content to the user; wherein the controller is configures to command the first and second cameras to capture images at a higher rate when the display presents an object that is expected to cause the user to have a noticeable emotional response, compared to the rate of capturing images by the first and second cameras when the display presents an object that is not expected to cause the user to have a noticeable emotional response.

In one example, one or more of the cameras includes a field splitter, which is a camera lens configured as a prism. A field splitter delivers multiple fields of view in a single camera lens such that a stereo vision can be achieved without multiple cameras. A field splitter may be useful for one of more of the following: machine vision applications, splitting the captured rays into two images to get a stereo view from a single camera, adjusting over a range of motion without changing the optical path length, allowing a single camera to view multiple fields at once, viewing the same field from multiple directions, and/or reducing the number of head-mounted cameras as fewer cameras may be used to achieve the same number of views.

In one embodiment, a method for identifying facial expressions of a user wearing a head mounted system (HMS), includes the following steps: receiving first and second video streams from first and second cameras, respectively; the cameras are pointed at the user and are coupled to the HMS at locations that do not change relative to the user's head even when the user's head performs wide angular movements; wherein the user's right and left eyebrows are in the fields of view (FOVs) of the first and second cameras, respectively, and the user's left and right oral commissures are not in the FOVs of the first and second cameras, respectively; and identifying facial expressions related to the upper part of the user's face based on a model for extracting facial expressions from data comprising the first and second video streams.

Optionally, the method further includes receiving third and fourth video streams from third and fourth cameras pointed at the user and are coupled to the HMS at locations that do not change relative to the user's head even when the user's head performs wide angular movements; wherein the user's right and left upper lips are in the FOVs of the third and fourth cameras, and the user's left and right eyebrows are not in the FOVs of the third and fourth cameras; and identifying facial expressions related to the lower part of the user's face based on a model for extracting facial expressions from data comprising the third and fourth video streams.

Optionally, the facial expressions are microexpressions, and the model for extracting facial expressions is a model for extracting microexpressions. Optionally, the method further includes the step of calculating a global head motion based on data received from at least one of the following: inertial measurement unit of the HMS, and an external device configured to track the HMS.

Optionally, the HMS is a first HMD; and further comprising calculating a facial and/or body avatar for the user, sending the avatar to a second HMD, and presenting the avatar of the user on the second HMD; wherein the first and second HMDs comprise similar hardware and functionality, and the first HMD is configured to present the avatar of the second user on the first HMD. Optionally, the HMS is a first mixed reality HMD (MR-HMD); and further comprising calculating a non-complete facial avatar for the user, which covers at least some of the facial area occluded by the MR-HMD, sending the non-complete facial avatar to a second MR-HMD, and presenting the non-complete facial avatar of the user on the second MR-HMD, such that the user of the second MR-HMD sees simultaneously a combination of the user's real face and the non-complete facial avatar. In one example, the integrated operation of two or more HMDs with inward facing cameras, which can exchange posture and/or facial data in real time, enables the users to make large angle movements and move aside, essentially without affecting the exchanged posture/facial data.

In one embodiment, an emotion awareness head mounted display (HMD) configured to identify facial expressions to which the user may not be aware, and provide a feedback to the user to develop awareness on how the user feels and/or understand the trigger to the emotion driving the facial expressions. The HMD includes: a frame configured to be worn on the user's head; a display coupled to the frame; a first camera coupled to the frame at a location that is less than 15 cm away from the user's right pupil, and oriented such that the user's right eyebrow is in the FOV of the first camera and the user's left oral commissure is not in the FOV of the first camera; a second camera coupled to the frame at a location that is less than 15 cm away from the user's upper lip, and oriented such that the user's right upper lip is in the FOV of the second camera and the user's left eyebrow is not in the FOV of the second camera; wherein the location and orientation of the first, second, third and fourth cameras relative to the user's head do not change even when the user's head performs wide angular movements; and a processor configured to receive images from the first and second cameras, utilize a machine learning trained classifier to identify a facial expression expressed by the user, and present on the display a feedback related to the identified facial expression.

Optionally, the facial expressions are microexpressions, and the machine learning trained classifier identifies microexpressions expressed by the user. Optionally, the angle between the optical axis of at least one of the first and second cameras and the Frankfort horizontal plane is greater than 20 degrees. Optionally, the entire left eyebrow of the user is not in the FOV of the first camera. Optionally, the locations of the first and second cameras are less than 10 cm away from the user's face. Optionally, the locations of the first and second cameras are less than 5 cm away from the user's face.

Optionally, the optical axes of at least one of the first and second cameras is at least 20 degrees away from the Frankfort horizontal plane. Optionally, the optical axes of at least one of the first and second cameras is at least 30 degrees away from the Frankfort horizontal plane. Optionally, the optical axes of at least one of the first and second cameras is at least 45 degrees away from the Frankfort horizontal plane. Optionally, the optical axes of at least one of the first and second cameras is at least 60 degrees away the Frankfort horizontal plane.

Optionally, the HMS further includes a third camera coupled to the frame at a location that is less than 10 cm away from the user's right pupil; the third camera is oriented such that the lower orbital part of the user's orbicularis oculi muscle that surrounds the user's right eye is in the FOV of the fifth camera, and the user's left oral commissure is not in the FOV of the third camera; wherein the location and orientation of the third camera relative to the user's head does not change even when the user's head performs wide angular movements. In one example, the upper orbital part of the user's right side orbicularis oculi muscle is also in the FOV of the third camera. In another example, the distance between the third camera and the right lower orbital part is below 5 cm.

In one example, the HMS further includes a fourth camera coupled to the frame at a location that is less than 10 cm away from the user's left pupil; the fourth camera is oriented such that the lower orbital part of the user's orbicularis oculi muscle that surrounds the user's left eye is in the FOV of the fourth camera, and the user's right oral commissure is not in the FOV of the fourth camera; wherein the location and orientation of the fourth camera relative to the user's head does not change even when the user's head performs wide angular movements. Optionally, the image captured by the fourth camera further includes the upper orbital part of the user's left side orbicularis oculi muscle.

In one embodiment, a method for identifying facial expressions of a user wearing a head mounted system (HMS), includes the following steps: receiving first and second video streams from first and second cameras, respectively; the cameras are pointed at the user and are coupled to the HMS at locations that do not change relative to the user's head even when the user's head performs wide angular movements; wherein the user's right upper lip and left upper lip are in the fields of view (FOVs) of the first and second cameras, respectively, the middles of the user's right and left eyebrows are not in the FOVs of the first and second cameras, respectively, and the optical axes of the first and second cameras point at least 20 degrees below the Frankfort horizontal plane; and identifying the facial expressions of the user based on a model for extracting facial expressions from data comprising the first and second video streams.

In one embodiment, a head mounted system (HMS) configured to collect brainwaves and facial expressions of a user wearing the HMS, includes the following elements: a frame configured to be worn on the user's head; brainwave electrodes coupled to the frame; and a first camera coupled to the frame at a location that is less than 20 cm away from the user's right upper lip; the first camera is oriented such that the user's right upper lip is in the field of view (FOV) of the first camera, and the optical axis of the first camera points at least 20 degrees below the Frankfort horizontal plane; wherein the locations of the brainwave electrodes and the first camera, relative to the user's head, do not change even when the user's head performs wide angular movements.

Figure 16:
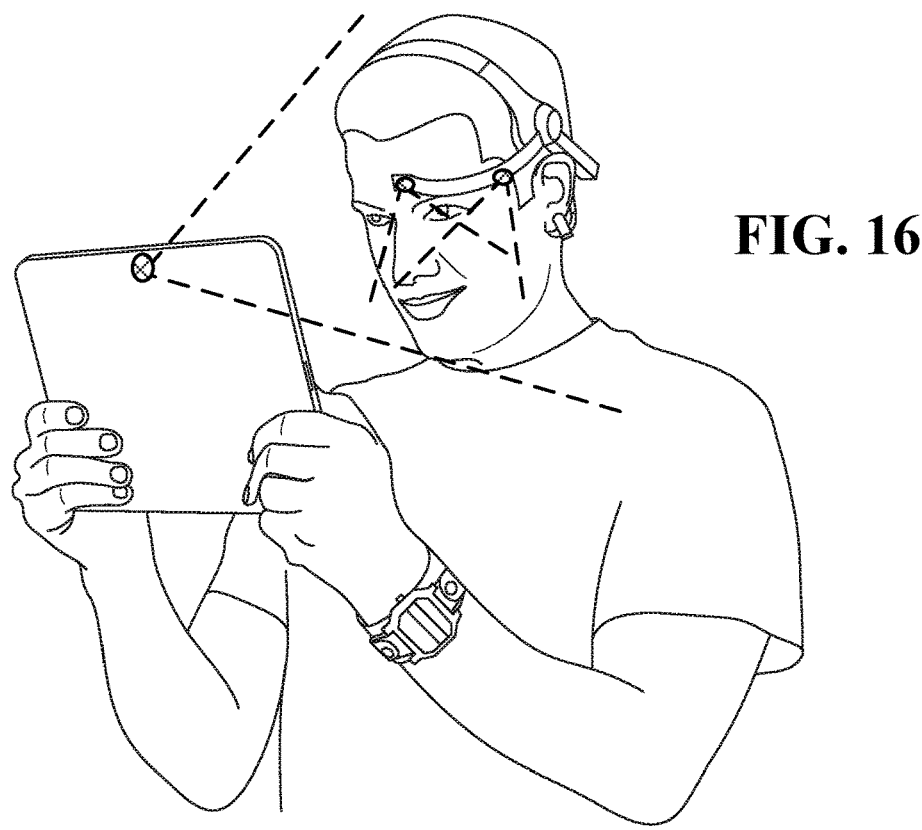
FIG. 16 and FIG. 17 illustrate brainwave headsets having at least two inward facing cameras that capture the user's facial expressions.
Figure 17:
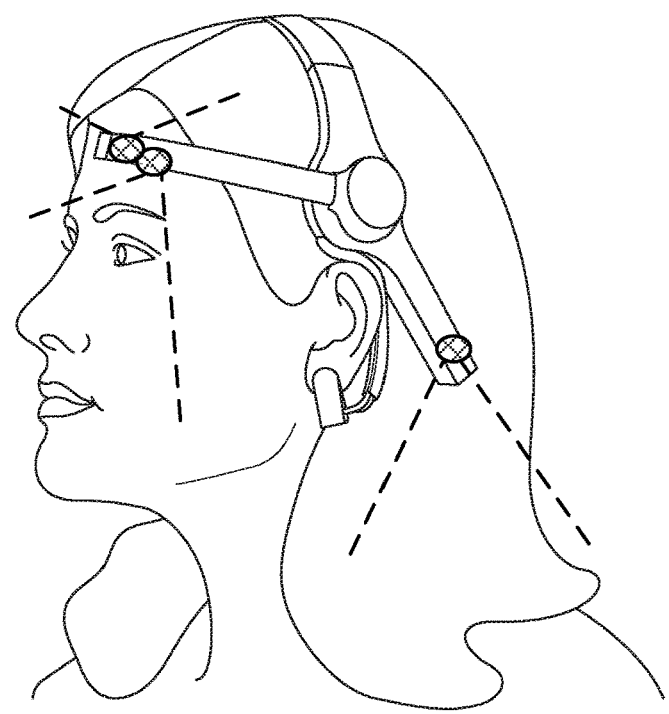
Figure 18:
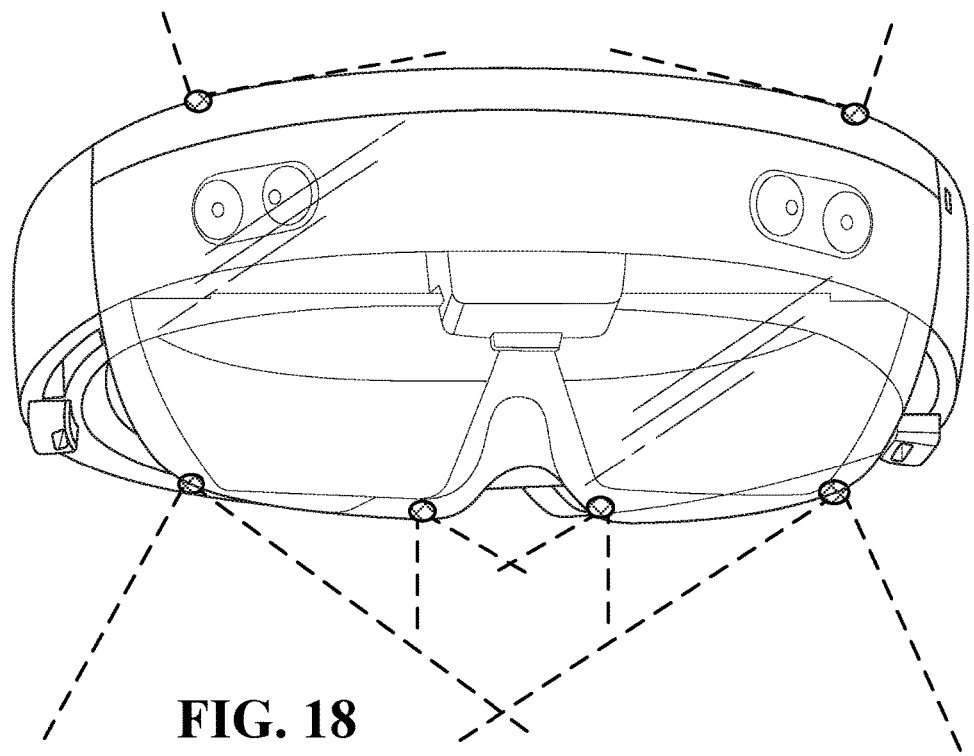
FIG. 18 illustrates an HMD having head mounted cameras able to capture both the user's face and the user's back.

Optionally, the HMS further includes a computer configured to calculate affective response of the user based on data received from the brainwave electrodes and the first camera. Optionally, the middles of the user's left eyebrow is not in the FOVs of the first camera. Optionally, the HMS further includes a second camera coupled to the frame, at a location that is less than 15 cm away from the user's left eyebrow; wherein the second camera is oriented such that the user's left eyebrow is in the field of view (FOV) of the second camera. Optionally, the HMS further includes a processor configured to extract vision-related features from data derived from images captured by the first and second cameras, and to utilize a machine learning trained classifier to identify a microexpression expressed by the user. Optionally, the data is derived from first and second video streams received from the first and second cameras; and wherein the vision-related features comprise temporal features. Spec: FIG. 16 and FIG. 17 illustrate brainwave headsets having at least two inward facing cameras that capture the user's facial expressions.

In one embodiment, a method for identifying affective response of a user wearing a head mounted system (HMS), includes the following steps: receiving brainwave signals from electrodes coupled to the HMS; receiving video streams from first and second cameras coupled to the HMS at locations that are less than 15 cm away from the user's face, and pointed at the user; the first camera is oriented such that more than 30% of the user's right cheek is in the FOV of the first camera, and the optical axis of the first camera points at least 20 degrees below the Frankfort horizontal plane; the second camera is oriented such that the more than 50% of the user's left eyebrow and less than 30% of the user's right cheek are in the FOV of the second camera; wherein the locations of the first and second cameras, relative to the user's head, do not change even when the user's head performs wide angular movements; and identifying facial expressions and/or microexpressions based on images captured by the first and second cameras; and calculating affective response of the user based on the brainwave signals and the identified facial expressions and/or microexpressions.

In one embodiment, the HMD is configured to identify brow contraction and/or Pursed lips using one or more cameras pointed at the brows and/or lips. When there is a contraction longer that a predetermined threshold (for example greater than 2, 5, or 10 seconds), the HMD alerts the user to release the contraction using visual and/or auditory notification. Optionally, when the user gets angry the system waits with the alert at least 30 second so that the notification does not make the user angrier. Optionally, the HMD shows a visual effect, such as red background or a degrading graph, when the user contracts the muscle at the Ajna chakra. As the user continues with the contraction, the visual effect gets more significant. As the user reduces the contraction, the visual effect gets less significant until it disappears.

In some cases, the system needs very limited face tracking and registration because the head mounted cameras are fixed to the user's face. The system needs limited tracking and registration also for estimating posture because the angle of view is limited by the possible movements of the body model. For example, the user cannot make any arbitrary movement with the head, thus the search space of head mounted cameras is limited in relation to the search space of an external camera that is not mounted on the user (such as Microsoft Kinect camera placed on a television display).

In one embodiment, a system configured to generate an avatar of a user's face from wearable cameras, includes: a frame configured to be worn on the user's head; first, second, and third cameras coupled to the frame, at locations that are less than 15 cm away from the user's head, respectively; the locations of the first, second and third cameras relative to the user's head do not change even when the user's head performs wide angular movements; the first, second, and third cameras are oriented such that at least 50% of: the right upper horizontal facial third, the left middle horizontal facial third, and the right lower-middle horizontal facial third are in the fields of view (FOVs) of the first, second, and third cameras, respectively; the FOVs of the first, second, and third cameras do not cover the at least 25% of: the left lower horizontal facial third, the right upper horizontal facial third, and the left upper horizontal facial third, respectively; and a training module configured to train a model based on data received from the first, second, and third cameras, and from an external camera; wherein the external camera captures in its FOV at least 80% of the user's upper, middle, and lower horizontal facial thirds, and is not worn on the user's head; wherein the model is configured to calculate information for rendering a facial avatar, which represents at least 80% of the user's face, without receiving from the external camera a stream comprising images of at least 80% of the user's upper, middle, and lower horizontal facial thirds.

Optionally, the model is configured to fill in missing data, based on the training, in order to calculate information for rendering the facial avatar, including a part of the user's face that is not directly available from data received from the first, second, and third cameras. Optionally, the model comprises correlations between data received from the first, second, and third cameras, and the missing data. Optionally, the model comprises a machine learning algorithm that receives, as input, data derived from the first, second, and third cameras, and outputs a model of the face of the user. Optionally, the HMS further includes a helmet coupled to the frame and configured to protect the user's scalp; wherein the helmet is selected from the group of: a sport helmet, a motorcycle helmet, a bicycle helmet, and a combat helmet.

In one embodiment, a HMS configured to collect facial expressions of the user wearing it, includes: a frame configured to be worn on the head of the user; a first camera, coupled to the frame, configured to picture the user above the right eye; a second camera, coupled to the frame, configured to picture the right eye of the user; a third camera, coupled to the frame, configured to picture the right upper lip of the user; wherein the first, second and third cameras do not have a direct line of sight to a part of the lips of the user; a processor, carried by the user, configured to receive images from the first camera, the second camera, and the third camera, and to extract data required by a model configured to render the face of the user, including the part of the lower lip; and a communication unit configured to send the data required by the model to a computer that is not fixed to the frame; wherein the entropy of the data required by the model is less than 10% of the entropy of the images from the first camera, the second camera, and the third camera.

Optionally, the processor is fixed to the frame. Optionally, the processor is located in a mobile phone associated with the user. Optionally, the processor is located in a wearable computer associated with the user. Optionally, the model is configured to render the face of the user as seen with the HMS. Optionally, the model is configured to render the face of the user as seen without the HMS.

Figure 20:
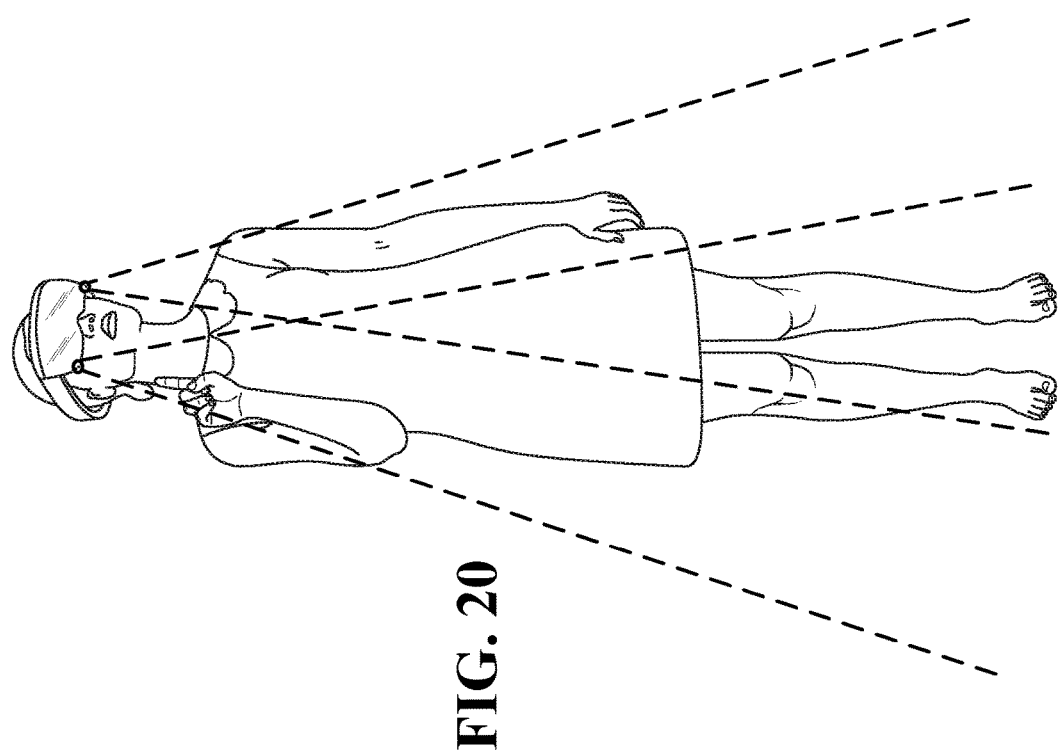
FIG. 20 illustrates a HMD having head mounted cameras able to capture portions of the user's torso, hands, and legs.

FIG. 20 illustrates one embodiment of a HMD with cameras useful for estimating the posture of a user wearing the HMD. One of more of the cameras used to capture the user's body may feature an extended DOF, such as: (i) a camera that operates according to Scheimpflug principle, (ii) a light field camera, and/or (iii) a camera that utilizes at least one of the following techniques to achieve an extended depth of field: wavefront coding, diffusion coding, coded aperture, multiple apertures, and/or lens array.

Figure 21:
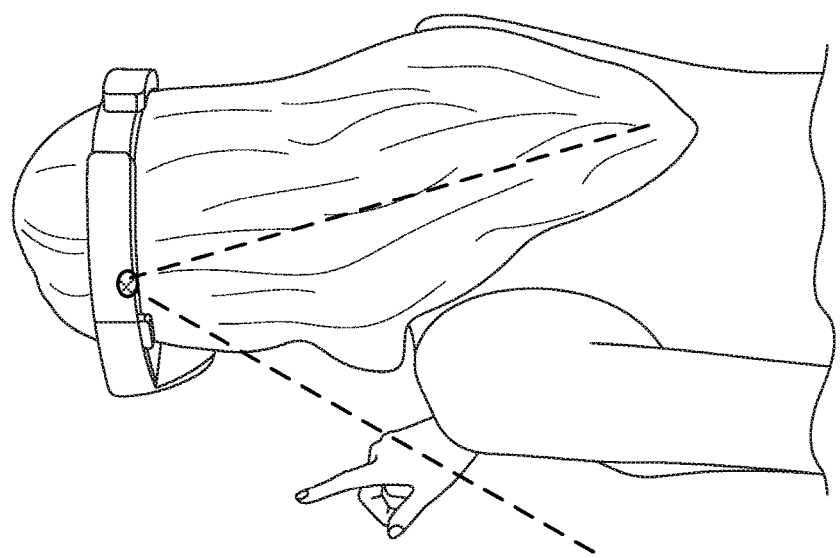
FIG. 21 illustrates a HMD having head mounted a camera able to capture the user's shoulder.

FIG. 21 illustrates one embodiment of a HMD with a side camera useful for estimating the posture of a user wearing the HMD. In normal standing the user's shoulder is in the FOV of the side camera.

In one embodiment, a head mounted system (HMS) configured to estimate posture of a user wearing the HMS, includes: a frame configured to be worn on the head of the user; first and second cameras, coupled to the frame at locations that are to the right and to the left of the symmetry axis that divides the face to the right and left sides, respectively, and less than 15 cm away from the user's head; wherein the first and second cameras are oriented downward such that portions of the user's torso are in the fields of view (FOVs) of the first and second cameras when the user stands up straight; and a training module configured to train a model for estimating posture of the user based on data received from the first and second cameras; wherein the training assumes that the locations of the first and second cameras, relative to the user's head, do not change even when the user's head performs wide angular and lateral movements.

Optionally, at least one of the first and second cameras is a depth camera. Optionally, the first and second cameras point at least 20 degrees to the right and to the left of the anterior facial plane, respectively. Optionally, the first camera is located behind the user's right ear.

In some embodiments, assuming that the locations of the first and second cameras, relative to the user's head, do not change even when the user's head performs wide angular and lateral movements, simplifies at least one of the training module and the model for estimating user's posture, compared to equivalent cases where it impossible to assume that the cameras have fixed positioning relative to the user's head. The assumption of fixed positioning relative to the user's head may also improve the performance of the model and reduce the required computations load compared to equivalent cases where it is impossible to make such assumption.

Optionally, the HMS further includes a third camera, coupled to the frame at a location behind the user's ear; wherein the third camera is oriented downwards such that a portion of the user's torso is in the FOV of the third camera when the user stands up straight; and wherein the training module is further configured to train the model based on data received from the third camera while assuming that the location of the third camera, relative to the user's head, does not change even when the user's head performs wide angular and lateral movements.

Optionally, the HMS further includes an inertial measurement unit (IMU) coupled to the frame and configured to measure orientation of the frame; wherein the training module is further configured to utilize the orientation for training the model. Optionally, the model is configured to estimate the angle between the head and the torso of the user based on the data received from the first and second cameras and the orientation measured by the IMU.

Optionally, the HMS further includes an external camera, which is not mechanically coupled to the frame, configured to have a direct line of sight to the front side of user's torso; wherein the training module is further configured to utilize data from the external camera in order to train the model.

Optionally, the HMS is coupled to a head mounted display comprising a display configured to present digital content to the user. Optionally, the HMS is coupled to at least one of a helmet and a hat; wherein the helmet is selected from the group of: sport helmet, motorcycle helmet, bicycle helmet, and combat helmet. Optionally, the HMS is coupled to a brainwave headset configured to collect brainwave signals of the user.

Figure 22:
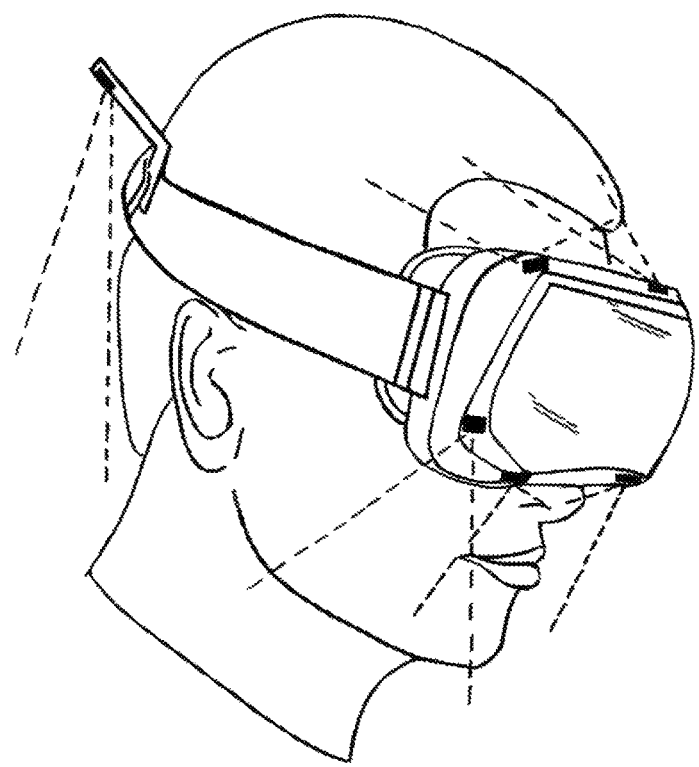
FIG. 22, FIG. 23, FIG. 24, and FIG. 25 illustrate HMDs having head mounted cameras able to capture both the user's face and the user's back.
Figure 23:
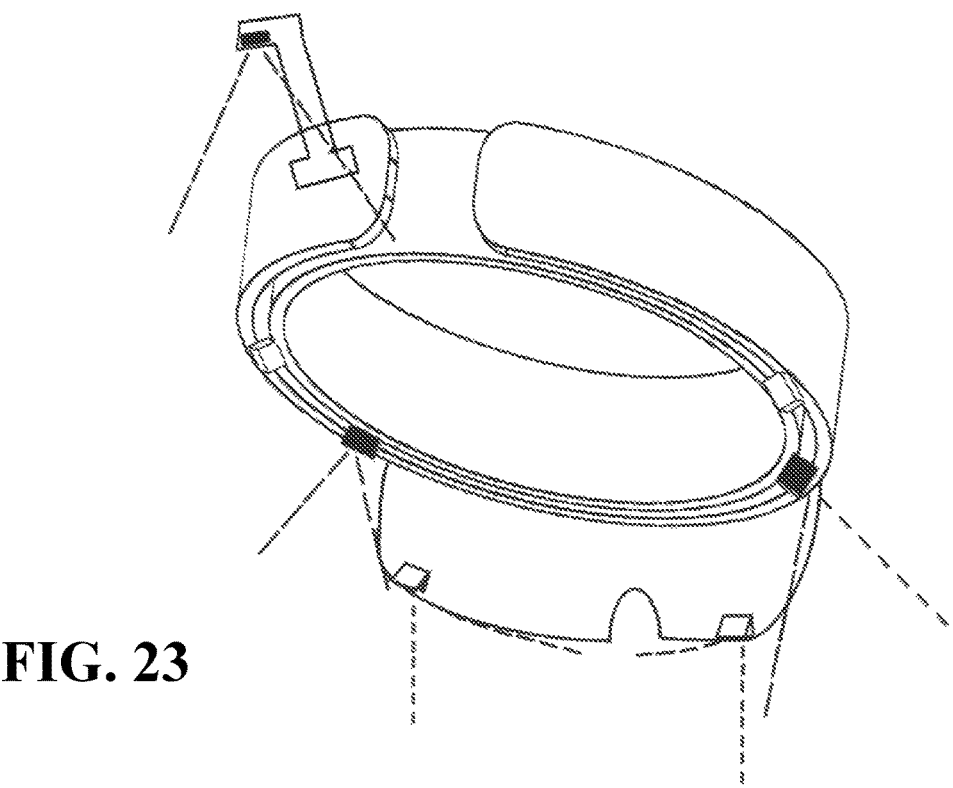
Figure 24:
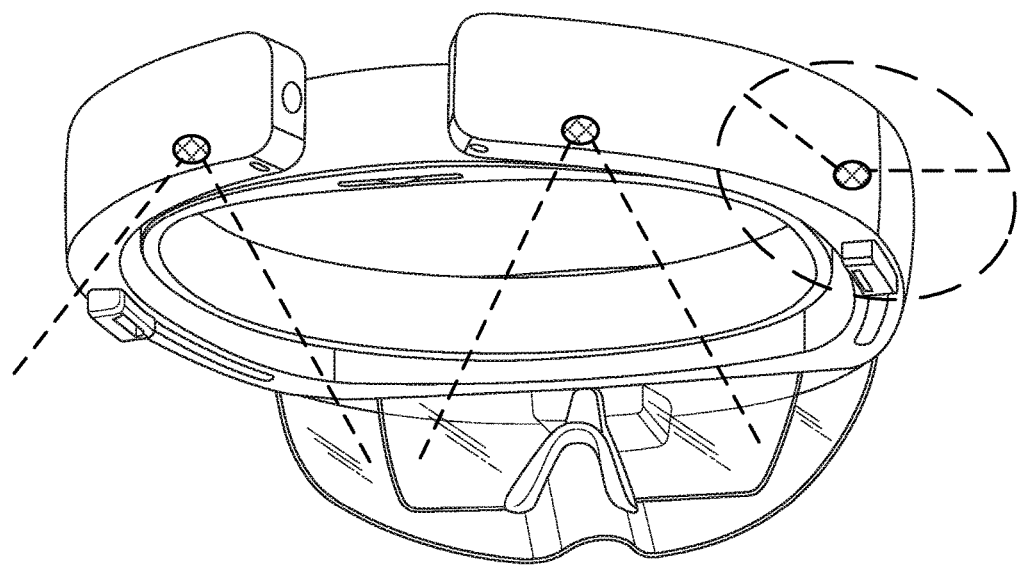
Figure 25:
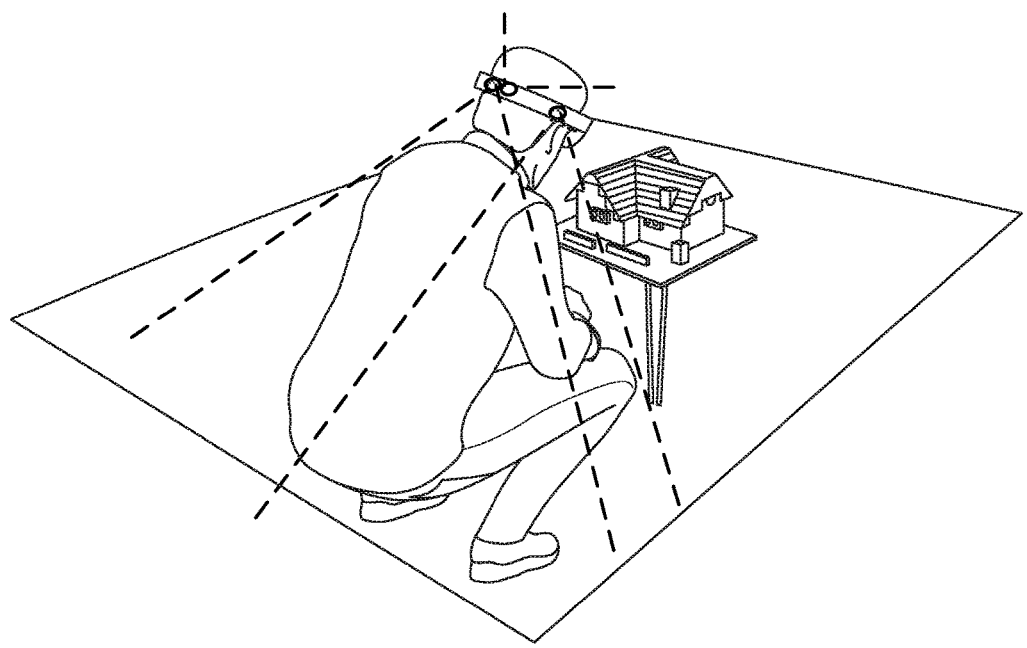

FIG. 22 illustrates one embodiment where the camera is coupled to an extender that is coupled to the head band of the HMD. FIG. 23 illustrates one embodiment where the camera is coupled to an extender that is coupled to the frame of the HMD. The extender may be an element on which the camera may adjust angles, optionally manually and/or using one or more motors. The extender may help to prevent concealment and may improve the field of view captured by the camera. The type of extender is not limited to the type illustrated in FIG. 22 and FIG. 23. The extender may have any shape that extends the camera away from the head, and/or may be formed as an integral part of the frame and/or any other part of the HMS. The extender may be coupled to the front, side, or rear portion of the HMD.

In one embodiment, a head mounted system (HMS) configured to identify posture and facial expression of a user wearing the HMS, includes: a frame configured to be worn on the user's head; an inertial measurement unit (IMU) coupled to the frame and configured to measure orientation of the frame; first and second cameras coupled to the frame, at locations that are before and after the ears, respectively, and less than 15 cm away from the user's head; the first and second cameras are oriented such that at least a portion of one of the user's eyebrow and at least a portion of one of the user's shoulder blades are in the fields of view (FOVs) of the first and second cameras, respectively; wherein the locations of the first and second cameras, relative to the user's head, do not change even when the user's head performs wide angular movements; and a computer configured to estimate the user's posture and facial expression based on: a model of the human body parameterized by pose, a model of the human face parameterized by expression, measurements of the IMU, and data extracted from images captured by the first and second cameras.

One examples of a model of the human body parameterized by pose is described in the reference Zuffi, S., Black, M. J. (2015), "The Stitched Puppet: A Graphical Model of 3D Human Shape and Pose", In IEEE Conf. on Computer Vision and Pattern Recognition (CVPR).

One example of a model based on a loose-limbed body model that requires a specification of the probabilistic relationships between body parts at a given time instant and over time is described in the reference Sigal, L., Isard, M., Haussecker, H., Black, M. J. (2012), "Loose-limbed people: Estimating 3d human pose and motion using non-parametric belief propagation", International journal of computer vision, 98(1), 15-48.

More example of part-based model are described in the reference Ghosh, S., Sudderth, E., Loper, M., Black, M. (2012), "From Deformations to Parts: Motion-based Segmentation of 3D Objects", In Advances in Neural Information Processing Systems 25 (NIPS), MIT Press, pages 2006-2014; and in the reference Hirshberg, D., Loper, M., Rachlin, E., Black, M. J. (2012) "Coregistration: Simultaneous alignment and modeling of articulated 3D shape", In European Conf. on Computer Vision (ECCV), Springer-Verlag, LNCS 7577, Part IV, pages 242-255.

One example of a model for on estimating articulated body posture and motion from monocular video sequences is described in the reference Rosales, R., Sclaroff, S. (2000), "Inferring body pose without tracking body parts", In IEEE Computer Society conference on computer vision and pattern recognition (CVPR) (Vol. 2, pp. 721-727).

One example of a model for predicting soft-tissue deformations is described in the reference Pons-Moll, G., Romero, J., Mahmood, N., Black, M. J. (2015), "Dyna: A Model of Dynamic Human Shape in Motion", ACM Transactions on Graphics, (Proc. SIGGRAPH).

Figure 19:
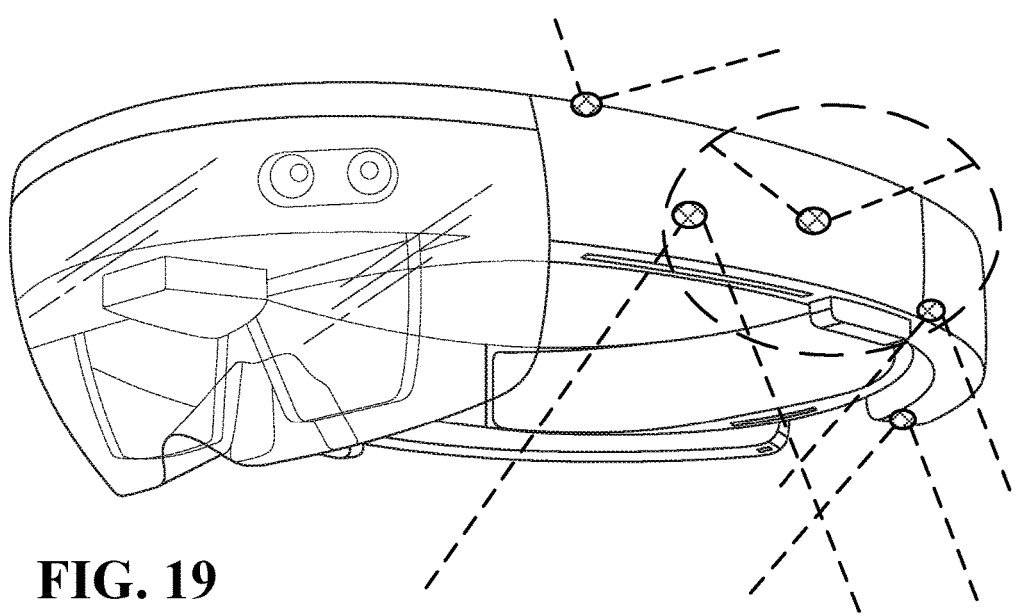
FIG. 19 illustrates a HMD having head mounted cameras around the head.

FIG. 19 illustrates a HMD having head mounted cameras around the head, such that the head mounted cameras are able to capture the user's hands when stretched to the sides. In other words, the mead mounted cameras may be able to measure the user's hand almost in any direction they are stretched.

FIG. 20 illustrates a HMD having head mounted cameras able to capture portions of the user's torso, hands, and legs.

FIG. 21 illustrates a HMD having head mounted a camera able to capture the user's shoulder.

FIG. 18, FIG. 22, FIG. 23, FIG. 24, and FIG. 25 illustrate HMDs having head mounted cameras able to capture both the user's face and the user's back.

Figure 26:
FIG. 26 and FIG. 27 illustrate HMDs having head mounted cameras able to capture both the user's facial expressions and hand gestures with the same camera.
Figure 27:

FIG. 26 and FIG. 27 illustrate HMDs having head mounted cameras able to capture both the user's facial expressions and hand gestures with the same camera.

In one embodiment, a portal effect that enables the user himself passes through a portal includes the following steps: the HMD measures the user's posture; the portal has a physical location in the real world; when the user passes the portal, the user sees a change in the environment. Optionally, the user and/or other users actually see the transient, i.e., how part of the user's body is in the new location and another part in the previous location; when the user passes the portal he may have a different avatar. Optionally, the user and/or other users may have the effect of seeing how the user's avatar changes as the user passes the portal. Optionally, other users can also see the transient effect of the user passing the portal, and they see the change of the environment. This is especially useful for portals that connect between different worlds.

In one embodiment, a head mounted display (HMD) systems configured to cooperate, includes: first and second head mounted display (HMD) systems, worn on first and second users, respectively; each HMD includes: a frame, a display, an inertial measurement unit (IMU), first and second cameras, a communication module, and a computer; the frame is configured to be worn on its user's head; the IMU is coupled to the frame and configured to measure orientation of the frame; the first and second cameras are coupled to the frame, at locations that are less than 15 cm away from its user's head; the first and second cameras are oriented downwards such that at least a portion of its user's front torso and at least a portion of one of its user's shoulder blades are in the fields of view (FOVs) of the first and second cameras, respectively; wherein the locations of the first and second cameras, relative to its user's head, do not change even when its user's head performs wide angular movements; and the computer is configured to calculate its user's posture based on: a model of the human body, measurements of the IMU, and data extracted from images captured by the first and second cameras; the communication module of the first HMD is configured to send the calculated posture of its user to the communication module of the second HMD, and vice versa; the computer of the first HMD is configured to render an avatar of the second user, based on the received posture of the second user, and vice versa; and the display of the first HMD is configured to present the avatar of the second user to the first user, and vice versa.

Optionally, the communication modules are further configured to exchange the measurements of the IMUs, and the computers utilize the measurements of the IMUs in the processed of determining where to render the avatars. Optionally, the distance between the first and second users is more than 10 meter. Optionally, there is no line of sight between the first and second users. Optionally, the HMDs are mixed reality HMDs, the rendered avatar of the second user (as presented to the first user) covers at least 10% of the physical body of the second user as seen by the first user, and vice versa. Optionally, the HMDs are virtual reality HMDs, the rendered avatar of the second user (as presented to the first user) is located at a relative angle to the first user which essentially corresponds to their relative angle in the real world, and vice versa. Optionally, "essentially corresponds" is interpreted as less than 15% inaccuracy in the angle when comparing the real and virtual angles to the second user as seen by the first user. Optionally, the virtual distance between the users is exaggerated in order to create an effect of fast movement along the Cartesian axes. Optionally, the HMDs are virtual reality HMDs, the rendered avatar of the second user (as presented to the first user) is located at a relative position to the first user which essentially corresponds to their relative position in the real world, and vice versa. Optionally, "essentially corresponds" is interpreted as less than 15% inaccuracy in angle and distance when comparing the real and virtual angles and distances to the second user as seen by the first user. Optionally, the HMDs system runs a game. Optionally, the HMDs system runs a video conference.

The embodiments described in this document may be utilized to implement one or more of the following multiplayer game embodiments:

In one embodiment, a user controls his/her model that is sent to other users, instead of the case where the other users control the user's model. This is useful for effects the user wants to apply on his avatar. Examples of scenarios having a need to enable to the user to control his/her avatar include multiplayer game, video conference, multiplayer events, when the user wants to look differently to different people who see the user simultaneously, when the user owns a unique model and does not want to share it with others, or when the user won a special "force" in a game.

In one embodiment, when user B can measure user A, then user B sends the measurements to user A, and these measurements are used to improve the model of user A (obtained from the HMD of user A). Optionally, the improved model of user A (based on measurements from both user A and user B) is sent to user C who cannot measure user A directly, but still enjoys from the improved model.

In one embodiment, a HMD of User A measures user B in order to render an avatar over user B for user A. HMD of user B sends the self-measured avatar of user B to the HMD of user A, which uses the received model to improve the accuracy of its rendering of the avatar over user B.

In one embodiment, players who are not present in the same room may see each other in the same room by replacing the models.

In one embodiment, the perceived size of a room is increased by hiding the walls, and playing with another user that his model appeared to be presented beyond the wall.

In one embodiment, user A is provided with an effect of seeing through a physical wall by receiving a self-measured avatar from user B who stands beyond the wall.

In one embodiment, a user can also send with a model (generated based on this HMD) objects he touches/holds, such as: a sword, a book, and a flower. For example, a user can give his girlfriend a flower by sending his model plus a model of the flower (which can be virtual, but both sides see it), and the girlfriend sees the flower as if she stands in front of the user (when they are physically located in places without a direct line of sight). Usually, the system accesses/prepares a model of the object in advanced, so that it can render the model in real time according to the user's actions.

In one embodiment, the user can have the feeling of living/working/traveling/learning/playing with a real human when each is in his own home. This is kind of a virtual-real partner because the parties are real, but each party is physically located in a different place, and they see each other through the exchanged avatars.

In one embodiment, the system supports changing perspective in a multiplayer game. Assume the user plays outside and wants to have an effect of becoming taller or shorter, or effect of flying. Because others users send the user their models, and the user has the model of the world, then the user's HMD can change the user's perspective on the situation while continuing to receive the real movements of the real people.

In one embodiment, a user can see himself from the side. Might be interesting when the user wants to understand how he/she looks to others.

In one embodiment, the system creates an effect that the user is in someone else's body. User B sends his model to user A who sees what user B sees and also can see user's B body. This embodiment requires user A to be able to measure the body of user B. Optionally, the system renders a point of view as if user A follows user B (as if user A looks behind/goes after user B).

In one embodiment, the user's HMD measures the user's posture and generates an avatar of the user; the avatar is duplicated as one or more avatars around the user, where the duplicated avatars do what the user does (based on the user's model, as measured by the HMD). The user's duplications can be rendered as facing the same direction the user faces, as a mirror image (optionally in front of the user), and/or as playing with the user by imitating the user. Examples of games based on this technology include: the user is walking in parade with a thousand replications doing exactly what the user does, a ballet dancer can see many ballet dancers doing the same movements as he/she does (and optionally in a perfect synchronization), the user can see himself participating in a dance ball, line dances, Zumba—where everyone is doing exactly whatever the user does, or doing something that matches the movements the user does (in this example, the HMD measures the user's movements, and then the behavior of the replications is set based on the behavior of the user's movements). Optionally, the duplications are rendered in the real world, essentially everywhere, from any required angles, outdoors, and/or without an external tracking system to track the user's posture.

In one embodiment, a method for saving calculation power in a multiplayer game environment includes the following steps: Each user measures himself and the environment, and sends his measurements to a centralized computer and/or shares his measurements/models with the other users in the same physical room. The computer uses the measurements/models received from user to calculate the model of the room and the users, and sends the model of the environment to the users for rendering. This especially saves power in multiplayer games where each user cannot measure all the people around him because there are too many of them. But a centralized computer can track all the models and build a unified model based on the models it receives.

In one embodiment, user A and user B are involved in a multi-player game, where user A sees user B as an avatar that covers user B such that the avatar is bigger than user B. When user B is occluded by an object (which may be stationary such as a wall or a furniture, or non-stationary such as another user), part of the avatar of user B may still be visible to user A. In order to enable user A to render correctly the avatar of user B, the HMD of user B sends data describing the posture of user B, and the HMD of user A renders user's B avatar correctly based on the received data.

In one embodiment, a head mounted system (HMS) configured to collect facial cues of a user wearing the HMS, includes at least a frame and first and second cameras coupled to the frame. The frame is worn by the user and is situated on the user's head. In one example, the frame of the HMS may be the frame of eyeglasses, goggles (e.g., used for skiing, motor sports, skydiving, or diving), or any other device which houses lenses through which a user may peer at the physical world. In another example, the frame of the HMS includes the frames in the previous example, but possibly lacking one or more lenses. In still another example, the frame may belong to a head-mounted display (HMD) that presents to the user digital content. For example, the HMD may be an augmented reality display, a virtual reality display, and/or a mixed reality display.

In one embodiment, the first and second cameras are coupled the frame at locations that are to the right and to the left of the symmetry axis that divides the face to the right and left sides, respectively. In one example, the locations at which the first and second cameras are couple to the frame are such that each location is less than 15 cm away from the closest pupil of the user. That is, the first camera is coupled to the frame at a location that is at most 15 cm away from the user's right pupil, and the second camera is coupled to the frame at a location that is at most 15 cm away from the user's left pupil.

The first and second cameras are oriented such that the middles of the user's right and left eyebrows are in the fields of view (FOVs) of the first and second cameras, respectively. Additionally, the orientation of the first and second cameras is such that the user's left and right oral commissures are not in the FOVs of the first and second cameras, respectively.

In some examples, the first and second cameras are coupled to the frame in such a way that the locations of the first and second cameras relative to the user's head do not change even when the user's head performs wide angular movements. In one example, the first and second cameras are coupled to the frame by being attached to the frame in a rigid manner such that their orientation and/or position relative to the frame do not change when the user moves his/her head while wearing the HMS. In another example, the first and second cameras are coupled to the frame by being attached to the frame in an essentially rigid manner. Optionally, when attached in an essentially rigid manner, the orientation and/or position of the first and second cameras relative to the frame do not change by more than 5° when the user's head performs angular motion that exceeds 30°. Additionally or alternatively, when attached in an essentially rigid manner and the user's head performs angular motion that exceeds 30°, the orientations of the first and second cameras relative to the frame revert to within one second to within 5° of the respective orientations relative to the frame, at which the first and second camera were oriented prior to the angular motion being performed.

In some embodiments, the first and second cameras produce first and second video streams. The first and second cameras may be various types of cameras in different embodiments. In one example, the first and second cameras are visible and/or thermal video cameras, and the first and second video streams may include visible and/or thermal images at rates of at least 1 Hz. Optionally, the first and second video streams comprise images that include portions of the face of the user who wears the HMS to whose frame the first and second cameras are coupled. In one example, images belonging to the first stream comprise a portion of the user's face that has limited overlap with the portion of the user's face comprised in images belonging to the second stream. Optionally, by "limited overlap" it is meant that at least 20% of the area of the user's face that appears in images belonging to the first stream does not appear in images belonging to the second stream, and vice versa. Optionally, by "limited overlap" it is meant that most of the area of the user's face that appears in images belonging to the first stream does not appear in images belonging to the second stream, and vice versa.

In some embodiments, one or more video streams generated utilizing one or more respective video cameras may be used for various applications such as generating an avatar of a user and/or determining emotional response of a user. Each of the one or more video cameras is coupled to a frame of an HMS worn by a user.

In one embodiment, each of the one or more video streams comprises images of at least a portion of the face of the user. Optionally, none of the one or more video streams comprises an image that includes a full frontal view of the user's face. Herein an image that comprises a full frontal view of a person's face is an image in which all of the following features of the person are visible: both ears, both eyes, both eyebrows, the nose, and the chin.

In one embodiment, at least one of the one or more video cameras is oriented towards the face of the user. Optionally, the angle between the optical axis of each of the at least one of the one or more video cameras and the Frankfort horizontal plane of the user is greater than 20 degrees. Optionally, the angle between the optical axis of each of the at least one of the one or more video cameras and the Frankfort horizontal plane of the user is greater than 30 degrees. Optionally, the angle between the optical axis of each of the at least one of the one or more video cameras and the Frankfort horizontal plane of the user is greater than 45 degrees.

In one embodiment, none of the one or more video streams are a video stream that may be characterized as follows: (1) the video stream is generated by a camera coupled to a frame of an HMS worn by a user, (2) the stream includes an image comprising a full frontal view of the user's face, and (3) the camera is pointed towards the user's face and the angle between the optical axis of the camera and the user's Frankfort horizontal plane is less than 20 degrees.

Each camera from among the one or more cameras may be a certain type of camera. In one example, a camera from among the one or more cameras may be a visible light camera (e.g., RGB camera). In another example, a camera from among the one or more cameras may be a thermal imaging camera (IR camera). In still another example, a camera from among the one or more cameras may be a light field camera. In some embodiments, the frame of the HMS may have different types of cameras coupled to it. For example, the frame may have four cameras couple to it; two cameras may be IR cameras and another two may be visible light cameras. In other example, all the cameras coupled to the frame of the HMS are of the same type. For example, the frame has four cameras coupled to it, all of which are IR cameras, each pointed at different regions of interest (ROIs).

In some embodiments, two cameras of different types, which are couple to the frame, may both be pointed at the same ROI. For example, the two cameras may be an IR camera and a visible light camera, situated next to each other and both pointed to the same area of the user's nose.

Each camera from among the one or more cameras may be coupled to the frame at a different location on the frame and/or may be oriented at a certain orientation relative to the frame. Optionally, each of the one or more cameras is coupled to the frame in such a way that the location and orientation of the camera relative to the user's head does not change even when the user's head performs wide angular movements. Following are some examples of locations and/or orientations cameras may possess in different embodiments.

In one embodiment, a camera from among the one or more cameras is coupled to the frame at a location that is to the right of the symmetry axis that divides the face to the right and left sides, and is less than 15 cm away from the middle of the user's right eyebrow. Additionally, the camera is oriented such that the middle of the user's right eyebrow is in the FOV of the camera, and the user's left oral commissure is not in the FOV of the camera. Optionally, the angle between the optical axis of the camera and the Frankfort horizontal plane is greater than 20 degrees. Optionally, the angle between the optical axis of the camera and the Frankfort horizontal plane is greater than 30 degrees. Optionally, the angle between the optical axis of the camera and the Frankfort horizontal plane is greater than 45 degrees. Additionally or alternatively, a similar configuration may be applied to a camera from among the one or more cameras that is coupled to the frame at a location that is to the left of the symmetry axis, and is less than 15 cm away from the middle of the user's left eyebrow.

In one embodiment, a camera from among the one or more cameras is coupled to the frame at a location that is to the right of the symmetry axis and less than 10 cm away from the user's right upper lip. Additionally, the camera is oriented such that the user's right upper lip is in the FOV of the camera, and the middle of the user's left eyebrow is not in the FOV of the camera. Optionally, the angle between the optical axis of the camera and the Frankfort horizontal plane is greater than 20 degrees. Optionally, the angle between the optical axis of the camera and the Frankfort horizontal plane is greater than 30 degrees. Optionally, the angle between the optical axis of the camera and the Frankfort horizontal plane is greater than 45 degrees. Additionally or alternatively, a similar configuration may be applied to a camera that is coupled to the frame at a location that is to the left of the symmetry axis and less than 10 cm away from the user's left upper lip.

In one embodiment, a camera from among the one or more cameras is coupled to the frame at a location that is less than 10 cm away from the user's right pupil. Additionally, the camera is oriented such that the skin around the user's right eye is in the FOV of the camera, and the user's left oral commissure is not in the FOV of the camera ("the skin around the eye" may refer to the periorbital area). In one example, the distance between the camera and the right eye is below 5 cm. Additionally or alternatively, a similar configuration may be applied to a camera that is coupled to the frame at a location that is less than 10 cm away from the left eye of the user.

In one embodiment, when the HMS is an occluded virtual reality HMD, the skin around the eyes may be measure using several small cameras placed within the hood of the HDM, and looking at the skin around the eyes. In one example, infrared LEDs are used to light the skin and infrared-only cameras are user to record the reflections.

The resolution of images from a video stream generated by a camera may vary, possibly significantly between embodiments described herein, and may depend on various factors such as the type of camera and/or a purpose the for which the images are to be used. In one embodiment, the camera may capture images that consist of a single pixel. For example, the camera may be a thermal imaging camera in close proximity to the face of the user (e.g., less than 2 cm from the surface of the face). In other embodiments, the camera may capture images comprising multiple pixels. The resolution of the images with multiple pixels may vary. Examples include 2 pixels, 2×2 pixels, 4×4 pixels, 16×9 pixels, 48×36 pixels, 64×64 pixels, and 256×56 pixels. Additional example include one of the following standard resolutions: CGA, VGA, PAL, XVGA, SD, 720p, 1080p, 2K, 4K, or 8K. Optionally, the ratio between the horizontal resolution and vertical resolution of the images is one of the following: 5:4, 4:3, 3:2, 16:10, 5:3, 16:9, 17:9, or 21:9. Alternatively, the ratio between the vertical resolution and horizontal resolution of the images is one of the following: 5:4, 4:3, 3:2, 16:10, 5:3, 16:9, 17:9, or 21:9. Optionally, the images may generate utilizing other resolutions known in the art or a custom sensor with resolutions or pixel counts that are not standardly used in the art.

The one or more video streams may include images generated at different rates (frequencies) depending on the embodiments. Herein a frequency and/or rate of a video stream may refer to the average number of images generated by the stream in a second and may be referred to as a number followed by Hz (Hertz) or as a number of frames per second (fps). Optionally, each of the one or more video streams operates at a rate of at least 1 Hz (i.e., on average its camera generates at least one image a second). Optionally, the rate of the video stream may be higher than 1 Hz, such as 10 Hz, 30 Hz, 60 Hz, 100 Hz, 200 Hz, a value between 1 Hz and 200 Hz, or a value higher than 200 Hz.

In some embodiments, the one or more video streams include multiple video streams, each including images generated at the same frequency. Alternatively, the one or more video streams involve a first video stream that includes images generated at a first rate and second video stream that includes images generated at a second rate that is higher than the first.

In some embodiments, at least some of the one or more video streams are synchronized. Optionally, synchronizing between video streams involves determining, for at least some images from a first stream, their corresponding images in a second stream. Optionally, when referring to corresponding images from different video streams, the relationship between two or more corresponding images is a temporal one, such that the corresponding images were taken essentially at the same time, or at a known offset from each other. In one example, a first image from the first stream corresponds to a second image in the second stream if it is taken at the same time as the second image in the second stream. In another example, two images from different video streams may be considered corresponding if they are taken within a certain time of each other. Optionally, the certain time may be a duration that is less than 0.01 seconds, less than 0.04 seconds, less than 0.1 seconds, or less than 1 second.

In some embodiments, different video streams may include images that were not taken exactly at the same time by their respective cameras (e.g., due to the cameras capturing images at different rates and/or starting capturing images at slightly different times). In such cases, it may be required to find corresponding images by determining which images from different video streams were captured essentially at the same time. In one example, a first image from a first stream and a second image from a second stream are considered corresponding images if the second image is taken before the first image is taken, but no other image in the second stream is taken at a time that is after the time the second image is taken and before the time the first image is taken. In another example, a first image from a first stream and a second image from a second stream are considered corresponding images if the second image is taken after the first image is taken, but no other image in the second stream is taken at a time that is before the time the second image is taken and after the time the first image is taken. In still another, a first image from a first stream and a second image from a second stream are considered corresponding images if the second image is an image from among the images in the second stream for which the difference between the time it was taken and the time the first image was taken is the smallest.

In one embodiment, an image from a first video stream that corresponds to an image from a second video stream may in fact represent multiple images from the first stream. For example, this may occur if the first stream include images generated at a higher frequency than the second stream. In such a case, there may be multiple images from the first stream that fall into a window during which the image from the second stream was taken. Optionally, the multiple images are represented by a single image (e.g., an average of the multiple images), which may in fact not be an image actually captured by the camera that generates the first stream.

When referring to images belonging to multiple video streams, a set of corresponding images is a set of images, each coming from a different video stream, which were taken essentially at the same time. Optionally, each pair of images in the set of corresponding images is considered to correspond to each other according to at least one of the examples for conditions for correspondence of images given above.

Embodiments described herein may involve representing images with feature values. The process of converting one or more images to feature values may be referred to herein as "feature generation" and/or "feature extraction". Optionally, the feature values may be represented as one or more vectors of feature values. Stating that feature values may be represented as a vector does not imply that they necessary need to be stored in a data structure that is a vector. Rather, that the features may be referred to logically as being in a vector such that each different feature corresponds to a different position (dimension) in the vector.

The terms "feature" and "feature value" may often be used interchangeably in this disclosure when the context of their use is clear. However, a "feature" typically refers to a certain type of value, and represents a property determined from one or more images. A "feature value" is the value of the property determined from the value of the one or more images. For example, a feature may be "distance between the edge of the left nostril and the edge of the left side of the lip". A feature value for that feature may be 3 cm. Optionally, when referring to feature values as vectors of feature values, each position in the vector (each dimension) represents a feature; the content of each position in the vector is a feature value (of the feature that corresponds to the position).

In some embodiments, data that represents images obtained from one or more video streams is converted into feature values. There are various ways to represent the data obtained from the one or more video streams as vectors of feature values, as explained in further detail below.

In one embodiment, each image belonging to a video stream is converted into a vector of feature values by extracting various feature values from the image. Optionally, multiple images (e.g., images belonging to a set of corresponding images), may be represented as a vector of feature values by combining feature values from vectors representing individual images. Optionally, some of the feature values in the vector representing the multiple images may be feature values taken from the vectors representing the individual images. For example, the vector representing the multiple images may include some, or even all, of the feature values of each vector representing an individual image. Optionally, some of the feature values in the vector representing the multiple images may be the results of functions of feature values from vectors representing individual images. For example, the vector representing the multiple images may include a feature value that is an average of feature values from different vectors representing individual images, or a difference between feature values from different vectors representing individual images.

In one embodiment, multiple images from one or more video streams may be converted into a vector of feature values by extracting various feature values from the images. For example, the multiple images may be stitched together (e.g., to create a single image representing a face) or represented as a single logical unit (e.g., a single image or file). Thus, extracting features from the multiple images may be done by accessing a single source (e.g., a single stitched image). Optionally, stitching the image may involve performing various image processing functions on individual images and/or the multiple images such as rotating, rescaling, and/or other transformations on the images.

Some methods for stitching multiple images of a face of user may involve mapping portions of the images to a 3D model of the face of the user. Thus, a 2D image of the user may be generated from the multiple images, even if the images are taken from different perspectives, may capture different portions of the face, and/or or may overlap, as may be the case in some of the embodiments described herein that involve images of one or more cameras coupled to a frame of an HMS worn by the user. In one example, combining the images of the one or more cameras into a single image from which features may be extracted may be done based on the teachings of Bradley, et al., "High resolution passive facial performance capture", in ACM Transactions on Graphics (TOG) 29.4 (2010): 41. Bradley et al. describe a method for constructing a 2D image that utilizes a 3D mesh model of the face. The domain of the combined image is given by the 2D parameterization of the mesh, such that every vertex of the 3D mesh has unique 2D coordinates in the parameter domain, yielding a one-to-one mapping between 2D and 3D mesh triangles. Each triangle of the 3D model that is covered by an image taken by one or more of the cameras is projected onto the image of the camera that observes it best, e.g., as determined by the dot product between the triangle normal and the camera direction. The camera pixels corresponding to the projection are then copied to the corresponding 2D triangle in the combined image. Optionally, to account for variations in brightness of images captured by different cameras various processing techniques may be applied such as Poisson image editing. For example, the process of Poisson editing can involve starting with the largest image patch and iteratively adding adjacent patches until the combined image is complete. For each new patch that is added, x- and y-gradients are computed inside the patch and used to solve a Poisson equation to find a new patch that matches the gradients as closely as possible, while also obeying the boundary conditions set by other completed patches. Optionally, in order to maintain continuity between images taken at different times (e.g., in order to avoid artifacts involving too extreme differences between consecutive combined images), previous images may be used to form per-pixel soft constraints when solving the Poisson equation involved in a certain combined image.

In some embodiments, data representing multiple images coming from a video stream of a camera is converted into feature values. Optionally, the feature values are represented as a vector of feature values. Optionally, the multiple images have a temporal relationship between them. For example, the images are successive images in the stream (i.e., they were generated one after the other) and/or the multiple images were all taken by the camera during a certain period. For example, the multiple images were all taken within a period lasting less than 0.1 seconds, less than 0.5 seconds, less than 3 seconds, or more than 3 seconds. Optionally, some of the feature values may be a function of multiple images (e.g., they may compare feature extracted from multiple images taken at different times).

In some embodiments, feature values are generated from multiple images. The multiple images include images belonging to multiple video streams (i.e., they are generated by multiple cameras). Additionally, the multiple images include images taken at different times (e.g., successive images from the same stream). Optionally, the multiple images include successive sets of corresponding images, which includes sets that may be ordered according to the time the images in each set were taken. Optionally, the feature values are represented as a vector of feature values. Optionally, some of the feature values include feature values that are a function of corresponding images from among the multiple images. Optionally, some of the feature values include feature values that are a function of successive images from among the multiple images.

Cameras coupled to a frame of an HMS worn by a user that are pointed to the user's face are typically very close to the user's face, with the distances between the camera to the face ranging from less than 1 cm to usually no more than 15 cm. Thus, portions of the user's face typically occupy a large portion of the images captured by the cameras, and even at times portions of the user's face can occupy the entire images. This is in contrast with other scenarios in which images of the users face are captured by a front facing camera (e.g., a webcam, a camera embedded in a TV, etc.) in which the face may occupy a smaller portion of the image. Additionally, due to the coupling the orientation and position of the cameras relative to the face does not significantly change (or change at all) event when the user's head performs angular motions or other movements in space. This means that images captured by a camera capture the same facial region of the user over long periods. This is different from many scenarios in which frontal cameras that are farther from the user capture images of the user. In such cases, the position and orientation of the face in images may change significantly as the user moves.

Some approaches routinely used in the art for acquiring feature values from images of faces involve additional elements that aim to ease the process of acquiring accurate feature values. In one example, markers are added to the face of a user, e.g., by paint (fluorescent or other), makeup, stickers, etc. Such markers on the face can be easily detected by image processing algorithms due to their different texture and/or color compared to the surrounding regions on the face. In another example, patterns may be painted on the face of a user and/or special makeup may be used in order to be able to better identify facial features and/or movements on the face (e.g., facial expressions). In another example, the face may be lighted in certain patterns (structured light) in order to assist in capturing facial features. For example, a projector may project a structured light pattern onto the face in order to provide dense surface texture, and/or the projector may project phase-shifted color-fringe patterns onto the face.

In some embodiments, none of the techniques mentioned above are utilized by systems and/or methods that involve acquiring facial feature values describing the face of a user and/or learning a model of the face of the user. That is, some embodiments described herein do not include a step or mechanism that involves placing markers on the face of the user (e.g., by applying paint or stickers), applying makeup in patterns designed to ease image processing tasks, or projecting structured light for (i.e., projecting certain patterns on the face). In other embodiments, some of the above techniques may be applied while others are not. For example, in one embodiment, no markers are place on the face, such as by applying black paint dots or stickers to the face. In another embodiment, makeup and/or paint is not applied to the face of the user in such a way that may assist in identifying facial features (e.g., contours of the face). In still another embodiment, the face of the user is not illuminated by structured light that projects certain patterns on the face of the user that may assist in extracting facial features from images of the face.

Registration is an initial step for many image processing tasks. When images include faces, the registration may also be referred to as facial registration. Facial registration typically involves identifying a face in an image and/or prominent facial features such as the corner of an eye, the tip of the nose, the edge of an eyebrow, the mouth, etc. Once facial registration is performed, the identified prominent features may be used to identify other points on the face. Additionally or alternatively, the identified features may be used to preprocess the image (e.g., move, rotate, and/or rescale) in order for the head and/or certain key points (e.g., the pupil) to be positioned in a certain place such that is shared by multiple images being processed. For example, to ease feature extraction from frontal images of a face, after facial registration each image is transformed such that nose appears in the middle of the image and the height of the face is a certain number of pixels (e.g., occupying 90% of the height of the image). While in may scenarios known in the art, facial registration may be a difficult task, due to the unique characteristics of the coupling of the cameras to the frame which enable a stationary position and orientation relative to the face, in some embodiments, facial registration is a relatively simple step to perform, while in other embodiments, this step might not even be performed at all.

In some embodiments, registration involves identifying a certain facial landmark and/or facial feature in an image. In one example, registration with images generated by an upward facing camera that is attached to a frame of an HMS may involve identifying the position of an eyebrow in the images (e.g., identifying the position of one or more edges of the eyebrow). In another example, registration with a downward facing camera attached to a frame of an HMS may involve identifying the position of an edge of the lip in the images. In still another example, registration with a camera attached to a frame of an HMS and oriented towards an eye may involve identifying the position of a pupil and/or an edge of an eye in the images. For the purpose of registration, various algorithms known in the art for identification of facial features can be used; examples of such algorithms are given below.

Some embodiments involve collecting a set of images of users taken while the users express various emotional responses. Optionally, the set includes images of one or more cameras that are not mounted to a frame of an HMS worn by users. For example, the images may include images captured by cameras that are at least 20 cm away from the face of the user, such as a Kinect and/or RGB camera in front of the user. Additionally or alternatively, the set may include images taken by one or more cameras coupled to a frame of an HMS worn by the users, were the cameras may be coupled to the frame at different locations and/or have different orientations, as discussed above. Optionally, the set of images is collected for training various predictors such as emotional response predictors (ERPs) discussed in this disclosure. Additionally or alternatively, the set of images is collected for training various facial feature identification modules mentioned in this disclosure, such as modules that identify action units, facial landmark locations, blendshape weights, and/or microexpressions. There may be various protocols for acquiring such data, which may involve verifying the data, extracting features from the data, and/or rewarding users for providing the data. Examples of such protocols are given in United States Patent Application 20150186912, titled "Analysis in response to mental state expression requests" filed on Mar. 16, 2015.

Identifying the facial features in the examples given above may be done in various ways known in the art. In particular, in some embodiments, machine-learning based algorithms may be used to identify the facial features in the images (e.g., an eye, an edge of the lip, edge of the nostril, location of an eyebrow, etc.) Such algorithms may use train a model utilizing annotated training data in which the facial features are identified. In one example, facial features may be identified using methods similar to the ones described in Milborrow, S., and Nicolls, F. (2008), "Locating facial features with an extended active shape model", in Computer Vision—ECCV, pp. 504-513. Active shape models typically deal with frontal views of faces, but these algorithms will work well for portions of faces and/or non-frontal perspectives, given appropriate training data (i.e., images corresponding to the specific position and/or orientation of the camera and with appropriately labeled landmarks). In another example, geometrical face models may be used to identify facial features, such as the models described in Jeng et al. "Facial feature detection using geometrical face model: an efficient approach." Pattern recognition 31.3 (1998): 273-282. Note that this reference describes models for frontal features in whole-face frontal views, but the same principles may be easily adapted by one skilled in the art to identify facial features in images of a camera that captures a portion of the face and/or does not necessarily provide a frontal view of the face. In another example, methods for identifying specific facial features may be utilized, such as the adaptations of the method for identifying eyes described in Lam, et al., "Locating and extracting the eye in human face images." Pattern recognition 29.5 (1996): 771-779.

It is to be noted, that due to the characteristics of the images generated by cameras so closely situation to the face, facial features in the images will tend to be significantly larger and more prominent than is typically encountered in the art. Thus, it becomes trivial for one skilled in the art to identify prominent features (e.g., an eyebrow that occupies half of an image) using various algorithms for object recognition that are known in the art.

In some embodiments, a facial feature recognition model may be trained using images of multiple users that include the facial feature. Optionally, the images are taken by cameras located at a similar position on a frame of an HMS worn by the users and/or the cameras have a similar orientation with respect to the users' faces. Optionally, such a model is considered a general facial feature identification model. Optionally, various general models may be created for users having certain characteristics involving one or more of the following: gender, ethnicity, skin color, facial hair, age, and/or facial augmentations. For example, a general model may be created for white males between the age of 21 and 40. In another example, a general model may be made for Asian female teenagers with braces. In yet another example, a general model may be made for bald bearded men.

In other embodiments, a facial feature recognition model may be trained using images of a certain user that include the facial feature. Optionally, the images are taken by a camera in a certain position on a frame of an HMS worn by the certain user and/or in a certain orientation with respect to the user's face. Optionally, such a model is considered a personal facial feature identification model.

In some embodiments, a personal facial feature identification model for a user may be initialized from general facial feature identification model appropriate for the user. For example, a model appropriate for the gender of the user or a combination of other characteristics mentioned above. Additional training samples for the user may be created by taking images and labeling them with facial features identified by the user's model. These training samples may be used to retrain the models to make them perform better when identifying facial features of the user.

In some embodiments, facial registration and/or preprocessing of images obtained utilizing a camera may involve various transformations such shifting scaling and/or rotating with respect to an identified facial feature (e.g., such that the facial feature may be located in a certain relative position, have a certain size, and/or certain orientation). In other embodiments, images may be preprocessed in order to adjust certain image properties such as brightness and/or improve image sharpness, contrast, etc.

In some embodiments, prior to feature extraction from images from a video stream, the images may undergo transformations such as rotation and/or scaling in order to produce an image that represents a (portion of a) frontal view of the face of the user.

Various types of feature may be derived from images from video streams and utilized in embodiments described herein for various purposes such as detecting affective response of a user and/or recreating facial expressions on an avatar. Generally, the feature values may be divided in two types: low-level features, and high-level facial-related features. The low-level features are features that are typically used in image processing and vision-related applications; they do not necessarily involve human faces, and are typically used for various applications such as general object and/or motion recognition. The high-level features are typically facial features that capture some aspect of faces or facial motion. Optionally, deriving high-level features utilizes domain knowledge of the face. High-level features may correspond to various aspects of the face. For example, they may correspond location of certain facial features (e.g., facial landmarks), certain movement patterns of facial muscles (e.g., action units and microexpressions), and/or a certain composition of a facial expression (e.g., blendshapes). While the high-level features in the literature are typically derived from whole images of the face (referred to herein as full frontal images), as explained below, these features can also be used with the type of images generated by cameras coupled to a frame of an HMS worn by a user.

It is to be noted that the categorization of features to high-level and low-level features is done purely to assist in distinguishing between groups of features. This is not a strict classification; various features that may be considered low-level in one embodiment may be considered high-level in another embodiment, and vice versa. In addition generating some low-level features may be done utilizing facial domain knowledge, and as such, in some cases, they may be considered high-level features.

Following are examples of various types of features and feature generation approaches that may be employed. This is not a comprehensive description; some embodiments may utilize other types of features that are not described below.

In some embodiments, feature values derived from images from video streams include various types of low-level features that are known in the art, which have been proven useful for various computer vision-related applications, but are not necessarily restricted to applications involving images that include the faces or body. Optionally, these features may be considered low-level features that do not require specific domain knowledge of the face to be generated. Nonetheless, many of the examples of features given below have been proven to work well with tasks involving human faces.

It is to be noted, that in typical applications that involve processing images of faces, the images being processed are full-face frontal images. However, the feature extraction techniques, and/or machine learning techniques they utilize (e.g., for identifying expressions), are agnostic to the fact that the source images are of a specific type (e.g., full-face frontal images). Thus, these techniques may be adapted easily by one skilled in the art, or even used as described in the references of the examples below, to generate feature values from multiple images, where not all the images may capture the same portions of the face, e.g., due to a different location and/or orientation of the camera.

In one example, applying one or more of the exemplary feature extraction techniques described below to inputs comprising images from multiple cameras may be done by creating a single image file from the multiple images concatenating the data representing the images, stitching the images one after the other, or placing them in a certain two dimensional arrangement. Optionally, multiple images may be combined by constructing a 2D image using mapping a mapping of the multiple images to a 3D mesh model of the face, as described above. Following this step, the single image may be provided to the algorithms described below instead of an image of a full face.

In another example, applying one or more of the exemplary feature extraction techniques described below to inputs comprising images from multiple cameras may be done by first applying the feature extraction techniques to each image to create a feature vector for the image. Following that, the feature vectors of the individual images may be combined (e.g., by concatenating them or in some other mode of combination) in order to produce a vector that represents the multiple images. This vector can then be used for various applications such as identification of facial expressions, determining emotional response, and/or mapping a facial expression to an avatar.

In some embodiments, features described below are extracted at certain positions that may be described as relative co-ordinates. In one embodiment, for at least some of the features, the co-ordinates are relative to image boundaries, and thus represent an absolute position in the image. For example, an absolute position may be if a feature is extracted from a pixel at location (120,100) in an image. In one embodiment, for at least some of the features, the co-ordinates are relative to the location of identified facial features and/or landmarks. For example, a feature may be extracted from a pixel in an image identified as being at the base of the right nostril.

It is to be noted that referring to a feature as being extracted from a pixel at a certain location does not limit the feature to being based on values related solely to that pixel. In various embodiments, features may be based on values of multiple pixels such a square patch (e.g., 3×3 pixels) covering a certain portion of the image or pixels that are within a certain distance from a certain pixel. When a feature is derived from multiple pixels and reference is given to a single location of a pixel, which typically indicates a reference point for the location of the multiple pixels (e.g., the center of a circular patch, or the center or corner of a square patch of pixels).

Following are some examples of feature extraction techniques known in the art that may be used in various embodiments described herein. Some of these techniques are considered to generate local features (i.e., they describe properties that are influenced by a relatively small region of an image). Other techniques generate features that describe properties of the whole images.

Gabor filters, which are utilized in some embodiments for feature extraction, are linear filters used for edge detection. Frequency and orientation representations of Gabor filters are similar to those of the human visual system, and they have been found to be particularly appropriate for texture representation and discrimination. Gabor filters have been used extensively for various image analysis applications. In particular, they have been found to useful in many applications concerning facial recognition and/or expression identification. Following are some examples of some of the ways Gabor filters may be used for feature extraction in some embodiments. In one example, Lyons et al. "Coding facial expressions with Gabor wavelets." Automatic Face and Gesture Recognition, 1998. Proceedings. Third IEEE International Conference on. IEEE, 1998, construct a facial expression coding for images using a multi-orientation multi-resolution set of Gabor filters which are topographically ordered and aligned with facial features. In another example, Bartlett et al. "Recognizing facial expression: machine learning and application to spontaneous behavior", Computer Vision and Pattern Recognition (CVPR), 2005, investigate various feature selection techniques and machine learning methods that may be applied to Gabor filter-based representations of images in order to successfully identify facial expression. And in yet another example, Gu et al. "Facial expression recognition using radial encoding of local Gabor features and classifier synthesis", Pattern Recognition 45.1 (2012): 80-91, describe multi-scale Gabor-filter operations performed on images. The resulting Gabor decompositions are encoded using radial grids. The codes are fed to local classifiers to produce global features, representing facial expressions. Experimental results show successful results of such image representation for facial expression identification using a hierarchical classifier.

Local Binary Patterns, which are utilized in some embodiments for feature extraction, are feature values used extensively in image processing applications, and specifically, have been used successfully for various facial recognition related applications. In one example, Ahonen et al. "Face description with local binary patterns: Application to face recognition" Pattern Analysis and Machine Intelligence, IEEE Transactions on 28.12 (2006): 2037-2041, describe efficient facial image representation based on local binary pattern (LBP) texture features. The images are divided into several regions from which the LBP feature distributions are extracted and concatenated into an enhanced feature vector to be used as a face descriptor. In another example, Shan, et al. "Facial expression recognition based on local binary patterns: A comprehensive study" Image and Vision Computing 27.6 (2009): 803-816, formulate Boosted-LBP to extract the most discriminant LBP features. The extracted features are used successfully for facial expression recognition using Support Vector Machine classifiers with Boosted-LBP features.

Various extensions and variations to LBP that may be used in embodiments described herein for feature extraction. In one example, Islam, M. "Local Gray Code Pattern (LGCP): A Robust Feature Descriptor for Facial Expression Recognition", in International Journal of Science and Research (IJSR) (2013), describes an extension of LBP called Local Gray Code Pattern (LGCP). LGCP characterizes both the texture and contrast information of facial components. The LGCP descriptor is obtained using local gray color intensity differences from a local 3×3 pixels area weighted by their corresponding TF (term frequency).

In one embodiment, the SIFT algorithm is used to extract local features from images. This algorithm is descried in further detail in U.S. Pat. No. 6,711,293, "Method and apparatus for identifying scale invariant features in an image and use of same for locating an object in an image". In another embodiment, the SURF algorithm may be used to extract features corresponding to points of interest in images, as described in further detail in US 20090238460, "Robust interest point detector and descriptor". In other embodiments, various extensions and/or modifications of these techniques may also be employed such as BRIEF described in Calonder et al., "Brief: Binary robust independent elementary features", in European Conference on Computer Vision, 2010, or ORB described in Rublee et al., "ORB: an efficient alternative to SIFT or SURF", IEEE International Conference on Computer Vision (ICCV), 2011.

In one embodiment, at least some of the feature values derived from an image of a portion of a face taken by a certain camera, which is mounted on a frame of an HMS in at certain position and/or in a certain orientation, are derived from positions of a set of keypoints identified in the image. For example, the set of keypoints may include a predetermined number of keypoints, such as 1, 2, 5, 10, 25, or some other value greater than 1. Optionally, the set of keypoints includes keypoints for which a certain objective function reaches a certain threshold (and as such, the number of keypoints may vary between images). Optionally, the keypoints are automatically selected according to a certain criterion (e.g., indicative in difference in shades of adjacent pixels), so they may not necessarily correspond to a certain predefined facial feature (e.g., an edge of the lip or an edge of the eye). Thus, keypoints may represent locations where shape variation is high in 3D faces, without the need to define what facial features are expected to be at those locations. There various methods for automatic selection of keypoints known in the art, which may be used in some embodiments. For example, Mian et al., "Keypoint detection and local feature matching for textured 3D face recognition", International Journal of Computer Vision 79.1 (2008): 1-12, describe an algorithm that automatically selects keypoints in an image utilizing and extracts descriptive 3D features from those images.

In one embodiment, at least some of the feature values derived from an image of a portion of a face taken by a certain camera, which is mounted on a frame of an HMS in at certain position and/or in a certain orientation, are Histograms of Oriented Gradients (HOG) descriptors. HOG descriptors are image descriptors invariant to 2D rotation that have been used in many different problems in computer vision. Hog descriptions are often extracted at salient regions such as locations of facial landmarks. Examples of methods for extracting HOG features that may be used in some embodiments are given in Déniz et al. "Face recognition using histograms of oriented gradients", in Pattern Recognition Letters 32.12 (2011): 1598-1603, and in the references cited therein.

In some embodiments, holistic methods developed for whole face applications can be used for portions of faces and/or oriented images of portions of faces too. One example of such an approach involves the feature extraction techniques used for Eigenfaces, which uses Principal Component Analysis (PCA). Another example of such an approach are the feature extraction techniques used for Fisherfaces, which are built on Linear Discriminant Analysis (LDA). Additional discussion about these techniques and their extension to be used with kernel-based method can be found in Ming-Hsuan, Y. "Kernel eigenfaces vs. kernel fisherfaces: Face recognition using kernel methods", in FGR '02 Proceedings of the Fifth IEEE International Conference on Automatic Face and Gesture Recognition, Page 215, 2002.

The dynamic nature of facial expressions involves phenomena that may be detected over periods of time (based on multiple images taken at different times) and which under certain conditions be less apparent when detected based on single frames. Thus, in some embodiments, a feature value may be derived from multiple images comprising sequential images taken during a certain period. For example, in some embodiments, the certain period may span a duration of 0.1 seconds, 0.25 seconds, 0.5 seconds, or 1 second. In other embodiments, the multiple images may include a certain number of consecutive video frames. It is to be noted that the term "sequential images" refers to images that were captured at sequential times, i.e., occurring one after the other, but not necessarily directly one after the other. Some examples of features having a temporal aspect are given in the references given above that discussed identifying landmarks and/or action units from multiple images. Some additional approaches that may be used for temporal features that are derived from sequential images are given below.

In one embodiment, at least some of the feature values derived from sequential images are generated using dynamic texture recognition. Dynamic texture is an extension of texture to the temporal domain. One example of dynamic texture recognition is given by Zhao and Pietikainen, "Dynamic texture recognition using local binary patterns with an application to facial expressions" in Pattern Analysis and Machine Intelligence, IEEE Transactions on 29.6 (2007): 915-928. In this reference, Zhao and Pietikainen describe a method for generating features by having textures modeled with volume local binary patterns (VLBP), which are an extension of the LBP operator widely used in ordinary image-texture analysis, combining motion and appearance. To make the approach computationally simple and easy to extend, only the co-occurrences on three orthogonal planes (LBP-TOP) are then considered. A block-based method is also proposed to deal with specific dynamic events, such as facial expressions, in which local information and its spatial locations should also be taken into account. A somewhat similar approach involving spatio-temporal features is described in Bihan, et al., "Action unit detection using sparse appearance descriptors in space-time video volumes", in IEEE International Conference on Automatic Face & Gesture Recognition and Workshops (FG 2011), 2011, which is discussed above in this disclosure.

In another embodiment, at least some of the feature values derived from sequential images are spatio-temporal features similar to the cuboids described in Dollar et al. "Behavior recognition via sparse spatio-temporal features", in 2nd Joint IEEE International Workshop on Visual Surveillance and Performance Evaluation of Tracking and Surveillance, 2005. Dollar et al. demonstrate methods for behavior recognition (including identifying facial expressions) by characterizing behavior in terms of spatiotemporal features called cuboids, which are local regions of interest in space and time (cuboids) which serve as the substrate for behavior recognition.

In yet another embodiment, at least some of the feature values derived from sequential images are optical strain-based features similar to the spatio-temporal strain values described in Shreve et al. "Macro- and micro-expression spotting in long videos using spatio-temporal strain", in IEEE International Conference on Automatic Face & Gesture Recognition and Workshops, 2011. The strain magnitude is calculated using the central difference method over the robust and dense optical flow field observed in facial regions a user's face.

In some embodiments, feature values derived from images from video streams are higher-level features. Optionally, the high-level features are derived with some domain knowledge involving the face. That is, computing the feature values is done while accounting for the fact that the images involve portions of a human face (e.g., utilizing knowledge of expected positions of certain features and/or the type of facial features to expect in certain images).

In computer vision research, facial landmarks are usually defined as the most salient facial points. Various sets of facial landmarks may be used to annotate images of faces. Example of facial landmarks used to annotate images are described in Köstinger et al., "Annotated facial landmarks in the wild: A large-scale, real-world database for facial landmark localization", in Computer Vision Workshops (ICCV Workshops), 2011. Other sets of landmarks, that include fewer or more landmarks than this example, may be used in various embodiments.

Some embodiments described herein involve images taken by cameras situated in various locations and/or orientations relative to the face. Thus, images from a first camera may be significantly different from images taken with a second camera. In some embodiments, this difference manifests itself with different corresponding sets of landmarks that are visible in images (i.e., in the FOVs of the cameras that took the images). In another embodiment, a second camera coupled to the frame near the bridge of the nose of the user and pointed at the left eye of the user may have landmarks 7, 8, and 9 in its FOV, but none of the other landmarks from the other side of the face, or those above the eye-line or below the tip of the nose (including it). In yet another embodiment, a third camera coupled to the frame at a location that is below the eye-line, left of the nose, and oriented downward may have certain lower-face landmarks in its FOV, such as 14, 15, 18, 19, and/or 21.

Identification of landmarks is an important step in many computer vision-related algorithms, such as face detection and/or alignment. Facial landmarks are also used in many applications as features that are utilized for identifying facial expressions and/or emotional response, and for mapping facial expressions to avatars. As such, identification of facial landmarks has received much attention in research community and there are various approaches to this task known in the art, including successful algorithms for identifying landmarks from images taken in various uncontrolled conditions ("in the wild"), involving images with possibly varying scale, orientation, focus, and/or brightness. Additionally, some algorithms are trained to identify locations of occluded landmarks (e.g., that may be occluded by hair or objects obstructing the line-of-sight to the camera).

A common approach used in many landmark identification algorithms involves the training of machine learning-based models using a training set of annotated images, which are images for which the location of at least some of the landmarks are marked. After training such a model, new images may be provided to a detector that utilizes the model in order for it to identify landmarks in the new images. The fact that the images and landmarks involve faces is typically accounted for by the nature for the training set of images and annotations that is provided. For example, typically the algorithms do not need additional information about physiology of faces encoded in them, beyond the images and landmarks that are given in the training set. Therefore, in some embodiments, the algorithms known in the art may be utilized "as is", or utilized after slight modifications that would be apparent to one skilled in the art, in order to identify facial landmarks in images obtained by cameras that are coupled to a frame of an HMS worn by a user. This being despite the fact that the images obtained by the cameras may be only of a portion of the face of the user and/or taken from perspectives that do not provide a frontal view of the face.

In some embodiments, a landmark identifier is a module that receives an image taken by a camera coupled to a frame of an HMS worn by a user and identifies the location of facial landmarks. The landmark identifier utilizes a machine learning-based algorithm that is trained to identify landmarks in the images taken by the camera. Optionally, the camera is one of the cameras described above in this disclosure, which generates one of the one or more video streams mentioned above. For example, the camera may be coupled to the frame at a location that is to the right of the symmetry axis that divides the face to the right and left sides, and is less than 15 cm away from the middle of the user's right eyebrow. In another example, the camera may be coupled to the frame at a location that is to the right of the symmetry axis and less than 10 cm away from the user's right upper lip. In a similar manner to these examples, the camera may be coupled to locations on the left side of the face as well.

Various approaches and machine learning algorithms may be used to train the landmark detector. Examples of algorithms used with full face and/or frontal images of faces, which may be utilized (possibly after adaptation by one skilled in the art), are given below. One thing that is often needed to train the landmark detector is a labeled training set. The labeled training set contains images taken by the camera coupled to the frame of the HMS, and identification of landmarks on those images. Optionally, images in a training set may contain images of multiple users, in multiple conditions (e.g., different lighting conditions) and/or while making different facial expressions (e.g., expressing different emotions). Having a diverse set of images included the training set of a landmark detector can help improve its generalizability, making it more likely to accurately identify landmarks in unseen images that were not included in the training set. Alternatively, images in a training set used to train the landmark identifier may mostly contain images of a certain user in order to train a landmark identifier that works well with images of the certain user.

It is to be noted that while in some embodiments, the landmarks that are used may come from the set of landmarks that is typically used for face analysis applications. In other embodiments, due to the camera perspective that may involve various locations on the frame and/or orientations of various angles, the set of landmarks used may differ from landmarks typically used with full frontal views of faces. For example, in some embodiments, certain landmarks that are typically used may be inappropriate, e.g., due to their lack of distinguishing features in images taken at certain angles. In other examples, the perspective of the camera may cause certain points that are typically not considered landmarks to be easily identifiable in multiple images (and thus they may be considered good candidates for landmarks).

In one embodiment, a separate machine learning-based model is trained for each specific location and/or orientation a camera coupled to the frame of an HMS may be in. Optionally, each model is trained with a training set that includes images taken by a camera in the specific location and/or orientation.

Obtaining images for a training set for training the landmark identifier is typically straightforward and involves acquiring images of a user's face from cameras coupled to a frame of an HMS while the user wears the frame. Optionally, the images may be converted to feature values. The feature values may include of various types described below, such as low-level features derived using Gabor filters, local binary patterns and their derivatives, features derived using algorithms such as SIFT, SURF, and/or ORB, image keypoints, HOG descriptors and features derived using PCA or LDA. Other examples of features may include features derived from sequences of images taken at different times, such as volume local binary patterns (VLBP), cuboids, and/or optical strain-based features that are mentioned in this disclosure. In addition to deriving feature values from images, for training, the images need to be assigned with labels describing the locations of the facial landmarks on the images. Labels may be provided in different embodiments in various ways. Some examples are given below.

In one embodiment, labels are marked by an expert. For example, the expert may be a human that views images taken by a camera coupled to a frame of an HMS at a certain location and/or orientation and indicates the positions of one or more landmarks on the images. Optionally, the expert may mark the positions on the images (e.g., on a touchscreen), and/or record coordinates of the landmarks in a file.

In other embodiments, an automatic labeling method may be employed to mark facial landmarks on images taken by a camera coupled to a frame of and HMS in a certain location and/or orientation. One example of an automatic landmark labeling system for such images involves an additional camera that takes a frontal image of the user. The camera that takes a frontal image may be any camera that takes an image of the face of the user from an optical distance of at least 20 cm from the face. For example, the camera that takes the frontal images may be embedded in a smartphone held by the user, a webcam, and/or a camera belonging to an entertainment system (e.g., Microsoft's Kinect or a camera embedded in a TV). In another example, the camera that takes the frontal image may be a camera of another user (e.g., mounted to the other user). In still another example, the camera may be mounted to the user, such as a camera that gives an image corresponding to the line of the sight of the user, but in this case, in order to get a frontal image of the user, the user stands in front of a mirror. The frontal images of the user may be used to identify facial landmarks using algorithms known in the art. Examples of such algorithms are given below.

In order to obtain less obstructed frontal images of the user, in some embodiments, certain elements such as lenses and/or displays may be removed from the HMS when frontal images of the user are acquired. In one embodiment, in a virtual reality display, the frontal panel containing the display may be removed while training images are acquired. For example, the frontal panel of an HMS built on Oculus Rift system may be removed. In another example, images may be acquired with a HMS that involves a smartphone while the user only wears the HMS without the smartphone (e.g., a system built upon Samsung Gear without a smartphone inserted in the HMS). In another example, lenses involved in a holographic augmented reality display, such as one built on Microsoft's HoloLens may be removed while the frontal images are taken. In other embodiments, for training, a user may wear a special frame with cameras coupled to it in locations and/or orientations similar to their locations and/or orientations on an HMS, but without additional elements of the HMS that may obstruct a frontal view of the user. Optionally, corresponding images taken by cameras couples to the frame may be modified (e.g., cropped) in mimic obstructions that the views of the cameras coupled to the frame of the HMS may have, but which are not present in images acquired when the cameras are coupled to the special frame.

The frontal images of the user may be used, in some embodiments, to identify facial landmarks using one or more of the automated methods known in the art, of which some examples are given below. In one example, the location of a landmark identified in the frontal image may be mapped to a location in an image taken at the same time the frontal image was taken (e.g., within 50 milliseconds of that time), by a camera coupled to a frame of an HMS worn by the user, where the camera has a specific location on the frame and/or a specific orientation towards the user. The mapping of the locations from the frontal image to the image of the camera coupled to the frame may be done by performing a transformation (e.g., which includes a rotation and scaling) that corresponds to the specific location and/or the specific orientation.

In some embodiments, a projected grid is utilized in order to assist with the mapping of facial landmarks identified on a frontal image to locations on images taken by cameras coupled to a frame of an HMS. Optionally, the projected grid may be similar to the grids used by various depth perception systems such as ones included in Microsoft's Kinect or Intel's RealSense. In one example, the projected grid is a lattice projected in IR, such that the grid may be detected, both by a camera in a frontal position and by cameras coupled to the frame of the HMS worn by the user. After observing the location on the grid of a landmark identified in the frontal image, it is possible to identify the corresponding location on the grid on an image taken by a camera that has a different FOV (e.g., due to its close proximity and sharp angle relative to the user's face). Optionally, the camera mounted to the frame may capture an additional image that does not include the grid (e.g., taken a millisecond after the projection of the grid is performed), in order to provide an image that does not include the grid, which can be used for training the landmark detector.

Following are some examples of approaches for landmark detection known in the art, which may be used to detect landmarks in frontal images of the user. These approaches can also be adapted by one skilled in the art, or even used without any adaptation, to identify landmarks in images of a user captured by cameras coupled, at various locations and/or orientations, to a frame of an HMS worn by the user.

In some embodiments, landmarks may be identified utilizing a separate detector for each landmark (e.g., a detector for the right pupil, a detector for the left nostril, etc.) For example, the AdaBoost based detectors and its modifications have been frequently used for this task, as described in Viola and Jones, "Robust real-time face detection" in Int. Journal of Computational Vision 57(2), 151-173 (2004). Examples of various detectors for individual landmarks are given in Castrillón et al. "A comparison of face and facial feature detectors based on the Viola-Jones general object detection framework" in Machine Vision and Applications 22.3 (2011): 481-494.

In other embodiments, when identifying locations of landmarks, a detector takes into account the relationship between multiple landmarks, such as pairwise distances between multiple landmarks. In one example, a variant of the Active Appearance Models (AAM), described in Cootes, et al. "Active appearance models", IEEE Transactions on Pattern Analysis & Machine Intelligence 6 (2001): 681-685, may be used for identifying landmarks. An AAM uses a joint statistical model of appearance and shape. Detectors that utilize AAM can identify a dense set of facial features, allowing extraction of whole contours of facial parts like eyes, etc. In another example, detecting landmarks in images depicting portions of a face may be done utilizing a detector of facial landmarks based on the Deformable Part Models, as described in Uřičář et al., "Detector of facial landmarks learned by the structured output SVM", VISAPP 12 (2012): 547-556. Uřičář et al. treat the task of landmark detection as an instance of the structured output classification problem and learn the parameters of the detector from data by the Structured Output Support Vector Machines algorithm (that receives labeled images as a training set). In yet another example, a detector for facial landmarks may utilize a graph matching approach, such as the one described in Zhou et al. "Exemplar-based Graph Matching for Robust Facial Landmark Localization", in IEEE International Conference on Computer Vision (ICCV), 2013.

After landmarks are detected on images from video streams of one or more cameras coupled to a frame of an HMS, these landmarks can be used to devise various feature values. In one example, the absolute location of a certain landmarks may be converted into a feature value. For example, the location of a pixel representing the center of a landmark (e.g., the edge of the mouth) may be used as a feature value. In another example, the difference between two or more landmarks may be converted into a feature value. For example, a feature value may correspond to the distance between the edge of the nostril and the edge of the lips (for a certain side of the face). In still another example, a set of landmark locations may be converted into feature values (e.g., by projecting the data according to eigenvectors found with PCA).

In some embodiments, feature values may involve landmarks in multiple corresponding images. For example, a feature value may correspond to the difference in height between the left and right eyebrows, when the landmark of each eyebrow appears in a different image (e.g., the landmarks for the left and right eyebrows appear in images taken by up-facing cameras couple to a frame to the left and right of the user's nose, respectively). Optionally, in order to derive features from landmarks in multiple images taken with different cameras, the images may be combined in various ways, and the features are derived from an image representing the combination of the multiple images. For example, the multiple images may be stitched one after the other, or arranged in a certain 2D arrangement, and distances between different landmarks may be determined according to their distance in the combined image. In another example, multiple partial images of a face may be combined into a single image by mapping the multiple images to a 3D mesh model, as described above in this disclosure.

In some embodiments, feature values may involve landmarks in sequential images, such as images taken at different times by the same camera. Such features can track how the location of certain landmarks changes with time, in order to help identify certain action units and/or facial expressions.

Determining emotional response and/or modelling facial expressions may involve feature values that rely on identification of certain types of facial movements that can change the appearance of the face, which are referred to as Action Units. Ekman and Friesen "The Facial Action Coding System: A Technique For The Measurement of Facial Movement", Consulting Psychologists Press, Inc., San Francisco, Calif., 1978, describe the Facial Action Coding System (FACS) for describing facial expressions by action units (AUs). Of 44 FACS AUs that they defined, 30 AUs are anatomically related to the contractions of specific facial muscles: 12 are for upper face, and 18 are for lower face. AUs can occur either singly or in combination. When AUs occur in combination they may be additive, in which the combination does not change the appearance of the constituent AUs, or non-additive, in which the appearance of the constituents does change. Although the number of atomic action units is relatively small, a large number of combinations of AUs may be observed. FACS provides descriptive power often needed to describe the details of facial expression. In some embodiments, other methods of taxonomizing human facial movement may be used, one of them being an updated version of FACS described in Ekman et al., "Facial Action Coding System: The Manual on CD ROM", A Human Face, Salt Lake City, 2002.

There are various methods known in the art that may be used to identify AUs from video streams. While the methods are typically utilized for full frontal views of faces, as discussed above with regards to facial landmarks, these methods can be used without change, or with slight modifications that would be known to one skilled in the art, in order to identify action units in images taken by cameras coupled to a frame of an HMS as described in this disclosure. The main difference between using these approaches for identifying AUs from images taken by cameras coupled to a frame of an HMS, and the way they are used in the examples below, would be the nature of the training set provided. For example, instead of involving video images of full frontal views of faces, the training images would typically include images from video streams generated by the cameras coupled to frame, which may be different in their nature (e.g., include portions of the face and/or displaying the face from perspectives that are significantly different from a frontal view). Nonetheless, even with the different type of images, the algorithmic steps described in the references below can be used with the different type of images.

Following are some examples of algorithmic approaches that may be used by an action unit identifier; other approaches, not mentioned below, may also be utilized in some embodiments described herein. The approaches below include both static modeling, which is typically posed as a discriminative classification problem in which each video frame is evaluated independently, and temporal modeling, in which frames are segmented into sequences and typically modeled together in order to identify AUs occurring over multiple frames.

In one example, identifying AUs may be done utilizing one or more of the methods described in Bartlett, et al., "Measuring facial expressions by computer image analysis", in Psychophysiology, 36:253-264, 1999. Bartlett et al. describe applications of computer image analysis to the problem of automatically detecting facial actions in sequences of images. They compare three approaches: holistic spatial analysis, explicit measurement of features such as wrinkles, and estimation of motion flow fields. The three methods were also combined in a hybrid system that classified six upper facial actions.

In another example, identifying AUs may be done utilizing one or more of the methods described Tian et al. "Recognizing Action Units for Facial Expression Analysis", in IEEE Transactions on Pattern Analysis and Machine Intelligence, 23.2 (2001): 97-115. Tian et al. describe an Automatic Face Analysis (AFA) system to analyze facial expressions based on both permanent facial features (brows, eyes, mouth) and transient facial features (deepening of facial furrows). The AFA system recognizes fine-grained changes in facial expression into action units (AUs) of the Facial Action Coding System (FACS), instead of a few prototypic expressions. Multi-state face and facial component models are proposed for tracking and modeling the various facial features, including lips, eyes, brows, cheeks, and furrows.

In still another example, identifying AUs may be done utilizing one or more of the methods described in Valstar and Pantic, "Fully automatic facial action unit detection and temporal analysis", in IEEE Conference on Computer Vision and Pattern Recognition Workshop, 2006. Valstar and Pantic describe methods in which AUs are identified using a set of spatio-temporal features calculated from tracking data for 20 facial landmarks points that are detected using a facial point localization method that uses individual feature GentleBoost templates built from Gabor wavelet features. Additionally, the facial landmarks are tracked using a particle filtering scheme that uses factorized likelihoods and a model that combines a rigid and a morphological model. The AUs displayed in the input video and their temporal segments are identified by Support Vector Machines trained on a subset of most informative spatio-temporal features selected by AdaBoost.

In still another example, identifying AUs may be done utilizing one or more of the methods described in Bihan, et al., "Action unit detection using sparse appearance descriptors in space-time video volumes", in IEEE International Conference on Automatic Face & Gesture Recognition and Workshops (FG 2011), 2011. Bihan et al. describe various methods for identifying AUs, which involve Local Binary Patterns (LBP) or Local Phase Quantization (LPQ). Since facial expressions (and the AUS they involve) are inherently dynamic processes, the method include temporal extensions of LBP and LPQ to account for the temporal dynamics.

As the examples above demonstrate, a common approach used in many action unit (AU) identification algorithms involves the training of machine learning-based models using a training set of annotated images, which are images for which the relevant AUs are identified. After training such a model, new images may be provided to a detector that utilizes the model in order for it to identify AUs. The fact that the images and AUs involve faces is typically accounted for by the nature for the training set of images and annotations that are provided. Therefore, in some embodiments, the algorithms known in the art may be utilized "as is", or utilized after slight modifications that would be apparent to one skilled in the art, in order to identify AUs in images obtained by cameras that are coupled to a frame of an HMS worn by a user. One example of a modification that may be done is to utilize different preprocessing steps. For example, instead of using a landmark identification algorithm designed for full frontal images of a face, an approach suitable for identifying landmarks in images taken with cameras coupled to the frame of the HMS may be used.

In some embodiments, an AU identifier is a module that receives a set of images comprising one or more images taken by one or more cameras coupled to a frame of an HMS worn by a user and identifies which AUs are expressed in the images. The AU identifier utilizes a machine learning-based algorithm that is trained to identify AU in the images taken by the camera. Optionally, the one or more camera are described above in this disclosure, and they generate the one or more video streams mentioned above. For example, a camera from among the one or more cameras may be coupled to the frame at a location that is to the right of the symmetry axis that divides the face to the right and left sides, and is less than 10 cm away from the middle of the user's right eyebrow. In another example, the camera may be coupled to the frame at a location that is to the right of the symmetry axis and less than 10 cm away from the user's right upper lip. In a similar manner to these examples, the camera may be coupled to locations on the left side of the face as well.

In one embodiment, AUs are identified from samples, with each sample being derived from a set of images taken from a single camera. For example, the set of images may include sequential images taken during a certain period (e.g., 0.5 seconds) from a certain camera coupled to a frame of an HMS worn by a user. It is to be noted, that due to the dynamic nature of AUs, at least some of the features may be derived from multiple temporally successive images, e.g., to reflect properties related to facial movements involved in AUs.

In another embodiment, AUs are identified from samples, with each sample being derived a set of images taken from multiple cameras. For example, the set of images may include sequential sets of corresponding images taken during a certain period (e.g., 0.5 seconds) from multiple cameras coupled to a frame of an HMS worn by a user. In this example, each camera is coupled to the frame at a certain location and/or has a certain orientation to the face, which is different from the location and/or orientation of the other cameras. When features are extracted in order to identify the action units, they may be extracted from each image independently and/or jointly from multiple images (in a similar fashion to the way described above in which features may be generated for landmark identification). Additionally or alternatively, as explained above, certain feature values may be extracted from multiple temporally successive images, e.g., to reflect properties related to facial movements involved in AUs.

In some embodiments, images in a training set used to train the AU identifier may contain images of multiple users, in multiple conditions (e.g., different lighting conditions) and/or while making different facial expressions (e.g., expressing different emotions). Having a diverse set of images included the training set of a landmark detector can help improve its generalizability, making it more likely to accurately identify landmarks in unseen images that were not included in the training set. In other embodiments, images in a training set used to train the AU identifier may mostly contain images of a certain user in order to train an AU identifier that works well with images of the certain user.

Obtaining images for a training set for training the AUs identifier is typically straightforward and involves acquiring images of a user's face from cameras coupled to a frame of an HMS while the user wears the frame. These images may be converted to samples comprising feature values. The feature values may include various types such as features derived from locations of landmarks in the images and/or low-level features described above, such as features derived using Gabor filters, local binary patterns and their derivatives, features derived using algorithms such as SIFT, SURF, and/or ORB, image keypoints, HOG descriptors, and features derived using PCA or LDA. Other examples of features may include features derived from multiple images taken at different times, such as volume local binary patterns (VLBP), cuboids, and/or optical strain-based features. In addition to deriving feature values from images, for training, samples derived from the images need to be assigned with the locations of the facial landmarks on the images. Labels may be provided in different embodiments in various ways. Some examples are given below.

In one embodiment, labels are marked by an expert. For example, the expert may be a human that views images taken by one or more camera coupled to a frame of an HMS at a certain location and/or orientation and indicates which AUs appear to have occurred in the images. For example, the expert may mark identify which AUs were expressed in images. Optionally, the human expert may view frontal images of the user taken at the same time as the images from the cameras coupled to the HMS were taken, and determine which AUs occurred based on those images. A human expert may be more capable of accurately determining AUs from the standard frontal images that are more frequently encountered in the art.

In one embodiment, some of the images provided for training may be premeditated. For example, a user may be asked to move certain facial muscle and/or make certain facial expressions while the images are taken by the one or more cameras coupled to the frame. In such a case, the labels (i.e., which AUs occurred) may be assumed to be the AUs the humans typically perform when moving the certain facial muscles and/or making the certain facial expressions.

In other embodiments, an automatic labeling method may be employed to identify AUs in a set of images comprising one or more images taken by one or more cameras coupled to a frame of an HMS worn by a user. One example of an automatic AU labeling system for such images involves an additional camera that takes frontals image of the user. The camera that takes frontal images may be any camera that takes images of the face of the user from an optical distance of at least 15 cm from the face. For example, the camera that takes the frontal images may be embedded in a smartphone held by the user, a webcam, and/or a camera belonging to an entertainment system (e.g., Microsoft's Kinect or a camera embedded in a TV). In another example, the camera that takes the frontal image may be a camera of another user (e.g., mounted to an HMS of the other user). In still another example, the camera may be mounted to the user, such as a camera that gives an image corresponding to the line of the sight of the user, but in this case, in order to get a frontal image of the user, the user stands in front of a mirror. The frontal images of the user may be used to identify AU using algorithms known in the art. Examples of such algorithms are given above. Optionally, in order to obtain less obstructed frontal images of the user, in some embodiments, certain elements such as lenses and/or displays may be removed from the HMS when frontal images of the user are acquired, as discussed above in the discussion related to obtaining frontal images for training a landmark identifier.

Given training samples and corresponding labels describing the AUs appearing in the images from which the samples are derived, various machine learning algorithms may be used to train the AU identifier, such as SVMS, multiple kernel learning, and/or other machine learning algorithms known in the art. The AU identifier may then be used to identify AUs in samples derived from images for which the label (AU) is unknown.

Determining emotional response and/or modelling (and rendering) facial expressions may involve feature values that express the extent different basic facial expressions are being expressed by the user. That is, every facial expression the user makes may be approximated by a combination (e.g., a linear combination) of the basic expressions. Optionally, each basic expression may represent a certain 3D model of a face expressing the basic expression. One family of models that are formulated according to this principle are blendshape models.

A blendshape model generates a facial pose as a linear combination of a number of facial expressions, the blendshape "targets". By varying the weights of the linear combination, a range of facial expressions can be expressed with little computation. The set of shapes can be extended as desired to refine the range of expressions that the character can produce. One advantage that some blendshapes models have is that blendshapes have asemantic parameterization: the weights have intuitive meaning corresponding to the strength or influence of the various facial expressions. Additionally, to some extent blendshapes force facial expressions to stay "on model", that is, arbitrary deformations to the face are not possible with these models. This helps to maintain facial character and avoid deformation artifacts that may occur while rendering an avatar to mimic a user's facial expressions. Blendshapes are discussed in further detail in Lewis et al., "Practice and Theory of Blendshape Facial Models", in EUROGRAPHICS 2014.

One example of a blenedshape model, which may be utilized in some embodiments, is given by Bouaziz et al., "Online modeling for real-time facial animation", in ACM Transactions on Graphics (TOG), 32.4 (2013): 40. The blendshape model of Bouaziz et al. includes a set of blendshape meshes where $B=[b_0, \ldots, b_n]$, where $b_0$ is the neutral pose and the $b_i$, for $i>0$ define specific base expressions. All blendshapes have the same static mesh combinatorics and are represented by stacked coordinate vectors. A new facial expression is generated a weighted function $F(x)=b_0+\Delta Bx$, where $\Delta B=[b_1-b_0, \ldots, b_n-b_0]$, and $x=[x_1, \ldots, x_n]^T$ are blendshape weights bounded between 0 and 1. The blendshape representation may be well suited, in some embodiments, for real-time performance capture because it may reduce tracking to estimating the rigid head alignment and then blendshape weights for each frame. Optionally, the blendshapes $b_i$ can be chosen to match predefined semantics of common face animation controllers, e.g., mouth-open, smile, frown, etc., which may simplify certain processes as post-editing and animation retargeting.

In some embodiments, blendshape weights are derived from images generated by one or more video streams, with each video stream being generated by a camera coupled to a frame of an HMS worn by a user. From the blendshape weights one or more feature values are derived which represent the facial expression of the user. Optionally, the blendshape weights may serve as feature values. Additionally or alternatively, the feature values may be functions of the blendshape weights. As described in Bouaziz et al. above, and in other references mentioned in this disclosure, determining blendshape weights typically utilizes frontal facing cameras that may optionally have depth measuring capabilities (e.g., RGB-D cameras or systems that use IR grids, such as Microsoft's Kinect). Many of the embodiments described herein involve cameras that are coupled a frame of an HMS and are close to the face and/or are oriented at an angle that does not provide a frontal view of the face. When the input of images from video streams come from such cameras coupled to the frame, approaches known in the art for determining blendshape weights may not work well, or may not be applicable at all due to the different nature of the images (compared to the type of images the approaches were originally designed for). Therefore, in order to be able to assign blendshape weights that represent a facial expression of a user from images of the user taken with one or more cameras coupled to the frame of an HMS worn by the user, in some embodiments, the blendshape weights are predicted utilizing a blendshape weight predictor.

In one embodiment, the blendshape weight predictor is a machine learning-based predictor that receives samples comprising feature values that are derived from images taken with the one or more cameras coupled to a frame of an HMS worn by a user. The blendshape weight predictor computes, based on the feature values, weights of one or more blendshapes that correspond to the facial expression depicted in the images taken with the one or more cameras. Optionally, the feature values may be various features described in this disclosure. Examples of the features include high-level facial-related feature values and their derivatives such as location and dimensions of facial features and/or landmarks, and/or identification of action units (AUs) or microexpressions in images. Other examples of features include various low-level features such as features derived using Gabor filters, local binary patterns (LBP) and their derivatives, HOG descriptors, features derived using algorithms such as SIFT, SURF, and/or ORB, image keypoints, and features derived using PCA or LDA. Additional examples of features may also include features derived from multiple images taken at different times, such as volume local binary patterns (VLBP), optical strain-based features, and/or cuboids that are described in this disclosure.

In one embodiment, training a blendshape weight predictor can be done according to the teachings of Romera-Paredes et al., "Facial expression tracking from head-mounted, partially observing cameras", in IEEE International Conference on Multimedia and Expo (ICME), 2014. Romera-Paredes et al. derive feature values from images of cameras coupled to an HMS to extract features (e.g., LBP described in this disclosure). Ground-truth values of blendshape weights are obtained using a Kinect camera. They also explore various machine learning algorithms that may be used to create the predictor of blendshape weights.

Facial microexpressions are rapid involuntary facial expressions that may reveal suppressed affect. These are typically very rapid (e.g., ¼ to ¹⁄₂₅ of a second) involuntary facial expressions which give a brief glimpse to feelings that people have, but may be trying not to express. In some embodiments, microexpressions are identified from images generated by one or more video streams, with each video stream being generated by a camera coupled to a frame of an HMS worn by a user. Optionally, the microexpressions are identified by a module called a microexpression identifier. Optionally, identified microexpressions may be utilized to derive feature values that may be utilized for various applications such as determining emotional response and/or rendering an avatar expressing facial expressions of a user. Thus, in some embodiments, microexpressions may serve as feature values in a similar capacity to facial landmarks, action units, and/or blendshape weights, which are mentioned above. Additionally or alternatively, the microexpressions themselves may be an end product of a system in some embodiments described herein. An example of such a system may be a system that is configured to identify certain microexpressions from video streams generated by a plurality of cameras coupled to a frame of an HMS worn by a user.

In one embodiment, the microexpression identifier is a machine learning-based predictor that receives samples comprising feature values that are derived from images taken with the one or more cameras coupled to a frame of an HMS worn by a user. The microexpression identifier determines, based on the feature values, which microexpressions were expressed in the images taken with the one or more cameras, where the feature values may be various high-level and low-level features described in this disclosure, or other types of features derived from images. Examples of high-level features include facial-related values and their derivatives such as location and dimensions of facial features and/or landmarks, and/or identification of action units (AUs) in images. Other examples of features include low-level features such as features derived using Gabor filters, local binary patterns and their derivatives, features derived using algorithms such as SIFT, SURF, and/or ORB, image keypoints, HOG descriptors, and features derived using PCA or LDA. Other examples of features include features derived from multiple images taken at different times, such as volume local binary patterns (VLBP), optical strain-based features, and/or cuboids that are described in this disclosure. Additional examples of types of features, and how they may be used for identification of microexpressions is given in the examples below describing methods known in the art for identifying microexpressions.

There are various methods known in the art that may be used to identify microexpressions from video streams. While the methods are typically utilized for full frontal views of faces, these methods may be adapted by one skilled in the art, in order to identify microexpressions in images taken by cameras coupled to a frame of an HMS as described in this disclosure. The main difference between the way these approaches are used in the examples below, and how they are used in embodiments herein, would be the nature of the training set provided. For example, instead of involving video images of full frontal views of faces, the training images would typically include images from video streams generated by the cameras coupled to frame, which may be different in their nature (e.g., include portions of the face and/or displaying the face from perspectives that are significantly different from a frontal view). Additionally, different types of features and/or feature extraction techniques may be utilized in order to provide feature values from images taken by cameras coupled to the frame of the HMS.

Following are some examples of algorithmic approaches that may be used by an action unit identifier; other approaches, not mentioned below, may also be utilized in some embodiments described herein.

In one example, identifying microexpressions may be done utilizing the teachings of Pfister et al. "Recognising spontaneous facial micro-expressions", in IEEE International Conference on Computer Vision (ICCV), 2011. Pfister et al. introduce a framework that involves temporal interpolation to counter short video lengths, spatiotemporal local texture descriptors (e.g., LBP-TOP mentioned further below) to handle dynamic features and various machine learning approaches, such as SVMS, multiple kernel learning and random forests to classify sets of images to microexpression categories. In addition, Pfister describe a protocol for collecting a training corpus of expressions that are involuntary, and introduce temporal interpolation using graph embedding to enable identification of microexpressions with images from a standard 25 fps camera.

In another example, identifying microexpressions may be done utilizing the teachings of Shreve et al., "Macro- and micro-expression spotting in long videos using spatio-temporal strain", in IEEE International Conference on Automatic Face & Gesture Recognition and Workshops, 2011. Shreve et al. introduce features based on the strain impacted on the facial skin due to the nonrigid motion caused during facial expressions. The strain magnitude is calculated using the central difference method over the robust and dense optical flow field observed in facial regions a user's face.

In yet another example, identifying microexpressions may be done utilizing the teachings of Wang et al., "Face recognition and micro-expression recognition based on discriminant tensor subspace analysis plus extreme learning machine", in Neural processing letters 39.1 (2014): 25-43. Wang et al. describe a recognition technique for microexpressions that is based on Discriminant Tensor Subspace Analysis (DTSA) and Extreme Learning Machine (ELM). 2D face images are first dimensionally reduced using DTSA to generate discriminant features, then the reduced features are fed into the ELM classifier to analytically learn an optimal model for recognition.

In still another example, identifying microexpressions may be done utilizing the teachings of Lu et al., "A Delaunay-Based Temporal Coding Model for Micro-expression Recognition", in Computer Vision-ACCV 2014 Workshops. Lu et al. describe a Delaunay triangulation-based temporal coding model (DTCM), which is used to generate features that encode texture variations corresponding to muscle activities on face due to dynamical microexpressions.

As the examples above demonstrate, a common approach used in many microexpression identification algorithms involves the training of machine learning-based models using a training set of annotated sequences of images, which are sequences of images for which the relevant microexpressions are identified. After training such a model, new images may be provided to a microexpression detector that utilizes the model in order for it to identify microexpressions. The fact that the images and microexpression involve faces is typically accounted for by the nature for the training set of images and annotations that are provided. Therefore, in some embodiments, the algorithms known in the art may be utilized after modifications that would be apparent to one skilled in the art, in order to identify microexpressions in images obtained by cameras that are coupled to a frame of an HMS worn by a user. One example of a modification that may be done is to utilize various preprocessing steps, such as identifying landmarks, which are suitable for images taken with cameras coupled to the frame of the HMS, and are described above.

In some embodiments, a microexpression identifier is a module that receives a set of images comprising one or more images taken by one or more cameras coupled to a frame of an HMS worn by a user and identifies which microexpression (if any) was expressed in the set of images. The microexpression identifier may utilize a machine learning-based algorithm that is trained to identify microexpressions in a set of images taken by the camera. Typically, the set of images comprises images taken during a period of at least 0.05 seconds, and at most, 0.5 seconds. Optionally, the microexpression identifier may process images in a sliding window on a video stream (i.e., a temporal window of a certain length that spans a certain portion of the stream). Thus, a given video stream may be evaluated many times in order to identify microexpressions, when each time, a different portion (window) is evaluated.

In one embodiment, one or more cameras, as described above, generate one or more video streams as mentioned above. For example, a camera from among the one or more cameras may be coupled to the frame at a location that is to the right of the symmetry axis that divides the face to the right and left sides, and is less than 10 cm away from the middle of the user's right eyebrow. In another example, the camera may be coupled to the frame at a location that is to the right of the symmetry axis and less than 10 cm away from the user's right upper lip. In a similar manner to these examples, the camera may be coupled to locations on the left side of the face as well.

In one embodiment, microexpressions are identified from samples, with each sample derived from a set of images taken from a single camera. For example, the set of images may include sequential images taken during a certain period (e.g., 0.5 seconds) from a certain camera coupled to a frame of an HMS worn by a user. It is to be noted, that due to the dynamic nature of AUs, at least some of the features may be derived from multiple temporally successive images, e.g., to reflect properties related to facial movements involved in microexpressions.

In another embodiment, microexpressions are identified from samples, with each sample derived from a set of images taken from multiple cameras. For example, the set of images may include sequential sets of corresponding images taken during a certain period (e.g., 0.5 seconds) from multiple cameras coupled to a frame of an HMS worn by a user. In this example, each camera is coupled to the frame at a certain location and/or has a certain orientation to the face, which is different from the location and/or orientation of the other cameras. When features are extracted in order to identify the microexpressions, they may be extracted from each image independently and/or jointly (in a similar fashion to the way described above in which features may be generated for landmark identification). Additionally or alternatively, as explained above, certain feature values may be extracted from multiple temporally successive images, e.g., to reflect properties related to facial movements involved in microexpressions.

In some embodiments, images in a training set used to train the microexpression identifier may contain images of multiple users, in multiple conditions (e.g., different lighting conditions) and/or while making different facial expressions (e.g., expressing different emotions). Having a diverse set of images included the training set of a landmark detector can help improve its generalizability, making it more likely to accurately identify landmarks in unseen images that were not included in the training set. In other embodiments, images in a training set used to train the microexpression identifier may mostly contain images of a certain user in order to train a microexpression identifier that works well with images of the certain user.

Obtaining images for a training set for training the microexpression identifier is typically straightforward and involves acquiring images of a user's face from cameras coupled to a frame of an HMS while the user wears the frame. However, due to the involuntary nature of microexpressions, and their short durations, getting images from periods of times in which a user expresses a genuine microexpression may be challenging. Some of the approaches that may be used in some embodiments to collect microexpressions that may be used (possibly after adaptations to include cameras coupled to a frame of an HMS) are discussed in Li et al. "A spontaneous microexpression database: Inducement, collection and baseline", in the 10th IEEE International Conference and Workshops on Automatic Face and Gesture Recognition (FG), 2013, and the references mentioned therein.

Once training images are acquired, they may be converted to samples comprising feature values. The feature values may include various types such as features derived from locations of landmarks, identified action units, blendshape weights and/or low-level features described below, such as features derived using Gabor filters, local binary patterns and their derivatives, features derived using algorithms such as SIFT, SURF, and/or ORB, image keypoints, HOG descriptors, and features derived using PCA or LDA. Additional examples of features may also include features derived from multiple images taken at different times, such as volume local binary patterns (VLBP), optical strain-based features, and/or cuboids that are described in this disclosure. In addition to deriving feature values from images, for training, samples derived from the images need to be assigned with the locations of the facial landmarks on the images. Labels may be provided in different embodiments in various ways. Some examples are given below.

In one embodiment, labels are marked by an expert. For example, the expert may be a human that views images taken by one or more camera coupled to a frame of an HMS at a certain location and/or orientation and indicates which microexpressions were expressed. For example, the expert may mark identify which microexpressions were expressed in images. Optionally, the human expert may view frontal images of the user taken at the same time as the images from the cameras coupled to the HMS were taken, and determine which microexpressions were expressed in those images. A human expert may be more capable of accurately determining microexpressions from the standard frontal images that are more frequently encountered in the art.

In one embodiment, some of the images provided for training may be premeditated. For example, a user may be asked to move certain facial muscle and/or make certain facial expressions while the images are taken by the one or more cameras coupled to the frame.

In other embodiments, an automatic labeling method may be employed to identify microexpressions in a set of images comprising sequences of images taken by one or more cameras coupled to a frame of an HMS worn by a user. One example of an automatic microexpression labeling system for such images involves an additional camera that takes frontals image of the user. The camera that takes frontal images may be any camera that takes images of the face of the user from an optical distance of at least 15 cm from the face. For example, the camera that takes the frontal images may be embedded in a smartphone held by the user, a webcam, and/or a camera belonging to an entertainment system (e.g., Microsoft's Kinect or a camera embedded in a TV). In another example, the camera that takes the frontal image may be a camera of another user (e.g., mounted to an HMS of the other user). In still another example, the camera may be mounted to the user, such as a camera that gives an image corresponding to the line of the sight of the user, but in this case, in order to get a frontal image of the user, the user stands in front of a mirror. The frontal images of the user may be used to identify microexpressions using algorithms known in the art. Examples of such algorithms are given above. Optionally, in order to obtain less obstructed frontal images of the user, in some embodiments, certain elements such as lenses and/or displays may be removed from the HMS when frontal images of the user are acquired, as discussed above in the discussion related to obtaining frontal images for training a landmark identifier.

Given training samples and corresponding labels describing the microexpressions appearing in the images from which the samples are derived, various machine learning algorithms may be used to train the microexpression identifier, such as SVMS, multiple kernel learning, and/or other machine learning algorithms known in the art. The microexpression identifier may then be used to identify microexpressions in samples derived from images for which the label (microexpression) is unknown.

Some embodiments may involve use of a potentially large number of features to represent images and/or sets of images, as described in the examples above. In order to increase computational efficiency and/or improve performance, feature selection is utilized, in some embodiments, to reduce the number of features. Feature selection may also be referred to herein as "dimensionality reduction". Feature selection may involve techniques that create new features from other features (e.g., various projection methods or PCA described below). Additionally or alternatively, feature selection may involve selection of a subset of existing features that includes relevant features for the task at hand (e.g., recognizing facial expressions and/or emotions or mapping expressions to a facial model). Many feature dimensionality reduction techniques have been proposed in the literature. Among them, Principal Component Analysis (PCA) has been widely used for feature reduction in face recognition research for decades. Another example of a feature reduction technique known in the art that may be used in some embodiments is Fisher Linear Discriminant (FLD). FLD attempts to project the most discriminative features for class distinction. Other examples of approaches that involve selection of a subset of the possible features, which are known in the art and may be used in some embodiments include branch and bound, sequential selection, mutual information (MI), Minimum Redundancy Maximum Relevance (mRMR), or evolutionary approaches such as Particle Swarm Optimization (PSO). Additional discussion regarding features selection and/or generation techniques that may be used for vision-related application are described in Neoh et al., "Intelligent facial emotion recognition using a layered encoding cascade optimization model", Applied Soft Computing 34 (2015): 72-93. Bartlett et al. "Recognizing facial expression: machine learning and application to spontaneous behavior", in Computer Vision and Pattern Recognition, 2005 (CVPR 2005), IEEE Computer Society Conference on. Vol. 2, pp. 568-573, also describe various feature selection approaches that may be used in detection of facial expressions, such as selection using AdaBoost and/or reduction of dimensionality using principal component analysis (PCA).

Given feature values extracted from images of video streams, as described above, various machine learning models may be trained and utilized for identifying facial expressions in various ways. Some examples of machine learning-based approaches for identifying facial expressions were given in the references that discussed types of feature values (e.g., facial landmarks and action units). Following are some examples of approaches that may be utilized by one skilled in the art (possibly with slight modifications as described above) in embodiments described herein.

In one example, methods following the teachings of Bartlett, et al. "Recognizing facial expression: machine learning and application to spontaneous behavior", in Computer Vision and Pattern Recognition, 2005 (CVPR 2005), IEEE Computer Society Conference on. Vol. 2, pp. 568-573, may be used. Bartlett et al. describe experiments in which various approaches such as support vector machines (SVMs), linear discriminant analysis (LDA), and/or AdaBoost were used successfully for this task.

In another example, machine learning methods descried in Littlewort, et al. "Dynamics of facial expression extracted automatically from video", in Image and Vision Computing 24.6 (2006): 615-625, may be used to facial expressions. Littlewort et al. describe fully automatic recognition of facial expressions, using diverse machine learning approaches including AdaBoost, support vector machines, and linear discriminant analysis.

In still another example, methods adapted from the teachings of El Kaliouby and Robinson, "Real-time inference of complex mental states from facial expressions and head gestures", in Real-time vision for human-computer interaction, Springer US, 2005, pages 181-200, may be utilized for identifying facial expressions and/or emotional response. El Kaliouby and Robinson describe systems in which video input is abstract into different levels, each representing head and facial events at different granularities of spatial and temporal abstraction. Dynamic Bayesian Networks are used to model the unfolding of head and facial displays, and corresponding mental states over time. The system's recognition accuracy and real-time performance is described for six classes of complex mental states: agreeing, concentrating, disagreeing, being interested, thinking, and being unsure.

In yet another example, methods adapted from the teachings of Fanelli et al. "Hough forest-based facial expression recognition from video sequences", in Trends and Topics in Computer Vision, Springer Berlin Heidelberg (2012), pp: 195-206, may be used to identify facial expressions from image sequences. Fanelli et al. utilize a Hough transform voting method based on randomized forests in order to determine what facial expressions are displayed in a sequence of images.

Tasks involving determining facial expressions and/or emotional response may be considered, in some embodiments, to involve a predictor. In some embodiments, a module that receives a query that includes a sample (e.g., a vector of one or more feature values), and predicts a label for that sample (e.g., a class associated with the sample), is referred to as a "predictor". A sample provided to a predictor in order to receive a prediction for it may be referred to as a "query sample" or simply a "sample". A value returned by the predictor, which it computed from a sample given to it as input, may be referred to herein as a "label" and/or a "predicted value". A pair that includes a sample and a corresponding label may be referred to as a "labeled sample". A sample that is used for training a predictor may be referred to as a "training sample" or simply a "sample". Similarly, a sample that is used for testing a predictor may be referred to as a "testing sample" or simply a sample. In typical embodiments, samples used for various purposes (e.g., training, testing, and/or a query) are assumed to have a similar structure (e.g., similar dimensionality) and are assumed to be generated in a similar process (e.g., they all undergo the same type of preprocessing). Optionally, a sample for a predictor (e.g., a sample used as training data and/or a query sample) includes a description of one or more feature values. Optionally, at least some of the feature values are numerical values (e.g., integer and/or real values). Optionally, at least some of the feature values may be categorial values that may be represented as numerical values (e.g., via indexes for different categories). Optionally, feature values comprised in a sample may be represented as a vector of values.

Various preprocessing, processing, and/or feature extraction techniques known in the art may be used to generate the one or more feature values comprised in a sample. Additionally, in some embodiments, samples may contain noisy or missing values. There various methods known in the art that may be used to address such cases. It is to be noted that many of the examples given above of machine learning-based algorithms known in the art, such as algorithms for identifying landmarks, action units, and/or facial expressions involve predictors as the term is described above.

In some embodiments, a predictor receives a sample that includes feature values generated based on one or more images from one or more video streams of one or more cameras coupled to a frame of an HMS worn by a user. Optionally, based on an evaluation of the sample, the predictor returns a label indicating a facial expression the user expressed. Such a predictor may be referred to herein as a facial expression predictor. Optionally, based on an evaluation of the sample, the predictor returns a label indicating an emotional response of the user. Such a predictor may be referred to herein as emotional response predictor (ERP). Samples provided to such predictors may include feature values that include values of one or more of the high-level and/or low-level features described in this disclosure and/or in the references mentioned in this disclosure, and/or are derived from one or more of those feature values. Examples of the high-level features include facial-related values and their derivatives such as location and dimensions of facial features and/or landmarks, and/or identification of action units (AUs) in images. Additional examples of high-level features include blendshape weights and microexpressions. Examples of low level features that may be used include low-level features include features derived using Gabor filters, local binary patterns and their derivatives, features derived using algorithms such as SIFT, SURF, and/or ORB, image keypoints, HOG descriptors, and features derived using PCA or LDA. Similarly, the features may include features derived from multiple images taken at different times, such as volume local binary patterns (VLBP), optical strain-based features.

It is to be noted that since facial expressions typically indicate emotional response, in some embodiments, the terms "facial expression" and "emotional response" may be used interchangeably. Similarly, in those embodiments, the terms "facial expression predictor" and "emotional response predictor" may be used interchangeably. The main difference between the way the terms "facial expression" and "emotional response" are typically used herein is that emotional response may be something that in some embodiments is measured over a longer period of time (e.g., seconds, minutes, hours, days, or even longer). For example, emotional response may be based on multiple facial expressions identified over time. Additionally, in some embodiments, a sample for predictor of emotional response may include, in addition to feature values derived from images taken by cameras, other feature values generated based on data from other sources, as described below (though in some embodiments a sample fir facial expression predictor may also include feature values generated based on data from other sources).

In some embodiments, a label that may serve as prediction value for a query sample provided to a predictor, may take one or more types of values. For example, a label maybe include a discrete categorial value (e.g., a category describing an emotional response or one or more AUs), a numerical value (e.g., a real number describing the extent a certain emotion was expressed), and/or a multidimensional value (e.g., a point in multidimensional space, a database record, and/or another sample).

Emotional responses, such as labels returned by an emotional response predictor, may be represented by various types of values in embodiments described herein. In one embodiment, emotions are represented using discrete categories. For example, the categories may include three emotional states: negatively excited, positively excited, and neutral. In another example, the categories may include emotions such as happiness, surprise, anger, fear, disgust, and sadness. In still another example, the emotions may selected from the following set that includes basic emotions, including a range of positive and negative emotions such as Amusement, Contempt, Contentment, Embarrassment, Excitement, Guilt, Pride in achievement, Relief, Satisfaction, Sensory pleasure, and Shame, as described by Ekman P. (1999), "Basic Emotions", in Dalgleish Power, Handbook of Cognition and Emotion, Chichester, UK: Wiley.

In another embodiment, emotions are represented using a multidimensional representation, which typically characterizes the emotion in terms of a small number of dimensions. In one example, emotional states are represented as points in a two dimensional space of Arousal and Valence. Arousal describes the physical activation and valence the pleasantness or hedonic value. Each detectable experienced emotion is assumed to fall in a specified region in that two-dimensional space. Other dimensions that are typically used to represent emotions include potency/control (refers to the individual's sense of power or control over the eliciting event), expectation (the degree of anticipating or being taken unaware), and intensity (how far a person is away from a state of pure, cool rationality). The various dimensions used to represent emotions are often correlated. For example, the values of arousal and valence are often correlated, with very few emotional displays being recorded with high arousal and neutral valence. In one example, emotions are represented as points on a circle in a two dimensional space pleasure and arousal, such as the circumflex of emotions. In another example, emotions may be represented as points in a two dimensional space whose axes correspond to positive affect (PA) and negative affect (NA), as described by Watson et al. (1988), "Development and validation of brief measures of positive and negative affect: the PANAS scales", Journal of Personality and Social Psychology 54.6: 1063.

In yet another embodiment, emotions are represented using a numerical value that represents the intensity of the emotional state with respect to a specific emotion. For example, a numerical value stating how much the user is enthusiastic, interested, and/or happy. Optionally, the numeric value for the emotional state may be derived from a multidimensional space representation of emotion; for instance, by projecting the multidimensional representation of emotion to the nearest point on a line in the multidimensional space.

In some embodiments, a predictor may utilize a model in order to make predictions for a given query sample. A plethora of machine learning algorithms are available for training different types of models that can be used for this purpose. Many examples of machine learning models and approaches are given in the examples discussed above. In general, some of the algorithmic approaches that may be used for creating the predictor are classification, clustering, function prediction, and/or density estimation. Those skilled in the art can select the appropriate type of model and/or algorithm depending on the characteristics of the training data (e.g., its dimensionality or the number of samples), and/or the type of value used as labels (e.g., discrete value, real value, or multidimensional).

In one example, classification methods like Support Vector Machines (SVMs), Naive Bayes, nearest neighbor, decision trees, logistic regression, and/or neural networks can be used to create a predictor that predicts a discrete class label. In another example, methods like SVMs for regression, neural networks, linear regression, and/or gradient boosted decision trees can be used to create a predictor for real-valued labels, and/or multidimensional labels. In yet another example, a predictor may utilize clustering of training samples in order to partition a sample space such that new query samples can be placed in clusters and assigned labels according to the clusters to which they belong. In a somewhat similar approach, a predictor may utilize a collection of labeled samples in order to perform nearest neighbor classification (in which a query sample is assigned a label according to one or more of the labeled samples that are nearest to them in some space).

In one embodiment, semi-supervised learning methods may be used to train a predictor's model, such as bootstrapping, mixture models and Expectation Maximization, and/or co-training. Semi-supervised learning methods are able to utilize as training data unlabeled samples in addition to the labeled samples.

In one embodiment, a predictor may return as a label other samples that are similar to a given query sample. For example, a nearest neighbor approach method may return one or more samples that are closest in the data space to the query sample (and thus in a sense are most similar to it.)

In another embodiment, a predictor may return a value representing a probability of a sample according to a model utilized by the predictor. For example, the value may represent a probability of the sample according to a probability density function, which is described and/or defined by the model, and assigns probability values to at least some of the samples in the space of all possible samples. For example, the predictor may be a single class support vector machine, a naïve Bayes classifier, a graphical model (e.g., Bayesian network), or a maximum entropy model.

In addition to a label predicted for a query sample, in some embodiments, a predictor may provide a value describing a level of confidence in its prediction of the label (e.g., confidence that the user had a certain emotional response or the confidence that the user expressed a certain facial expression). In some cases, the value describing the confidence level may be derived directly from the prediction process itself. For example, a predictor utilizing a classifier to select a label for a given query sample may provide a probability or score according to which the specific label was chosen (e.g., a naïve Bayes' posterior probability of the selected label or a probability derived from the distance of the sample from the hyperplane when using an SVM).

In one embodiment, a predictor making a prediction for a query sample returns a confidence interval as its prediction or in addition to a predicted label. A confidence interval is a range of values and an associated probability that represents the chance that the true value corresponding to the prediction falls within the range of values. For example, if a prediction is made according to an empirically determined Normal distribution with a mean m and standard deviation $\sigma$, the range $[m-2\sigma, m+2\sigma]$ corresponds approximately to a 95% confidence interval surrounding the mean value m.

Samples provided to a predictor and/or that are used for its training, may in some embodiments, be generated from data that may be received from various sources (in addition to cameras), and have various characteristics (e.g., the data may comprise numerical values, text, images, audio, video, and/or other types of data). Various dimensionality reduction techniques that may be used with respect to images were discussed above In some embodiments, a predictor may be described as including and/or utilizing a model. A model that is included in a predictor, and/or utilized by it, may include parameters used by the predictor to compute a prediction value. Non-limiting examples of such parameters include support vectors (e.g., used by an SVM), points in a multidimensional space (e.g., used by a Nearest-Neighbor predictor), regression coefficients, distribution parameters (e.g., used by a graphical model), topology and/or weight parameters (e.g., used by a neural network). When a model, contains parameters that are used by the predictor to compute a prediction value, such as in the examples above, the terms "model" and "predictor" (and derivatives thereof) may at times be used interchangeably herein. Thus, for example, language reciting "a model that predicts" or "a model used for predicting" is acceptable. Similarly, when a discussion relates to parameters of a predictor, this may be interpreted as relating to parameters of a model used by the predictor.

The type and quantity of training data used to train a predictor's model can have a dramatic influence on the quality of the predictions made by the predictor. Generally speaking, the more data available for training a model, and the more the training samples are similar to the samples on which the predictor will be used (also referred to as test samples), the more accurate the predictions for the test samples are likely to be. Therefore, when training a model that will be used to make predictions regarding a specific user, it may be beneficial to collect training data from the user (e.g., data comprising measurements of the specific user). In such a case, the predictor may be referred to as a "personalized predictor".

Due to the wide variety in human heads and faces (e.g., various head shapes, hairlines, facial features, and pigmentation), in some embodiments, multiple predictors may be trained from data obtained from subsets of similar people. For example, there may be a separate predictor trained for bearded men, teenage Caucasian girls, or Asian men in the ages 20-40, etc. Optionally, subsets of similar users are selected according to their demographic characteristics and/or their appearance. Additionally or alternatively, users may be clustered according to images of their face and/or a model of their face, as described further below. Optionally, a model is trained for each cluster of similar users by collecting labeled images of the users belonging to each cluster or group of users, and providing the labeled images to an algorithm for training one or more of the machine learning-based predictors described herein.

In some embodiments, making predictions for a user from images of the user involves identifying one or more of the following from the images: landmarks, action units, facial expressions, and/or emotional response. Optionally, in order to make a prediction for the user, one or more suitable predictors are selected for the user from among the multiple predictors. In one example, a suitable model is selected for the user based on the user's demographic and/or appearance characteristics. For instance, if there is a predictor trained from images of males between ages 20-40, and the user is such a person, then that predictor is selected for the user. In another example, an image of the user and/or a model of the user's face may be used to find one or more clusters to which the user may belong (e.g., by applying the distance function that measures the similarity between the image and/or model of the user and representative images and/or models of clusters). Thus, in these embodiments, instead of using a predictor trained on images from a large pool of diverse people, the user may receive results of a predictor that is trained on images that are more similar to him or her, which may improve the accuracy of predictions made for the user.

Training a predictor and/or utilizing a predictor may be done utilizing various computer system architectures. In particular, some architectures may involve a single machine and/or single processor, while other architectures may be distributed, involving many processors (e.g., possibly thousands or more processors on various machines). For example, some predictors may be trained on distributed architectures such as Hadoop, utilizing distributed machine learning-based algorithms. In this example, it is possible that each processor will only have access to a portion of the training data. Another example of a distributed architecture that may be utilized in some embodiments is a privacy-preserving architecture in which users process their own data. In this example, a distributed machine learning training algorithm may allow a certain portion of the training procedure to be performed by users, each processing their own data and providing statistics computed from the data rather than the actual data itself. The distributed training procedure may then aggregate the statistics in order to generate a model for the predictor.

In some embodiments, a sample for a predictor, such as a facial expression predictor and/or an emotional response predictor, may include, in addition to feature values derived from images obtained by cameras coupled to a frame of an HMS, feature values derived from a measurement of affective response. Optionally, the measurement of affective response is obtained utilizing one or more sensors that measure a physiological signal and/or a behavioral cue of a user. Optionally, the one or more sensors used to obtain the measurement of affective response do not include a camera coupled to a frame of an HMS worn by a user.

Some examples of types of sensors that may be used to measure affective response and/or values that may be comprised in a measurement of affective response include the following: (i) Heart Rate (HR), Heart Rate Variability (HRV), and Blood-Volume Pulse (BVP), and/or other parameters relating to blood flow, which may be determined by various means such as electrocardiogram (ECG), photoplethysmogram (PPG), and/or impedance cardiography (ICG); (ii) Skin conductance (SC), which may be measured via sensors for Galvanic Skin Response (GSR), which may also be referred to as Electrodermal Activity (EDA); (iii) Skin Temperature (ST) may be measured, for example, with various types of thermometers; (iv) Brain activity based on Magnetoencephalography (MEG); (v) Muscle activity, which may be determine via electrical signals indicative of activity of muscles, e.g., measured with electromyography (EMG). In one example, surface electromyography (sEMG) may be used to measure muscle activity of frontalis and corrugator supercilii muscles, indicative of eyebrow movement, and from which emotional response may be recognized; (vi) Eye movement, e.g., measured with electrooculography (EOG); and (vii) Brain activity and/or brainwave patterns, which may be measured with electroencephalography (EEG), which is elaborated on below.

EEG is a common method for recording brain signals in humans because it is safe, affordable, and easy to use; it also has a high temporal resolution (of the order of milliseconds). EEG electrodes, placed on the scalp, can be either "passive" or "active". Passive electrodes, which are metallic, are connected to an amplifier, e.g., by a cable. Active electrodes may have an inbuilt preamplifier to make them less sensitive to environmental noise and cable movements. Some types of electrodes may need gel or saline liquid to operate, in order to reduce the skin-electrode contact impedance. While other types of EEG electrodes can operate without a gel or saline and are considered "dry electrodes". There are various brain activity patterns that may be measured by EEG. Some of the popular ones often used in affective computing include Event Related Desynchronization/Synchronization, Event Related Potentials (e.g., P300 wave and error potentials), and Steady State Evoked Potentials. Measurements of EEG electrodes are typically subjected to various feature extraction techniques that aim to represent raw or preprocessed EEG signals by an ideally small number of relevant values, which describe the task-relevant information contained in the signals. For example, these features may be the power of the EEG over selected channels, and specific frequency bands. Various feature extraction techniques are discussed in more detail in Bashashati, et al., "A survey of signal processing algorithms in brain-computer interfaces based on electrical brain signals", in Journal of Neural engineering, 4(2):R35, 57, 2007. Additional discussion about the using EEG in affective computing and brain computer interfaces (BCI) can be found in Lotte, et al., "Electroencephalography (EEG)-based Brain Computer Interfaces", in Wiley Encyclopedia of Electrical and Electronics Engineering, pp. 44, 2015, and the references cited therein.

In some embodiments, a measurement of affective response of a user comprises, and/or is based on, a behavioral cue of the user. A behavioral cue of the user is obtained by monitoring the user in order to detect things such as facial expressions of the user, gestures made by the user, tone of voice, and/or other movements of the user's body (e.g., fidgeting, twitching, or shaking). The behavioral cues may be measured utilizing various types of sensors. Some non-limiting examples include an image capturing device (e.g., a camera), a movement sensor, a microphone, an accelerometer, a magnetic sensor, and/or a pressure sensor. In one example, a behavioral cue may involve prosodic features of a user's speech such as pitch, volume, tempo, tone, and/or stress (e.g., stressing of certain syllables), which may be indicative of the emotional state of the user. In another example, a behavioral cue may be the frequency of movement of a body (e.g., due to shifting and changing posture when sitting, laying down, or standing). In this example, a sensor embedded in a device such as accelerometers in a smartphone or smartwatch may be used to take the measurement of the behavioral cue.

In some embodiments, samples provided to a predictor may include feature values from multiple types of sources (referred to as modalities). For examples, the samples may include feature values derived from images from video streams of cameras coupled to a frame of an HMS, and in addition, feature values generated using EEG, GSR, and/or EMG. Processing this type of data may optionally involve fusion of data from the multiple modalities. Different types of data fusion techniques may be employed, for example feature-level fusion, decision-level fusion, or model-level fusion, as discussed in Nicolaou et al. (2011), "Continuous Prediction of Spontaneous Affect from Multiple Cues and Modalities in Valence-Arousal Space", IEEE Transactions on Affective Computing. Another example of use of fusion-based predictors of emotional response may be found in Schels et al. (2013), "Multi-modal classifier-fusion for the recognition of emotions", Chapter 4 in Coverbal synchrony in Human-Machine Interaction. The benefits of multimodal fusion typically include more resistance to noise (e.g., noisy sensor measurements) and missing data, which can lead to better affect detection when compared to affect detection from a single modality. For example, in meta-analysis described in D'mello and Kory (2015) "A Review and Meta-Analysis of Multimodal Affect Detection Systems" in ACM Computing Surveys (CSUR) 47.3: 43, multimodal affect systems were found to be more accurate than their best unimodal counterparts in 85% for the systems surveyed.

In one embodiment, a predictor may receive as input, e.g., as one or more feature values comprised in a sample), a baseline affective response corresponding to the user. Optionally, the baseline affective response value may be derived from measurements of affective response of the user (e.g., earlier measurements) and/or it may be a predicted value (e.g., based on measurements of other users and/or a model for baseline affective response values). Accounting for the baseline affective response value (e.g., by normalizing the measurement of affective response according to the baseline), may enable the predictor, in some embodiments, to more accurately predict the emotional response a user is feeling.

In some embodiments, some of the feature values in a sample for a predictor may be derived from additional information not obtained from measuring the user. Optionally, the additional information is used to provide context with respect to the user and/or an experience the user is having. Knowing context may be helpful since depending on the sensors used, in some embodiments, it may be the case that in different conditions the same signal values may be correspond to different emotions (e.g., extreme excitement or high stress). Knowing the context (e.g., playing a difficult level in a game or hearing a noise when alone in a dark parking lot) can assist in deciding which emotion the user is having.

Context may be given by identifying a situation the user is in. Examples of situations may include a mood of the user, a health state of the user, the type of activity the user is partaking in (e.g., relaxing, exercising, working, and/or shopping), the location the user is (e.g., at home, in public, or at work), and/or the alertness level of the user. The additional situation information may be used by a predictor improve the prediction of the emotional response of the user and/or facial expression of the user. In one example, the predictor may normalize values according to the situation (e.g., according to situation-specific baselines). In another example, the predictor may select certain models to use based on the additional information. For example, separate models may be used by a predictor for different situations a user is in, such as being at home vs. outside, or for when the user is alone vs. in a group. In still another example, separate models may be used for different types of experiences. For example, a first model may be used for determining emotional response to experiences that are considered primarily physical activities (e.g., cycling or jogging), while a second model may be used for experiences that may be considered primarily mental activities (e.g., consuming digital content).

In one embodiment, additional information received by predictor may include information derived from semantic analysis of communications of a user. The choice of words a user uses to communicate (in addition to the way the user says the words), may be indicative of the emotion being expressed. For example, semantic analysis may help determine whether a user is very excited or very angry.

In another embodiment, additional information received by a predictor may include information derived from measurements of the environment the user is in. For example, the additional information may include values that are indicative of one or more of the following: the temperature, humidity, precipitation levels, noise level, air pollution level, allergen levels, time of day, and ambient illumination level.

Similar to the discussion regarding training of predictors such as landmark identifiers, action unit identifiers, and facial expression identifier, training a predictor of emotional response may require appropriate training samples. In particular, training a personalized model for a user, which involves collecting samples that involve the user (possibly in addition to samples derived from measurements of other users). These samples typically feature values (derived from images and optionally other signals) and labels corresponding to the samples, representing an emotional response the user had when the measurements were taken. Inferring what emotional response the user had at a certain time measurements (e.g., images) were taken can be done in various ways.

In one embodiment, determining emotional response labels for samples may be done utilizing additional feature values that are not included in the samples. For example, the sample may include feature values derived from images, and the additional feature values may include signals derived from EEG, GSR, heart rate, voice analysis, etc. The additional feature values may be used to determine emotional response using a different predictor than the one being trained (e.g., a predictor of emotional response from EEG signals). Then the obtained label may be used to train a certain predictor that is not the different predictor, such as predictor of emotional response from image-based features. In one example, times when a user is measured by additional sensors (e.g., EEG, GSR, and/or external cameras that provide full frontal view) may be utilized to collect labeled samples for training a suitable predictor for time when the additional sensors are not used.

It is to be noted that similar to some embodiments described above involving the identifying of landmarks, action units, and/or facial expressions. Emotional response labels may be obtained by utilizing an external camera that takes images that include a frontal view of the face of the user, at the same time images are taken by one or more cameras coupled to a frame of an HMS worn by the user. As described above, this process may involve removing portions of the HMS (e.g., removing a display or lenses) and/or using a frame that offers less obfuscation of the face than the HMS, but maintains the cameras in the same locations and/or orientations they have when coupled to the frame of the HMS.

In another embodiment, labels representing an emotional response may be self-reported by a user stating how the user feels at the time. For example, a user may declare how he or she is feeling, select an image representing the emotion, and/or provide another form of rating for his or her feelings. Optionally, the user describes his or her emotional response after being prompted to do so by the software agent.

In another embodiment, labels representing an emotional response may be derived from communications of the user. For example, semantic analysis may be used to determine the meaning of what the user says, writes, and/or communicates in other ways (e.g., via emojis and/or gestures). These emotions may be attributed to samples collected from measurement of the user at the time the communications were made.

One approach, which may be used in some embodiments, for addressing the task of obtaining labeled samples for training a personalized predictor is to use a form of bootstrapping. In one example, training a personalized predictor for a certain user may start by utilizing a general predictor trained on labeled samples obtained from data of multiple user. These labeled samples may be added to a pool of training samples used to train the personalized predictor. As the body of labeled samples increases in size, the predictor trained on them will begin to represent the particular characteristics of how the user expresses emotions. Eventually, after a sufficiently large body of training samples is generated (or some of the samples of multiple users are removed or have their weight decreased), it is likely that the personalized predictor will perform better than a general predictor on the task of identifying the emotional response of the user.

In some embodiments, images from one or more video streams generated by one or more cameras coupled to a frame of an HMS worn by a user are utilized to generate a representation of facial expressions and/or other body movements of the user. In some embodiments, the representation of facial expressions and/or other body movements of the user are done on a rendered avatar of the user. Thus, in real-time, it is possible for a user to re-target motions and detailed expressions to avatars, e.g., for gaming or video conferencing. In other embodiments, the representation of facial expressions and/or other body movements of the user are done via movements of physical robot.

In some embodiments, images captured by one or more cameras coupled to the frame of an HMS worn by a user are converted into feature values. Optionally, the feature values include values of one or more of the high-level and/or low-level features described above, and/or are derived from one or more of the high-level and/or low-level features described above.

The feature values may be utilized to update a real-time representation of the facial expressions of the user via parameters of a 3D model of the user. Optionally, a real-time representation involves updating the 3D model based on feature values derived from an image up to one second after the image was taken. Alternatively, "real-time" may refer to shorter periods between the time images are taken and the time a model is updated and/or an avatar representation is updated accordingly. For example, in different embodiments, real-time may refer to model updates and/or avatar rendering within 0.5 seconds of taking images, within 0.2 seconds, within 0.1 seconds, or even within periods of less than 0.05 seconds.

There are various ways to represent faces via 3D models known in the art. In some embodiments, the 3D models are generated utilizing one or more images captured by cameras. Optionally, algorithms are used to reconstruct the 3D models from color images. Additionally or alternatively, algorithms may be used reconstruct the 3D models by fitting a template mesh to a depth scan of the face. Various types of cameras may be used in different embodiments. In one example, the cameras may be regular RGB cameras. In another example, the cameras may include depth-measuring capabilities (e.g., cameras that utilize IR grids and/or IR sensors such as Microsoft's Kinect). In still another example, the cameras may be light field cameras. In other embodiments, the 3D images may be created de novo, utilizing various 3D modeling software. For example, such models may be created by animators, possibly without relying on similarity to a specific person or being of which an image is taken.

There are various ways known in the art to represent the shape, texture, and/or lighting of a 3D object with models. Many of these models have been used to represent 3D faces. Additionally, a model may include ways in which the representation of the face, such as when rendered on an avatar, may manipulated (deformed). As such, in some embodiments, a 3D model of a face includes the parameters involved in a "facial rigging", for example, as described in Orvalho, et al., "A facial rigging survey", in Proc. of the 33rd Annual Conference of the European Association for Computer Graphics-Eurographics, pp. 10-32. 2012. Following are some examples of elements that may be included in a 3D model of a face used in embodiments described herein.

In some embodiments, the 3D model of the user involves an anatomical physically-based model that approximates the mechanical properties of the face such as skin layers, muscles, fatty tissues, bones, etc. Sifakis et al. "Automatic determination of facial muscle activations from sparse motion capture marker data", in ACM Transactions on Graphics (TOG), 24:3, pp. 417-425, 2005, describe an example of such an anatomically accurate model of facial musculature, passive tissue and underlying skeletal structure using volumetric data. Siakis et al. teach a method for automatically determining muscle activations and bone kinematics that is done by tracking locations of facial landmarks. The resulting rendering of facial expressions on an avatar produces visually plausible, and anatomically correct, deformations with spatial and temporal coherence that provides robustness against outliers in the motion capture data.

In some embodiments, the 3D model of a user comprises a 3D mesh representing the face of the user (e.g., a polygonal mesh such as a triangular mesh). Various examples of ways to construct and/or manipulate 3D mesh models are described in Sheffer, et al., "Mesh parameterization methods and their applications", in Foundations and Trends in Computer Graphics and Vision 2.2 (2006): 105-171.

In some embodiments, the 3D model of the user may involve blendshape models to render an avatar with facial expressions of a user, as described by feature values derived from images captured by one or more cameras coupled to a frame of an HMS worn by the user. Blenshape models are discussed in further detail elsewhere in this disclosure.

Following are some examples of methods known in the art for creating a 3D model of a face and/or body that may be used to represent facial expressions and/or other forms of body movement of a user. These are non-restricting examples; other methods for generating such a model may be used in embodiments described herein.

In one embodiment, a method for generating a 3D model of a face of a user may be based on the teachings of Zollhofer et al. "Automatic reconstruction of personalized avatars from 3D face scans", in Computer Animation and Virtual Worlds 22.2-3 (2011): 195-202. Zollhofer et al. use a Kinect sensor, which combines a regular RGB camera and a 3D scanner that comprises an infrared (IR) projector and an IR camera, in order to acquire input data describing a face. This input data is used by their algorithm to reconstruct a high quality 3D face model with texture from an RGB image and a depth map by fitting a morphable face model to the input data. Morphable face models are discussed further in Blanz et al. "A morphable model for the synthesis of 3D faces", in Proceedings of the 26th annual conference on Computer graphics and interactive techniques, ACM Press/Addison-Wesley Publishing Co., 1999, which describes how to match 3D mesh models to images and various options for manipulating models (e.g., changing characteristics of facial features).

In another embodiment, a method for generating a 3D model of a face of a user may be based on the teachings of Zhang, et al. "Spacetime faces: High-resolution capture for modeling and animation", in Data-Driven 3D Facial Animation, Springer London, 2008, pp: 248-276. Zhang et al. describe a system that employs synchronized video cameras and structured light projectors to record videos of a moving face from multiple viewpoints. A spacetime stereo algorithm is used to compute depth maps accurately. A template surface fitting and tracking procedure is used to combine the depth maps based on optical flow to create face models with vertex correspondence. Once acquired, this sequence of models can be interactively manipulated to create expressions using a data-driven inverse kinematics technique.

In yet another embodiment, a method for generating a 3D model of a face of a user may be based on the teachings of Bradley, et al. "High resolution passive facial performance capture", in ACM Transactions on Graphics (TOG) 29.4 (2010): 41. Bradley et al. describe a passive facial capture approach that uses an array of video cameras, and requires no template facial geometry, no special makeup or markers, and no active lighting. Initial facial geometry is obtained using multi-view stereo, which enables automatically tracking texture detail across frames. This approach can yield a high-resolution sequence of compatibly triangulated and parameterized meshes that may be used to model the face.

In still another embodiment, a method for generating a 3D model of a face of a user may be based on the teachings of Zollhofer et al. "Real-time Non-rigid Reconstruction using an RGB-D Camera", in ACM Transactions on Graphics (TOG) 33.4 (2014): 156. In this reference, Zollhofer et al. describe a combined hardware and software solution for marker-less real-time reconstruction of non-rigidly deforming physical objects (including bodies and/or detailed faces). Their system uses a single self-contained stereo camera unit built from off-the-shelf components and consumer graphics hardware to generate spatio-temporally coherent 3D models at 30 Hz. The general usage scenario comprises two phases: online template acquisition and real-time non-rigid reconstruction. The online template acquisition phase that takes approximately one minute to perform, and from it a triangle mesh model is automatically extracted. The mesh model is preprocessed to create a multi-resolution hierarchy to be used in the online phase, which involves real-time non-rigid reconstruction, which produces a deformed mesh at every time step.

It is to be noted that the hardware setup utilized to generate a 3D model of a user may be different from the hardware setup that is utilized when the model is used on a day-to-day basis, such as when it is used to transfer facial expressions of the user and/or body movements to an animated avatar. In some embodiments, generating a 3D model of the face and/or body of a user may utilize one or more cameras that are located more than 20 cm away from the user and/or generating the model may utilize one or more images of a camera that is not coupled to a frame of an HMS worn by the user. For example, a 3D face and/or body model of the user may be generated utilizing a depth camera system such as Microsoft Kinect mentioned below. However, after the model is generated, utilizing the model to animate an avatar with real-time facial expressions of a user may involve cameras coupled to a frame of an HMS worn by the user, without needing the user to be in front of a depth camera.

In some embodiments, feature values that represent a facial expression of the user are used to render an avatar based on a 3D model that describes a face. Optionally, the feature values are derived from images taken by one or more cameras coupled to a frame of an HMS worn by the user. Optionally, the 3D model is generated based on images of the face of the user taken by the one or more cameras. Additionally or alternatively, the 3D model may be generated based on images taken with a camera that is not one of the one or more cameras, e.g., a camera that is more than 20 cm away from the face of the user), as described above.

Depending on the type of 3D model used (e.g., the type of parameters), and/or the type of feature values that are extracted from the images taken by the one or more cameras captured to the frame, various approaches may be used to convert the feature values into a rendered avatar expressing a facial expression of the user. Following are some non-restricting examples of approaches known in the art that may be used in some embodiments. Other approaches, not described below may also be utilized in embodiments described in this disclosure for that task.

Additional examples of ways blendshapes can be utilized in some embodiments in this disclosure are given in the following references:

(i) Bouaziz, Sofien, Yangang Wang, and Mark Pauly. "Online modeling for realtime facial animation." ACM Transactions on Graphics (TOG) 32.4 (2013): 40. (ii) Ichim et al., "Dynamic 3D Avatar Creation from Hand-held Video Input", in ACM Transactions on Graphics (Proceedings of SIGGRAPH), 2015 (iii) Li with the oculus without the display. (example of blendshapes) (vi) US patent application 20140362091 (v) Kakarla, Mounika, Mohana Reddy, and G. Ram. "A real time facial emotion recognition using depth sensor and interfacing with Second Life based Virtual 3D avatar." Recent Advances and Innovations in Engineering (ICRAIE), 2014. IEEE, 2014. (vi) Liu, Caixia, et al. "Representing affective facial expressions for robots and embodied conversational agents by facial landmarks." International Journal of Social Robotics 5.4 (2013): 619-626. (vii) Mazzei, Daniele, et al. "Hefes: An hybrid engine for facial expressions synthesis to control human-like androids and avatars." Biomedical Robotics and Biomechatronics (BioRob), 2012 4th IEEE RAS & EMBS International Conference on. IEEE, 2012.

Face Transfer is a method for mapping video-recorded performances of one individual to facial animations of another. It extracts visemes (speech-related mouth articulations), expressions, and three-dimensional (3D) pose from monocular video or film footage. These parameters are then used to generate and drive a detailed 3D textured face mesh for a target identity, which can be seamlessly rendered back into target footage. The underlying face model automatically adjusts for how the target performs facial expressions and visemes. The performance data can be easily edited to change the visemes, expressions, pose, or even the identity of the target—the attributes are separably controllable. This supports a wide variety of video rewrite and puppetry applications.

Other face transfer methods that may be used in embodiments described herein are given in the following references: (i) Vlasic, Daniel, et al. "Face transfer with multilinear models." ACM Transactions on Graphics (TOG). Vol. 24. No. 3. ACM, 2005. (ii) Cao, Chen, et al. "3D shape regression for real-time facial animation." ACM Transactions on Graphics (TOG) 32.4 (2013): 41.

In one embodiment, generating a 3D model of a body of a user may be done according to the teachings of Tong et al. "Scanning 3d full human bodies using kinects", in IEEE Transactions on Visualization and Computer Graphics, 18.4 (2012): 643-650. The method of Tong et al. can handle non-rigid alignment with loop closure constraint and complex occlusions. They utilize a two-stage registration algorithm that performs pairwise deformation on the geometry field, followed by global alignment on the deformation field. Registration with a rough template, such as the skeleton model can be utilized in order to enable manipulation of the avatar to perform various movements. Such registration can involve manually segmenting the first frame, and then identifying and tracking the rigid components of each frame, while accumulating the geometric information. Additional information regarding registration of images of a body to a template skeleton may be found in Pekelny and Gotsman, "Articulated object reconstruction and markerless motion capture from depth video", in Computer Graphics Forum (EUROGRAPHICS 2008). Vol. 27. No. 2. Blackwell Publishing Ltd, 2008.

Examples of models of body and shape completion and/or animation of people that may be used in some embodiments are described in the following references: (i) Baak, Andreas, et al. "A data-driven approach for real-time full body pose reconstruction from a depth camera." Consumer Depth Cameras for Computer Vision. Springer London, 2013. 71-98. (ii) Anguelov, Dragomir, et al. "SCAPE: shape completion and animation of people." ACM Transactions on Graphics (TOG). Vol. 24. No. 3. ACM, 2005. (iii) Shape completion, animation and marker-less motion capture of people, animals or characters (iv) U.S. Pat. No. 8,139,067 B2

Examples of models for human actions that may be utilized in embodiments described herein are given in the following references: (i) Sheikh, Yaser, Mumtaz Sheikh, and Mubarak Shah. "Exploring the space of a human action." Computer Vision, 2005. ICCV 2005. Tenth IEEE International Conference on. Vol. 1. IEEE, 2005. (ii) Gall, Juergen, et al. "Motion capture using joint skeleton tracking and surface estimation." Computer Vision and Pattern Recognition, 2009. CVPR 2009. IEEE Conference on. IEEE, 2009. (iii) Poppe, Ronald. "A survey on vision-based human action recognition." Image and vision computing 28.6 (2010): 976-990. (iv) Wang, Jiang, et al. "Robust 3d action recognition with random occupancy patterns." Computer vision—ECCV 2012. Springer Berlin Heidelberg, 2012. 872-885. (v) Chaudhry, Rizwan, et al. "Bio-inspired dynamic 3d discriminative skeletal features for human action recognition." Computer Vision and Pattern Recognition Workshops (CVPRW), 2013 IEEE Conference on. IEEE, 2013. (vi) Tang, Danhang, Tsz-Ho Yu, and Tae-Kyun Kim. "Real-time articulated hand pose estimation using semi-supervised transductive regression forests." Computer Vision (ICCV), 2013 IEEE International Conference on. IEEE, 2013.

In one embodiment, a method for 3D face scan for customized VR headset frame includes the following steps: receiving a 3D model of a user's face; based on the model, selecting a shape for the frame of the head mounted display that best fits the user's face; and (i) printing the frame utilizing a 3D printer to specifically match the face; or (ii) selecting, from a set of predefined shapes, a shape for the frame of the head mounted display that best fits the user's face.

The method may further include the step of selecting at least one location for a sensor and/or identify locations that are not suitable for a sensor based on the face model. The regions may be unsuitable because various reason such as angle and/or size of forehead or ears (varies between humans). Facial hair (beard, mustache, sideburns) can also be problematic. Additionally, piercings and the like can also make some locations inappropriate for certain sensors.

This method selects the appropriate frame for the user based on one or more of the following constraints: to the user's facial dimensions, the sensors the user needs, the specific location of the user's arteries, and/or planned type of usage for the HMD. Optionally, the HMD is designed for quick replacement of frames so that different users having different personalized frames can share the same expensive electronic modules (such as display, processor, memory, thermal sensors, visible spectrum cameras, communication link, IMU).

In one embodiment, an expensive thermal camera (e.g., that costs more than 1,000 USD) is used to measure the location of the superficial temporal artery of the user (optionally with 3D measurements for the face dimensions), and based on this measurement the system selects a HMS with thermal cameras at appropriate locations for the specific facial structure of the user. For example, the system would select different positions for the head mounted thermal cameras for two users having significantly different facial dimensions and superficial temporal artery patterns.

In one embodiment, a grid of sensors is placed nearby one or more ROI, such as nearby the superficial temporal arteries, nostrils, periorbital regions, cheeks. The system is configured to find which one or more sensors provide the best measurements, and base its operation on the best positioned sensors. Additionally or alternatively, the system may turn off sensors that are not positioned well and thus do not provide adequate measurements of the ROI. Additionally or alternatively, when the measurement quality decreases below a threshold, the system turns on the sensors that were turned off, and repeats the process of finding the sensors providing the best measurements.

In one embodiment, the HMS includes a mechanical slider that can move the thermal camera, either manually or electromechanically, to various positions in order to find the best position to measure the ROI. Optionally, the movement is performed by the HMS utilizing an electromechanical device, and the HMS is configured to move the thermal camera until it finds the best position.

Herein, a predetermined value, such as a predetermined confidence level or a predetermined threshold, is a fixed value and/or a value determined any time before performing a calculation that compares a certain value with the predetermined value. A value is also considered to be a predetermined value when the logic, used to determine whether a threshold that utilizes the value is reached, is known before start of performing computations to determine whether the threshold is reached.

In this description, references to "one embodiment" mean that the feature being referred to may be included in at least one embodiment of the invention. Moreover, separate references to "one embodiment" or "some embodiments" in this description do not necessarily refer to the same embodiment. Additionally, references to "one embodiment" and "another embodiment" may not necessarily refer to different embodiments, but may be terms used, at times, to illustrate different aspects of an embodiment.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the details of the order or sequence of steps of operation of methods, or to details of implementation of devices, set in the description, drawings, or examples. Moreover, individual blocks illustrated in the figures may be functional in nature and therefore may not necessarily correspond to discrete hardware elements. In the claims, the terms "first", "second" and so forth are to be interpreted merely as ordinal designations, and shall not be limited in themselves.

While the methods disclosed herein have been described and shown with reference to particular steps performed in a particular order, it is understood that these steps may be combined, sub-divided, and/or reordered to form an equivalent method without departing from the teachings of the embodiments. Accordingly, unless specifically indicated herein, the order and grouping of the steps is not a limitation of the embodiments. Furthermore, methods and mechanisms of the embodiments will sometimes be described in singular form for clarity. However, some embodiments may include multiple iterations of a method or multiple instantiations of a mechanism unless noted otherwise. For example, when a processor is disclosed in one embodiment, the scope of the embodiment is intended to also cover the use of multiple processors. Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

What is claimed is:

1. A system comprising:
    a frame configured to be worn on a user's head;
    first and second cameras, physically coupled to the frame at locations that are to the right and to the left of a symmetry axis that divides the user's face to its right and left sides, respectively, and less than 15 cm away from the user's head;
    wherein the first and second cameras are oriented downward such that portions of the user's torso are in respective fields of view of the first and second cameras when the user stands upright; and a computer configured to estimate an angle between the user's head and the user's torso based on data received from the first and second cameras and orientation of the frame.

2. The system of claim 1, wherein the computer is further configured to estimate posture of the user based on a model and the data received from the first and second cameras, and to train the model based on data received from the first and second cameras;
wherein the training of the model is performed under the assumption that the locations of the first and second cameras, relative to the user's head, do not change by more than 5° even when the user's head performs wide angular and lateral movements.

3. The system of claim 2, wherein the first and second cameras are coupled to the frame at locations that are less than 5 cm away from the user's head, and further comprising an inertial measurement unit (IMU) coupled to the frame and configured to measure orientation of the frame;
wherein the computer is further configured to utilize the orientation for training the model.

4. The system of claim 2, further comprising an external camera, which is not physically coupled to the frame, having a direct line of sight to the front side of the user's torso;
wherein the computer is further configured to utilize data from the external camera to train the model.

5. The system of claim 1, wherein the first camera points at least 20° to the right of the symmetry axis, and the second camera points at least 20° to the left of the symmetry axis; and
wherein the first and second cameras are coupled to the frame at locations that are less than 5 cm away from the user's head.

6. The system of claim 1, further comprising a third camera, physically coupled to the frame at a location behind an ear of the user;
wherein the third camera is oriented downwards such that a portion of the back of the user's torso is in field of view of the third camera when the user stands upright; and
wherein the computer is configured to estimate posture of the user based on data received from the first, second and third cameras.

7. The system of claim 6, wherein the third camera is mounted on an extender that helps to prevent concealment of the portion of the user's torso by at least one of the user's head and hair.

8. The system of claim 1, further comprising third and fourth cameras, physically coupled to the right and left sides of the frame, respectively, at locations that enable them to capture the user's hands when stretched horizontally to the sides;
wherein the computer is configured to estimate posture of the user based on data received from the first, second, third and fourth cameras.

9. The system of claim 1, further comprising a third camera, physically coupled to the frame and oriented such that at least a portion of at least one of the user's eyebrows is in the field of view of the third camera;
wherein the computer is further configured to estimate a facial expression of the user based on a model of a human face parameterized by expression and data extracted from images captured by the third camera.

10. The system of claim 9, wherein the computer is further configured to estimate posture of the user based on a model and data received from the first and second cameras, and to render an avatar of the user based on the posture and the facial expression.

11. The system of claim 10, wherein the frame belongs to an augmented reality device or a virtual reality device, and the computer is further configured to show the user his/her own avatar;
whereby seeing his/her own avatar helps the user to understand how he/she looks to others.

12. The system of claim 10, wherein the frame belongs to an augmented reality device or a virtual reality device, and the computer is further configured to show the user at least two of his/her own avatars who imitate the user by doing what the user does.

13. The system of claim 9, wherein the computer is further configured to estimate posture of the user based on a model and data received from the first and second cameras, the frame belongs to an augmented reality device, and further comprising a communication module configured to send a representation of the posture and the facial expression to a second computer configured to render an avatar of the user;
wherein the second computer is further configured to receive additional measurements of the user from a second augmented reality device that is worn by a second user located nearby the user; and
the second computer is further configured to render, for the second user, an avatar of the user based on: the additional measurements, the posture, and the facial expression.

14. The system of claim 1, wherein the first and second cameras are light field cameras.

15. A method comprising: receiving images from first and second head mounted cameras that are located to the right and to the left of a symmetry axis that divides a user's face to its right and left sides, respectively;
wherein the first and second head mounted cameras physically coupled to a frame worn on the user's head, are located less than 15 cm away from the user's head, and are oriented downward such that portions of the user's torso are in respective fields of view of the first and second head mounted cameras when the user stands upright; and
estimating an angle between the user's head and the user's torso based on the data received from the first and second cameras and orientation of the frame.

16. The method of claim 15, further comprising training a model based on the data received from the first and second head mounted cameras;
wherein the training of the model is performed under the assumption that the locations of the first and second head mounted cameras, relative to the user's head, do not change by more than 5° even when the user's head performs wide angular and lateral movements.

17. The method of claim 15, further comprising a third head mounted camera oriented such that at least a portion of at least one of the user's eyebrows is in the field of view of the third head mounted camera; and further comprising
estimating a facial expression of the user based on a model of a human face parameterized by expression and data extracted from images captured by the third head mounted camera.

18. The method of claim 17, further comprising estimating posture of the user based on a model and data received from the first and second cameras, and rendering an avatar of the user based on the posture and the facial expression.

19. The method of claim 15, wherein the first and second head mounted cameras belong to an augmented reality device or a virtual reality device, and further comprising showing the user his/her own avatar from the side;

whereby seeing his/her own avatar helps the user to understand how he/she looks to others.

* * * * *

UNITED STATES PATENT AND TRADEMARK OFFICE
CERTIFICATE OF CORRECTION

PATENT NO. : 10,165,949 B2
APPLICATION NO. : 15/182592
DATED : January 1, 2019
INVENTOR(S) : Arie Tzvieli, Ari M. Frank and Gil Thieberger It is certified that error appears in the above-identified patent and that said Letters Patent is hereby corrected as shown below:

In the Claims

Claim 15, Column 82, Line 44, please delete "the data" and insert --data--, therefor.

Signed and Sealed this
Twelfth Day of February, 2019

Andrei Iancu
*Director of the United States Patent and Trademark Office*